(12) United States Patent
Blacklidge et al.

(10) Patent No.: US 11,045,305 B2
(45) Date of Patent: Jun. 29, 2021

(54) SOFT TISSUE RETENTION DEVICES, INSTRUMENTATION AND RELATED METHODS

(71) Applicant: Paragon 28, Inc., Englewood, CO (US)

(72) Inventors: Douglas K. Blacklidge, Zionsville, IN (US); Frank S. Bono, Castle Rock, CO (US); Benjamin Majors, Englewood, CO (US); Randy Allard, Golden, CO (US); Shane Miller, Kilbeggan (IE)

(73) Assignee: Paragon 28, Inc., Englewood, CO (US)

( * ) Notice: Subject to any disclaimer, the term of this patent is extended or adjusted under 35 U.S.C. 154(b) by 203 days.

(21) Appl. No.: 16/430,647

(22) Filed: Jun. 4, 2019

(65) Prior Publication Data

US 2019/0350695 A1 Nov. 21, 2019

Related U.S. Application Data

(63) Continuation-in-part of application No. PCT/US2019/030890, filed on May 6, 2019, and a
(Continued)

(51) Int. Cl.
*A61F 2/08* (2006.01)
(52) U.S. Cl.
CPC ..... *A61F 2/0811* (2013.01); *A61F 2002/0817* (2013.01); *A61F 2002/0858* (2013.01);
(Continued)
(58) Field of Classification Search
CPC ...... A61F 2/08; A61F 2/20811; A61B 5/4523; A61B 5/4533; A61B 17/1146
See application file for complete search history.

(56) References Cited

U.S. PATENT DOCUMENTS 5,707,373 A 1/1998 Sevrain et al.
5,893,850 A 4/1999 Cachia
(Continued)

FOREIGN PATENT DOCUMENTS

FR 2928824 A1 9/2009

OTHER PUBLICATIONS

International Search Report and Written Opinion issued for related PCT Application No. PCT/US2017/048780 dated Nov. 21, 2017.
(Continued)

*Primary Examiner* — Jason-Dennis N Stewart
(74) *Attorney, Agent, or Firm* — Heslin Rothenberg Farley & Mesiti P.C.

(57) ABSTRACT

Soft tissue retention devices, instrumentation and related methods are disclosed. The devices include a first member comprising a first head portion and a first threaded shaft portion extending from the first head portion that define a cannulated opening extending therethrough, and a second member comprising a second head portion and a second threaded shaft portion extending from the second head portion that define a cannulated opening that extends therethrough. The inner sides of the first and second head portions includes a row of teeth extending about the periphery thereof. The first head portion also includes a plurality of through holes positioned between the first threaded shaft portion and the row of teeth. The outer sides of the first and second head portions include non-circular drive openings. The instrumentation comprise a handle portion with a through aperture that allows for a user's finger to extend therethrough during an implantation procedure.

21 Claims, 72 Drawing Sheets

Related U.S. Application Data continuation-in-part of application No. 15/687,450, filed on Aug. 26, 2017, now Pat. No. 10,307,245.

(60) Provisional application No. 62/794,565, filed on Jan. 19, 2019, provisional application No. 62/666,918, filed on May 4, 2018, provisional application No. 62/500,574, filed on May 3, 2017, provisional application No. 62/454,100, filed on Feb. 3, 2017, provisional application No. 62/379,789, filed on Aug. 26, 2016.

(52) U.S. Cl.
CPC ............ *A61F 2002/0882* (2013.01); *A61F 2230/0052* (2013.01)

(56) References Cited

U.S. PATENT DOCUMENTS

| | | |
|---|---|---|
| 5,980,526 A | 11/1999 | Johnson et al. |
| 5,980,557 A | 11/1999 | Iserin et al. |
| 6,050,819 A | 4/2000 | Robinson et al. |
| 6,231,606 B1 | 5/2001 | Graf et al. |
| 6,258,091 B1 | 7/2001 | Sevrain et al. |
| 6,302,887 B1 | 10/2001 | Spranza et al. |
| 6,383,187 B2 | 5/2002 | Tormala et al. |
| 6,464,713 B2 | 10/2002 | Bonutti |
| 6,517,543 B1 | 2/2003 | Berrevoets et al. |
| 6,569,186 B1 | 5/2003 | Winters et al. |
| 6,589,244 B1 | 7/2003 | Sevrain et al. |
| 6,648,890 B2 | 11/2003 | Culbert et al. |
| 6,918,912 B2 | 7/2005 | Seemann |
| 7,074,203 B1 | 7/2006 | Johanson et al. |
| 7,578,825 B2 | 8/2009 | Huebner |
| 7,604,659 B2 | 10/2009 | Lee |
| 7,686,807 B2 | 3/2010 | Padget et al. |
| 7,833,255 B2 | 11/2010 | Chow et al. |
| 8,043,347 B2 | 10/2011 | Jiang et al. |
| 8,147,514 B2 | 4/2012 | Bonutti |
| 8,357,186 B2 | 1/2013 | Hadi |
| 8,632,570 B2 | 1/2014 | Biedermann et al. |
| 8,672,985 B2 | 3/2014 | Chow et al. |
| 8,845,699 B2 | 9/2014 | Bonutti |
| 8,858,634 B2 | 10/2014 | Lewallen |
| 8,968,374 B2 | 3/2015 | Hoof et al. |
| 9,011,503 B2 | 4/2015 | Duggal et al. |
| 9,017,404 B2 | 4/2015 | Champagne et al. |
| 9,089,377 B2 | 7/2015 | Brown et al. |
| 9,247,963 B2 | 2/2016 | Kollmer |
| 9,333,069 B2 | 5/2016 | Denham |
| 9,445,842 B2 | 9/2016 | Cianfrani et al. |
| 9,510,883 B2 | 12/2016 | Weiss et al. |
| 2002/0055743 A1 | 5/2002 | Seemann |
| 2005/0240188 A1 | 10/2005 | Chow et al. |
| 2009/0228049 A1 | 9/2009 | Park |
| 2011/0137356 A1 | 6/2011 | Kollmer |
| 2011/0319925 A1 | 12/2011 | Helgerson |
| 2014/0222087 A1 | 8/2014 | Greenberg et al. |
| 2016/0038186 A1 | 2/2016 | Herzog et al. |
| 2016/0135861 A1 | 5/2016 | Kollmer |
| 2018/0055623 A1 | 3/2018 | Blacklidge |

OTHER PUBLICATIONS

International Search Report and Written Opinion of the International Searching Authority for PCT/US2019/030890, dated Jul. 18, 2019, 8 pages.

Extended European Search Report issued in corresponding European Patent Application No. 20188752.8, dated Nov. 13, 2020, 7 pages.

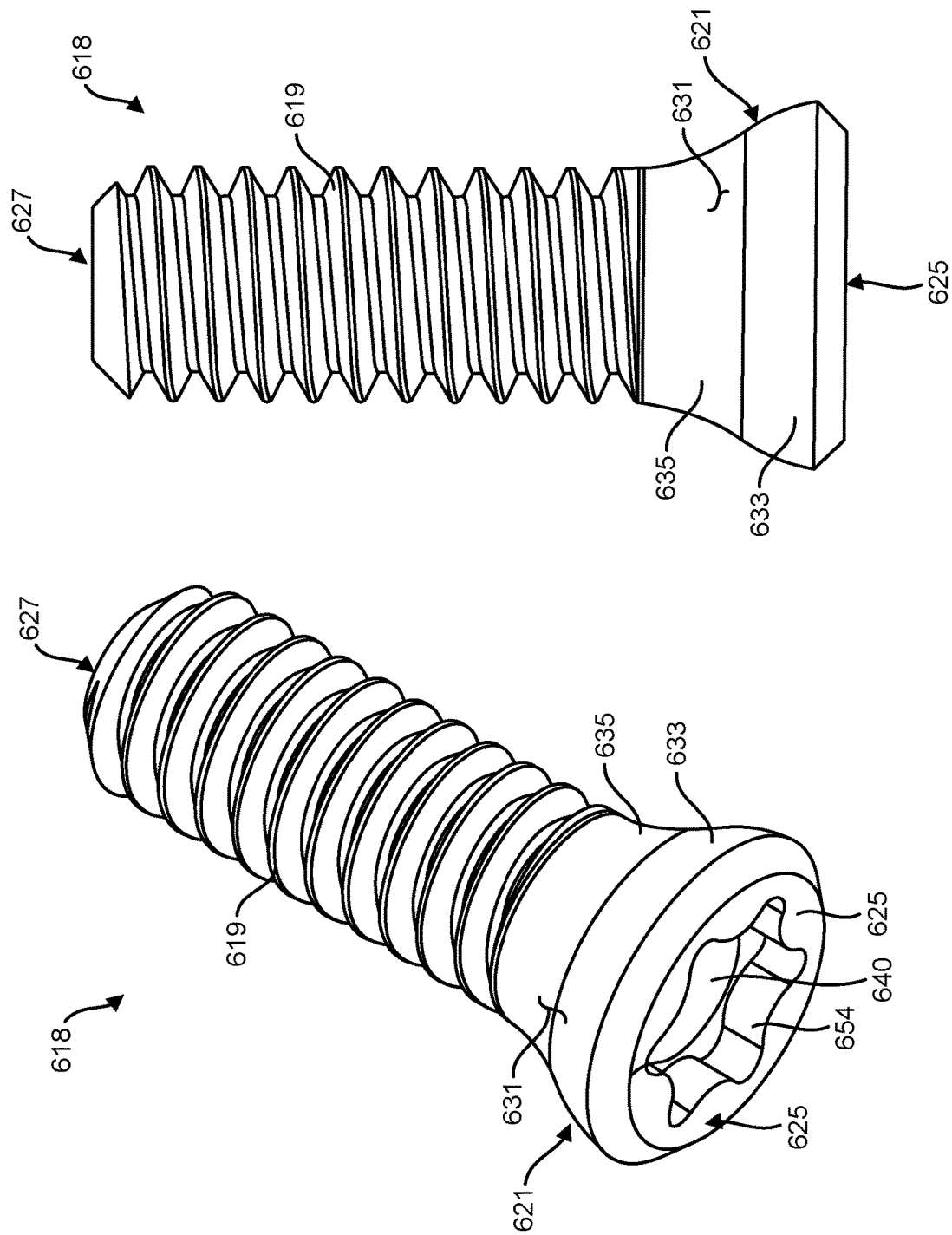

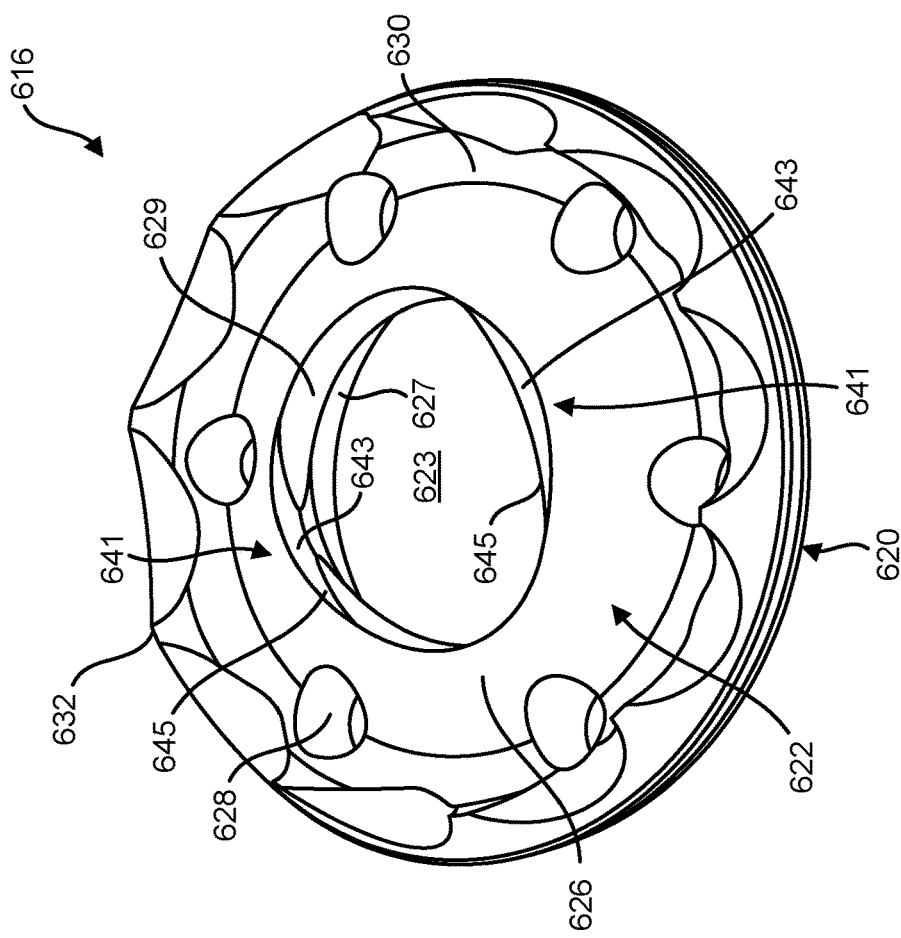
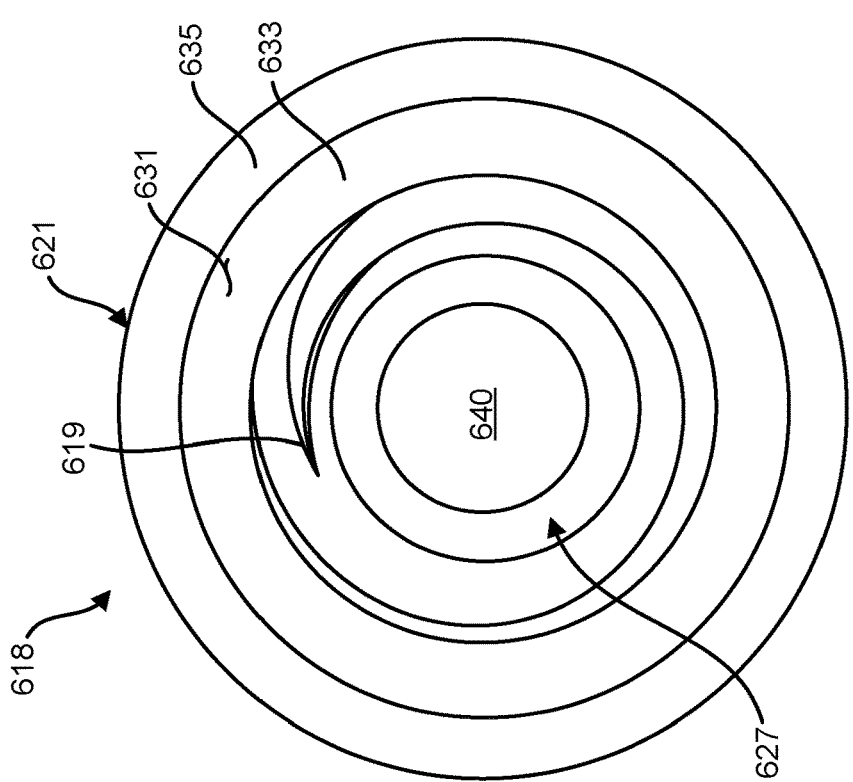

SOFT TISSUE RETENTION DEVICES, INSTRUMENTATION AND RELATED METHODS

CROSS REFERENCE TO RELATED APPLICATIONS

This application is a continuation-in-part of U.S. Non-Provisional patent application Ser. No. 15/687,450, filed on Aug. 26, 2017, and entitled Tendon Retention Device, which claims priority benefit of U.S. Provisional Patent Application No. 62/379,789, filed on Aug. 26, 2016, and entitled Tendon Fixation Device, U.S. Provisional Patent Application No. 62/454,100, filed on Feb. 3, 2017, and entitled Tendon Fixation Device, and U.S. Provisional Patent Application No. 62/500,574, filed on May 3, 2017, and entitled Tendon Fixation Device, and also is a continuation-in-part of International PCT Patent Application No. PCT/US2019/030890, filed on May 6, 2019, and entitled Soft Tendon Retention Device, Instrumentation and Related Methods, which claims priority benefit of U.S. Provisional Patent Application No. 62/666,918, filed May 4, 2018, and entitled Instrument and Method of Installing a Tendon Retention Device During a Tendon to Bone Attachment Procedure, and U.S. Provisional Patent Application No. 62/794,565, filed Jan. 19, 2019, and entitled Soft Tissue Retention Device and Related Methods, which are all hereby incorporated herein by reference in their entireties.

TECHNICAL FIELD

The present disclosure relates to surgical devices, implants, instrumentation, systems and related methods for retention of soft tissue to a bone, and more specifically to surgical devices, implants, instrumentation, systems and related methods for retention of soft tissue (e.g., tendons or ligaments) to a relatively small bone. Some embodiments of the present disclosure are directed to the retention of a flexor digitorum longus tendon to a plantar base of a proximal phalanx of a toe to correct alignment of the toe.

BACKGROUND

In some orthopedic procedures, it is necessary or desirable to attach or re-attach soft tissue (e.g., a tendon or a ligament) to a bone. This is typically accomplished by using an implant/device to physically secure the soft tissue to the bone. During the procedure, the surgeon or other user may utilize multiple instruments during the attachment procedure. These instruments typically require two-hands for engagement and use (e.g., manipulation to effectuate the procedure), which requires the user to constantly switch between different instruments that are not utilized simultaneously. It is difficult to correctly align soft tissue (e.g., a tendon or ligament) to an attachment bone while handling different implantation instruments, especially ones needing two-handed use. Current instruments and methods for attaching soft tissue to a bone are thereby lacking.

The extremities are an area of the body where soft tissue-to-bone attachment procedures are commonplace. One such area is the toes of the foot. For instance, the toes of the human foot commonly become contracted. The contraction of a toe produces pain due to increased pressure at the plantar metatarsal head, the dorsal proximal interphalangeal joint, and the distal end of the toe, for example. Procedures utilized to correct the deformity include tendon release, tendon transfer, partial joint (interphalangeal joint) resection (arthroplasty), and joint (interphalangeal joint) fusion (arthrodesis). For flexible deformities, tendon procedures are often utilized. With a reducible contracture of a toe, a transfer of the flexor digitorum longus tendon to the extensor tendon apparatus is often used with a variety of techniques. The contracted flexor digitorum longus tendon is released from its position on the base of the distal phalanx and it is transferred medial or lateral to the proximal phalanx and sutured to the extensor tendon apparatus dorsally with the tendon tensioned to correct the alignment of the toe. This releases the deforming force of the contracted flexor tendon on the interphalangeal joints while preserving the tendons ability to flex the metatarsophalangeal joint. Correcting the alignment can alleviate the pain associated with the contracture.

Current procedures are performed to facilitate a secure new position for the flexor digitorum longus tendon despite the new location being less than ideal. Procedures to transfer the flexor digitorum longus tendon within the toe typically have the goal of plantar flexing of the proximal phalanx at the metatarsophalangeal joint while releasing the contracture of the interphalangeal joints. Unfortunately, current procedures do not provide attachment of the flexor digitorum longus tendon to the plantar base of the proximal phalanx where it can best serve its new purpose. With attachment of the transferred flexor digitorum longus tendon to a location other than the plantar base of the proximal phalanx, metatarsophalangeal joint instability can persist, and transverse deviation of the toe can be exacerbated. The tendon is not routinely attached to its ideal new position due to technical difficulties and inadequate fixation methods.

During a direct repair of a plantar metatarsophalangeal joint capsule (plantar plate) rupture, the flexor digitorum longus tendon is often used to reinforce the repair. The tendon is secured to the plantar base of the proximal phalanx with transosseus suturing or a small tendon anchor. The bone of the proximal phalangeal base is small and using the currently available tendon suture anchors is difficult—especially considering the challenge of appropriately tensioning the tendon while trying to secure it into its new position with suture. The aging population and associated osteopenia adds to the difficulty of attaining secure tendon to bone fixation. Other than a direct plantar metatarsophalangeal joint ligament repair type procedure, most efforts to simply realign a contracted toe are from dorsal, so the plantar base of the proximal phalanx is not exposed. If a secure means of fixation for the flexor digitorum longus tendon under appropriate tension for correcting a contracted toe could be done efficiently, and reproducibly, the approach to reconstructing the common deformity could be vastly improved.

Many other deformities, conditions, injuries and other anatomical scenarios exist where it is desirable to attach/secure/fix soft tissue, such as but not limited to tendons or ligaments, to a bone, such as but not limited to a relatively small bone (e.g., a phalange, metatarsal or metacarpal).

Devices, implants, instrumentation, systems and related methods and methods that securely attach soft tissue (e.g., a tendon or ligament) to a bone, such as but not limited to a relatively small bone, are thus desirable. Further, devices, implants, instrumentation, systems and related methods that that attach soft tissue (e.g., a tendon or ligament) to a bone and act/function through the bone are also desirable. Further, devices, implants, instrumentation, systems and related methods that provide for a multi-function instrument that is usable with a single hand for implanting a tissue retention device are also desirable.

SUMMARY

The present disclosure is directed toward devices, implants, instrumentation, systems and related methods for retaining or coupling soft tissue (such as, but not limited to, tendons and ligaments) to bones (such as, but not limited to, relatively small bone (for example, bones of the foot and or hand). In some embodiments, the devices, implants, instrumentation, systems and related methods may be configured to couple the flexor digitorum longus tendon to the plantar aspect of a proximal phalangeal base for the correction of a toe contracture, for example. The devices, implants, instrumentation, systems and related methods provide for a secure retention, connection or coupling of the soft tissue to the bone. For example, the devices, implants, systems and related methods include locking teeth that resist de-coupling or backing out from the bone. The devices, implants, instrumentation, systems and related methods are also configured to act/function through the bone. Allowing the instrumentation to act through the bone facilities selection/configuration of an appropriately/selectively sized device/implant/system for a particular bone. Allowing the instrumentation to act through the bone also facilitates blind fitting and tightening of device/implant/system through the bone.

In some embodiments, the present disclosure provides a soft tissue retention device, system and related methods that securely retain or fix a tendon, such as but not limited to an appropriately tensioned flexor digitorum longus tendon, into/to an insertion site, such as but not limited to on the plantar base of the proximal phalanx, through incorporation of innovative threaded fixation and bone retention. In some other embodiments, the present disclosure provides a soft tissue retention device, system and related methods that retain or fix a flexor digitorum brevis to a bone, or retain or fix soft tissue (e.g., tendon and/or ligament) to a bone in another part of a body (e.g., a human body) besides the foot.

In some embodiments, the devices, implants and systems of the present disclosure comprise a soft tissue (e.g., tendon) retention device defined by a first component and a second component, the nomenclature first and second being arbitrary. The first component may be considered a tack while the second component may be considered a sleeve. The tack may be configured for press-fit or instrument aided reception into the soft tissue and adjacent bone to retain the soft tissue against the adjacent bone. The sleeve has an internally threaded bore for threaded reception onto a threaded shaft of the tack from the opposing side of the adjacent bone. The sleeve further has a head with an anti-loosening feature or anti-loosening features such as, but not limited to, tangs and/or cutouts, that engage the bone to help prevent the sleeve from working loose and/or unthreading from the bone/tack.

In such embodiments, the tack may include a head with a central, threaded shaft and a rough or projection-laden tendon contact surface situated on the side of the shaft that presses against the soft tissue (e.g., tendon) to secure the soft tissue to the adjacent bone. The tack may further include a threaded hole at its bottom that allows the tack to be threaded onto an instrument to aid in installation. The threaded shaft may extend from a cylindrical shank and have a diameter that is (but not necessarily) greater than the diameter of the threaded shaft, the transition between the cylindrical shank and the threaded shaft defining an angled surface. The threaded shaft may have (but not necessarily) a generally planar upper surface (however, other configurations, such as but not limited to conical or pointed, may equally be employed).

The sleeve may include a tubular body with a head at one end and may be (but not necessarily) configured for instrument aided threading onto the threaded shaft of the tack, the head having one or more anti bone loosening features (anti-loosening features) that grip the bone to help prevent the sleeve from loosening from the bone and/or unthreading from the tack. In one form, the head may include radially extending anti-loosening tangs defining pockets for gripping the bone, and an interior that is at least partially threaded to threadedly engage the threaded shaft of the tack. The interior may include (but not necessarily) headroom distal to the threaded interior portion to accommodate bones of varying heights while using the same size tack.

In some embodiments of the method provided herein that utilize a retention device as described above, the shaft may be pushed and/or threaded through a soft tissue (e.g., a flexor digitorum longus tendon) after a through hole has been formed therein (e.g., after being pierced with a scalpel), and into an adjacent bone (e.g., phalange) after a through hole has been formed therein as well. The relative soft tissue-bone position and/or orientation may be manually adjusted (e.g., a toe deformity may be manually corrected) which may tension the soft tissue. Once the soft tissue and bone are appropriately or preferably positioned and/or orientated relative to each other, the sleeve may be threaded into the through hole of the bone, and threaded onto the threaded shaft of the tack until the soft tissue is appropriately compressed against the bone and retained with the bone.

In some embodiments, the devices, implants and systems of the present disclosure comprise a first component or member and a second component or member, the nomenclature first and second being arbitrary. The first component may be considered a tack member that directly couples with the soft tissue, while the second component may be considered an anchor member that directly couples with the bone. The tack member includes a head portion configured for press-fit or instrument aided reception into the soft tissue (and potentially adjacent bone) to retain the soft tissue against the adjacent bone. The head portion of the tack member may include a plurality of through apertures which allow the soft tissue to extend therein/therethrough when the device is tightened to the bone and soft tissue to exsanguinate and securely grip/couple the soft tissue. The anchor member also includes a head portion configured for press-fit or instrument aided reception into the bone. The head portion of the anchor member includes an anti-loosening feature or anti-loosening features such as, but not limited to, teeth, tangs and/or cutouts, that engage the bone to prevent the anchor member from backing out or working loose of the bone. The tack and anchor members each also include a stem portion that extend into an aperture extending through the bone and threadably mate/couple therein. The stem portion of the tack and anchor members may be central or centered on the head portion thereof. The tack and anchor members can thereby be introduced into the aperture of the bone from opposing sides One of the stem portions of the tack or anchor members comprises an externally threaded male component, and the stem portion of the other of the tack or anchor members comprises an internally threaded female component. The head and stem portions of both of the tack member and the anchor member are cannulated (such that the device/implant/system is cannulated as a whole) to allow the instrumentation to extend through in situ.

In broad terms, in some embodiments, the soft tissue retention devices, implants and systems comprise a headed tack member having a rough surface on the head portion surrounding a threaded shaft portion to engage soft tissue and extend into an aperture of a bone from a first side of the bone, and a headed anchor member having a rough surface on the head portion surrounding a threaded shaft portion to engage the bone and extend into the aperture of the bone from a second side of the bone, the threaded shaft portions configured to threadably mate/couple within the aperture of the bone retain or fix the soft tissue to the bone. In some such embodiments, the head and shaft portions of both the tack and anchor members is cannulated to allow instrumentation to extend through in situ. In some other such embodiments, the head and/or shaft portions of at least one of the tack and anchor members is not cannulated.

The threaded shafts of the tack and anchor members allow for length or height adjustability of the retention device formed thereby to accommodate a range of differing bone thicknesses or heights. Further, in some embodiments, a soft tissue retention system or kit may include a plurality of tack members and/or a plurality of anchor members. The plurality of tack members and/or anchor members may differ from each other in the axial lengths of the shaft portions thereof. In this way, the system or kit may provide for a plurality of differing soft tissue retention devices each comprising one tack member and one anchor member that differ in their lengths or heights between the head portions thereof to accommodate a range of differing bone thicknesses or heights. For example, a particular tack member and/or anchor member may be selected from a plurality thereof of differing heights or lengths to suit the thickness or height of a particular bone to retain/fix a soft tissue thereto.

In one aspect, the present disclosure provides a device for retaining a tendon onto an associated bone. The device comprises a first component configured for insertion into and through a tendon and into an associated bone, the first component having a base defining a sloped upper side and a lower side, texturing on the sloped upper side of the base, a shank of a first diameter extending from the upper side of the base and having an upper end distal to the base, and an externally threaded shaft extending from the upper end of the shank and having a second diameter that is less than the first diameter of the shank. The device further comprises a second component configured for insertion into and through the associated bone and onto the first component, the second component having a tubular body defining a first end and a second end, an internally threaded bore extending into the tubular body from the first end thereof and sized to threadedly engage the externally threaded shaft of the first component, and a head on the second end of the tubular body, the head having non-threaded bone engagement features that allow the second component to be threadedly received onto the first component but disallow disengagement of the second component from the first component.

In some embodiments, the non-threaded bone engagement features comprise a plurality of tangs radially extending from a periphery of the head and defining a plurality of pockets between the tangs. In some embodiments, the texturing on the sloped upper side of the base comprises a plurality of projections. In some embodiments, the device further comprises a configured bore in an upper surface of the head of the second component. In some embodiments, the device further comprises an angled transition disposed between the upper end of the shank and the externally threaded shaft. In some embodiments, the shank and externally threaded shaft of the first component are cylindrical, and the tubular body of the second component is cylindrical. In some embodiments, an upper end of the externally threaded shaft of the first component is planar. In some embodiments, the device further comprises an internally threaded hole on the lower side of the base.

In another aspect, the present disclosure provides a device for securing soft-tissue to a bone comprising a tack and a sleeve. The tack is configured for insertion into and through a portion of soft tissue and into a portion of a bone, the tack having a round base defining a sloped upper side and a planar lower side, texturing on the sloped upper side of the rounded base, a shank of a first diameter extending from the upper side of the rounded base and having an upper end distal to the rounded base, and an externally threaded shaft extending from the upper end of the shank and having a second diameter that is less than the first diameter of the shank. The sleeve is configured for insertion into and through the portion of the bone and onto the tack, the sleeve having a tubular body defining a first end and a second end, an internally threaded bore extending into the tubular body from the first end thereof and sized to threadedly engage the externally threaded shaft of the tack, and a head on the second end of the tubular body, the head having non-threaded bone engagement features that allow the second component to be threadedly received onto the tack but disallow disengagement of the second component from the tack.

In some embodiments, the non-threaded bone engagement features comprise a plurality of tangs radially extending from a periphery of the head and defining a plurality of pockets between the tangs. In some embodiments, the texturing on the sloped upper side of the round base comprises a plurality of projections. In some embodiments, the shank and externally threaded shaft of the tack are cylindrical, and the tubular body of the sleeve is cylindrical. In some embodiments, an upper end of the externally threaded shaft of the first component is planar.

In some embodiments, the device further comprises a configured bore in an upper surface of the head of the sleeve. In some embodiments, the device further comprises an angled transition disposed between the upper end of the shank and the externally threaded shaft. In some embodiments, the device further comprises an internally threaded hole on the lower side of the round base.

In another aspect, the present disclosure provides a method for securing a flexor digitorum longus tendon to a plantar aspect of a proximal phalangeal bone for the correction of a toe contracture. The method comprises piercing the flexor digitorum longus tendon by a sharp instrument), drilling a bore in the proximal phalangeal bone, and providing a retention device. The retention device comprises a tack configured for insertion into and through the flexor digitorum tendon and into a plantar aspect of the proximal phalangeal bone, the tack having a round base defining a sloped upper side and a planar lower side, texturing on the sloped upper side of the rounded base, a shank of a first diameter extending from the upper side of the rounded base and having an upper end distal to the rounded base, and an externally threaded shaft extending from the upper end of the shank and having a second diameter that is less than the first diameter of the shank. The retention device also comprises a sleeve configured for insertion into and through the proximal phalangeal bone and onto the tack, the sleeve having a tubular body defining a first end and a second end, an internally threaded bore extending into the tubular body from the first end thereof and sized to threadedly engage the externally threaded shaft of the tack, and a head on the second end of the tubular body, the head having non-threaded bone engagement features that allow the second component to be threadedly received onto the tack but disallow disengagement of the second component from the tack. The method further comprises pushing the externally threaded shaft of the tack through the flexor digitorum tendon, tensioning the flexor digitorum tendon, and threading the sleeve onto the threaded shaft of the tack until the flexor digitorum tendon is appropriately compressed.

In one aspect, the present disclosure provides a device for retaining soft tissue to a bone. The device comprises a first member comprising a first head portion and a first threaded shaft portion extending from an inner side of the first head portion, the first head portion and the first threaded shaft portion defining a cannulated opening that extends through the first member. The device also comprises a second member comprising a second head portion and a second threaded shaft portion extending from an inner side of the second head portion, the second head portion and the second threaded shaft portion defining a cannulated opening that extends through the second member. The inner side of the first head portion comprises a row of teeth extending about the periphery of the first head portion and a plurality of through holes positioned between the first threaded shaft portion and the row of teeth that extend to an outer side of the first head portion that opposes the inner side thereof. The outer side of the first head portion includes a first drive aperture that is non-circular in cross-section. The inner side of the second head portion comprises a row of angled teeth extending about the periphery of the second head portion and an outer side of the second head portion that opposes the inner side thereof includes a second drive aperture that is non-circular in cross-section.

In another aspect, the present disclosure provides a method for securing soft tissue to a bone. The method comprises forming an aperture in a portion of soft tissue, and forming a through aperture in a bone. The method also comprises obtaining the device for retaining soft tissue to a bone described immediately above. The method further comprises extending the first threaded shaft portion of the first member of the device through the aperture in the soft tissue and into the through aperture of the bone with the inner side of the first head portion of the device in engagement with the soft tissue. The method also comprises extending the second threaded shaft portion of the second member of the device into the through aperture of the bone with the inner side of the second head portion of the device in engagement with the bone. The method further comprises threadably coupling the first and second shaft portions together within the through aperture of the bone. The method also comprises compressing the first head member against the soft tissue and the second head member against the bone.

In another aspect, the present disclosure provides a system for securing soft tissue to a bone. The system comprises the device for retaining soft tissue to a bone described above. The system also comprises a first instrument comprising a guide wire portion extending from a first drive projection provided at an end of a handle portion, the guide wire portion being configured to extend through the cannulated openings of the first and second members of the device, and the first drive projection being configured to mate with the first drive aperture of the first head member of the first member. The system further comprises a second instrument comprising a handle portion, a second drive projection provided at an end of the handle portion, and an opening extending into the second drive projection configured to accept the guide wire portion of the first instrument therein, the second drive projection being configured to mate with the second drive aperture of the second head member of the second member. The system also comprises a sizing instrument comprising a through hole extending from a tip of the sizing instrument, a groove aligned with the through hole and a plurality of sizing markings proximate to the groove that correspond to differently sized second members of the device, the through hole and the groove being configured to accept the guide wire portion of the first instrument therein.

In another aspect, the present disclosure provides instruments and related methods of use for installing a soft tissue (e.g., tendon or ligament) retention device during a soft tissue-to-bone attachment procedure. The instrument allows multiple functions to be performed through single hand manipulation thereof. The installation instrument provides for implant gauging, implant insertion, implant compression and/or implant fixation during the attachment procedure.

In some embodiments, the installation instrument comprises a handle portion configured to allow a user to hold and manipulate the installation instrument with one hand (e.g., via extending a digit through an aperture thereof, such as a user's thumb). In some embodiments, the installation instrument comprises a gauging portion extending from one side of the handle portion configured to aid in determining (e.g., gauging) an appropriate size (e.g., length) of a soft tissue retention implant to utilize with a particular bone. In some embodiments, the installation instrument comprises an insertion and fixation portion extending from a side of the handle portion configured to selectively/temporarily engage at least a portion of the soft tissue retention implant during the insertion and attachment procedure. In some embodiments, the installation instrument allows one-handed fixation and compression of the soft tissue retention implant.

In some embodiments, the handle portion comprises a ring (i.e., annulus) sized for reception onto a thumb of the user's hand, the gauging portion comprises a rod extending radially from a boss on an outer surface area of the ring, and the insertion and fixation portion comprises a head extending radially from another outer surface area of the ring with a tip configured to selectively/temporarily engage the soft-tissue retention implant for insertion and fixation of the retention implant. In one embodiment, the tip is threaded. In some embodiments, the gauging portion is sized to receive a gauge with visual indications/demarcations in order to delineate an appropriate size of the soft tissue retention implant for the particular bone. In one embodiment, the gauging portion is situated 180 degrees from the insertion and fixation portion on the handle portion, thereby forming a double-ended instrument.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating some exemplary embodiments and are not to be construed as limiting the disclosure. The drawings may or may not be drawn to scale. Illustrative dimensions and aspects are provided in some of the figures, which may be altered as appropriate.

FIG. 77 illustrates a bottom perspective view of the shaft portion of FIG. 75;

FIG. 78 illustrates a side view of the shaft portion of FIG. 75;

FIG. 79 illustrates a top view of the shaft portion of FIG. 75;

FIG. 80 illustrates an isometric view of a head portion of the soft tissue tack member of FIG. 65;

DETAILED DESCRIPTION

Figure 1:
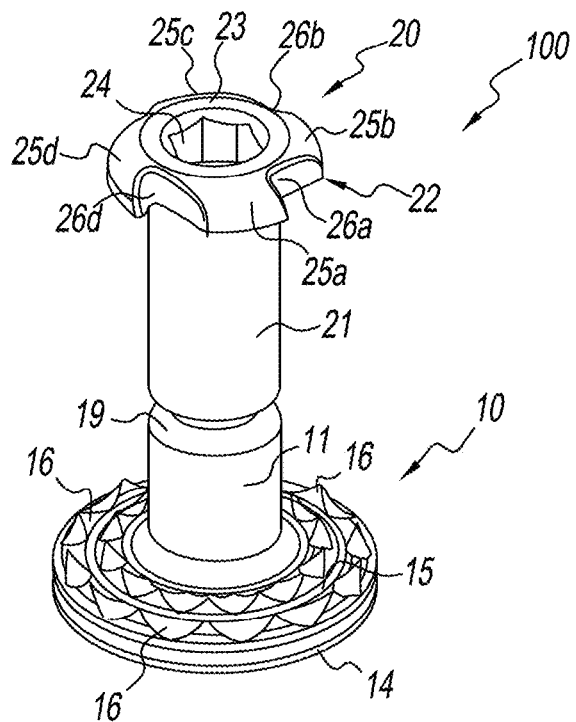
FIG. 1 is an elevational perspective view of an exemplary soft tissue retention device, in accordance with an aspect of the present disclosure.
Figure 2:
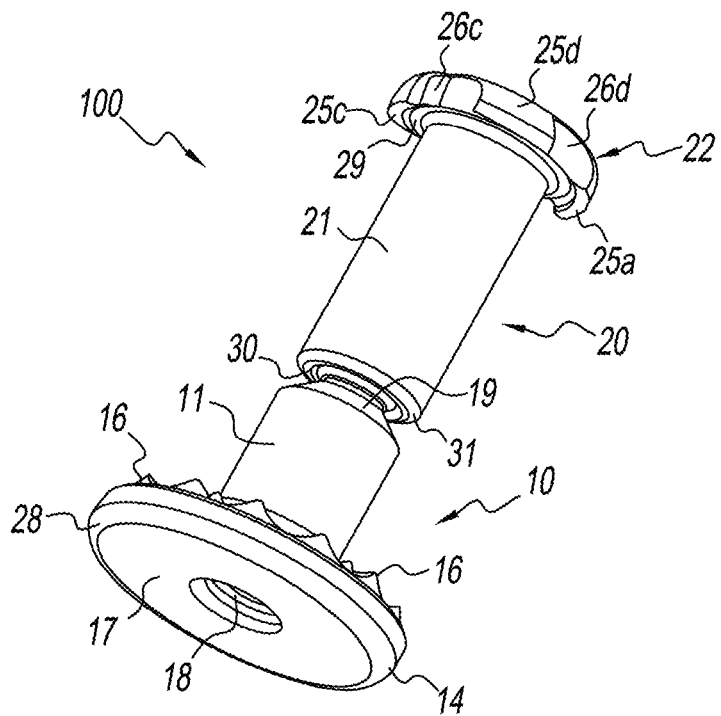
FIG. 2 is a bottom perspective view of the soft tissue retention device of FIG. 1.
Figure 3:
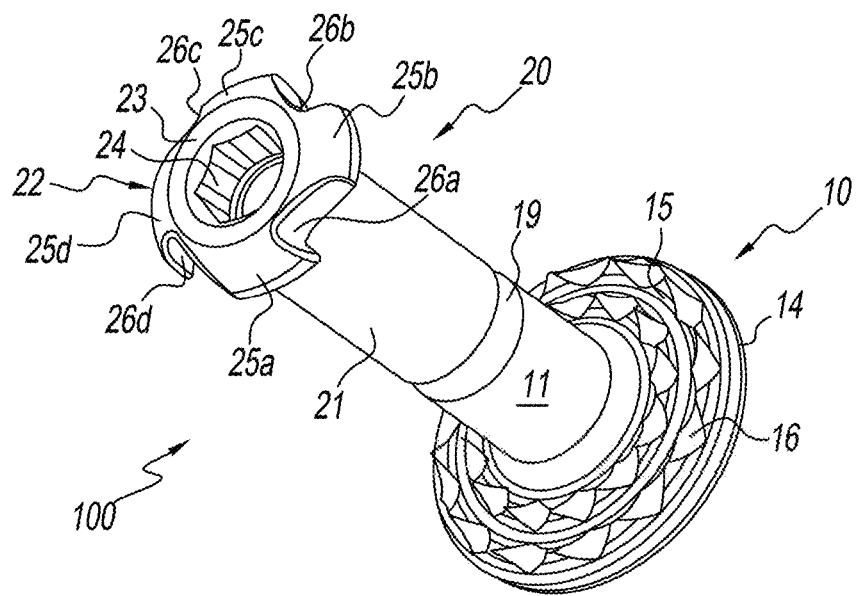
FIG. 3 is another elevational perspective view of the soft tissue retention device of FIG. 1.
Figure 4:
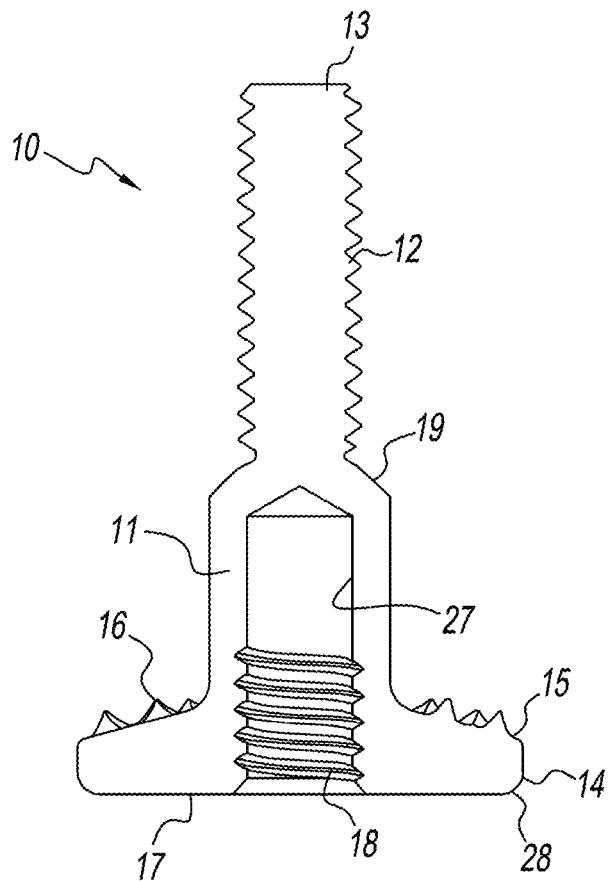
FIG. 4 is a cross-sectional side view of a tack of the soft tissue retention device of FIG. 1.
Figure 5:
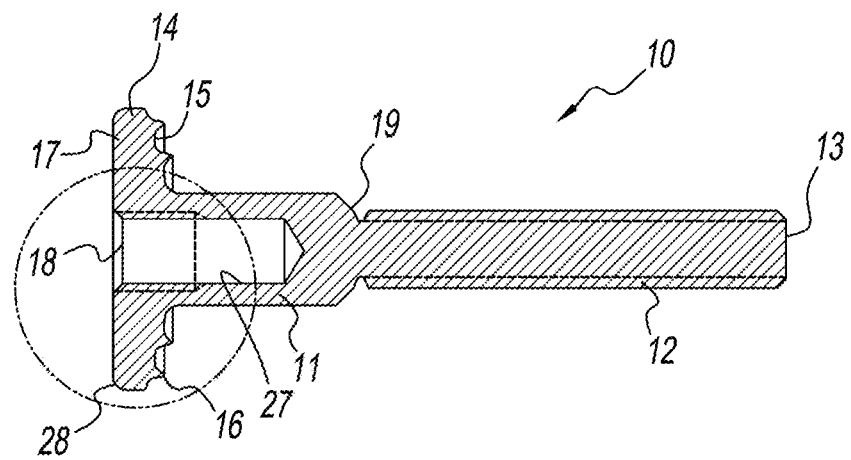
FIG. 5 is another cross-sectional view of the tack of the soft tissue retention device of FIG. 1.
Figure 6:
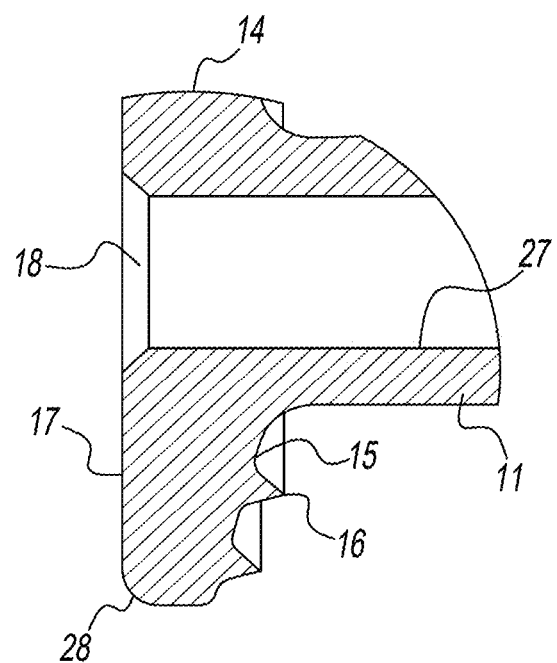
FIG. 6 is an enlarged cross-sectional view of a portion of the tack of FIG. 5 as indicated in FIG. 5.
Figure 7:
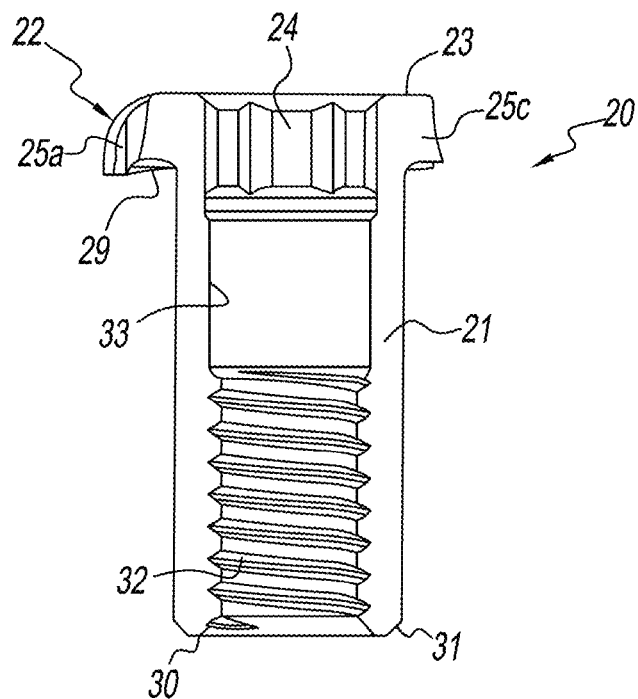
FIG. 7 is a cross-sectional side view of a sleeve of the soft tissue retention device of FIG. 1.
Figure 8:
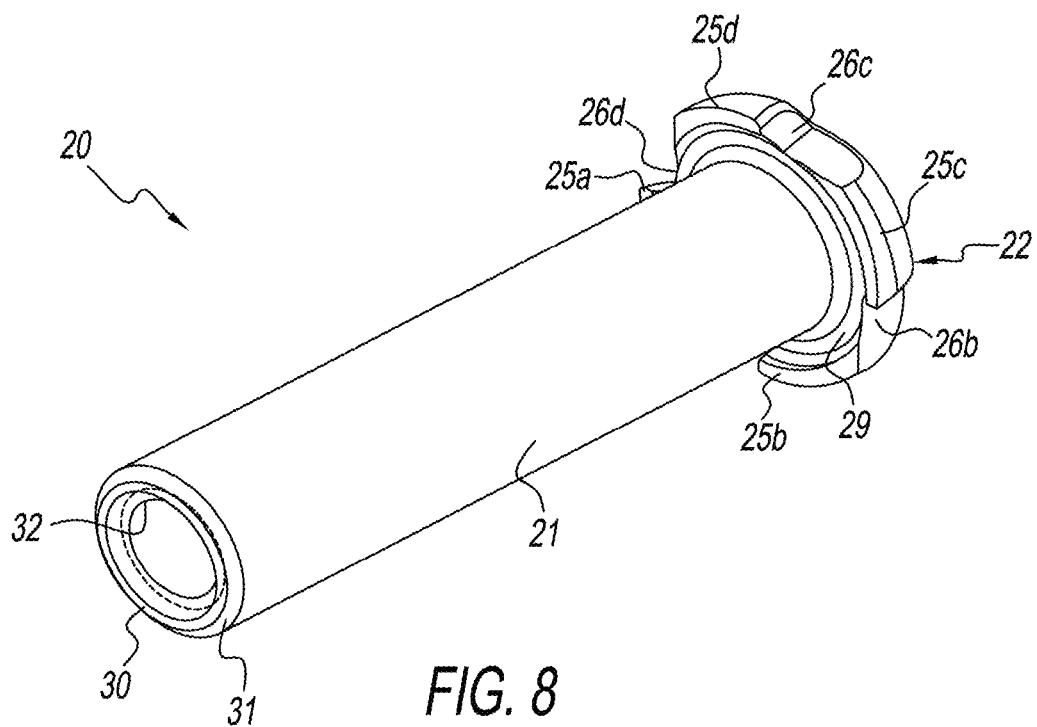
FIG. 8 is a perspective view of the sleeve of FIG. 7.
Figure 9:
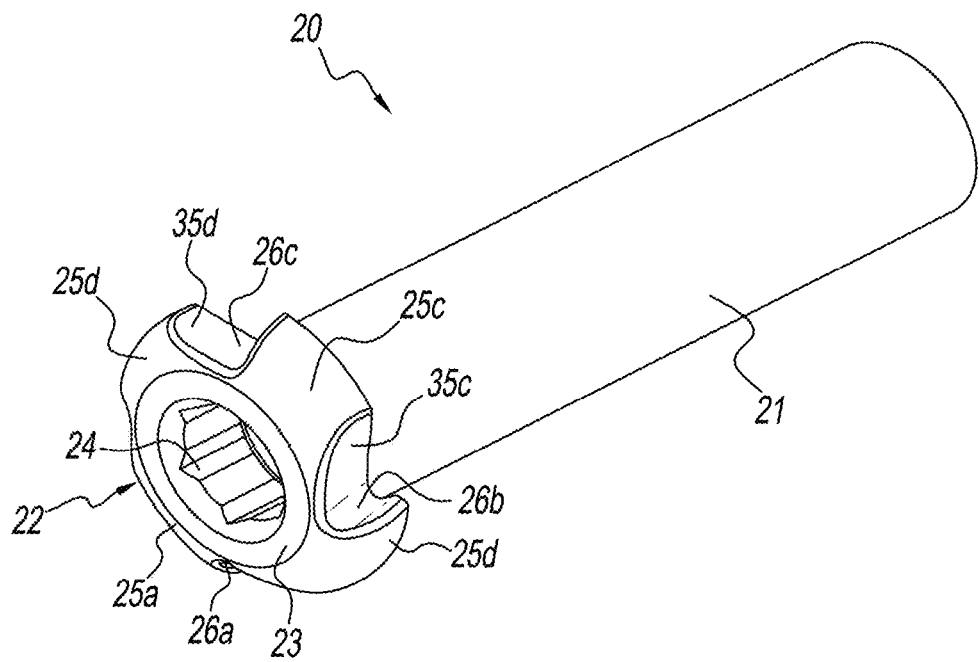
FIG. 9 is another perspective view of the sleeve of FIG. 7.
Figure 10:
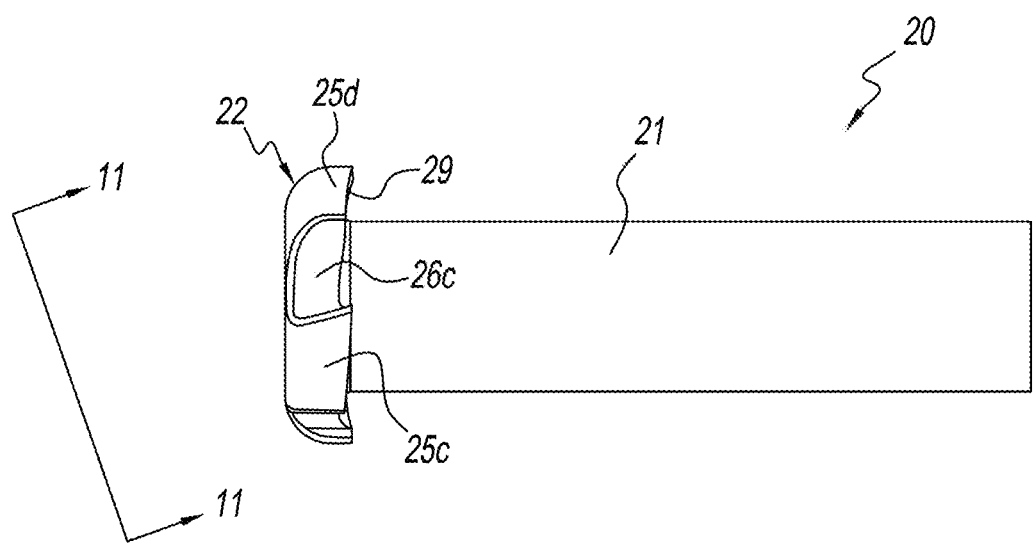
FIG. 10 is a side view of the sleeve of FIG. 7.
Figure 11:
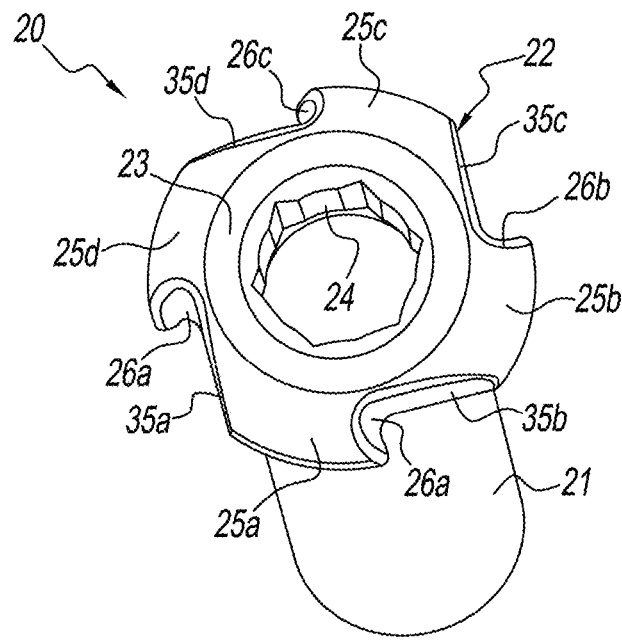
FIG. 11 is a top side view of the sleeve of FIG. 7.
Figure 12:
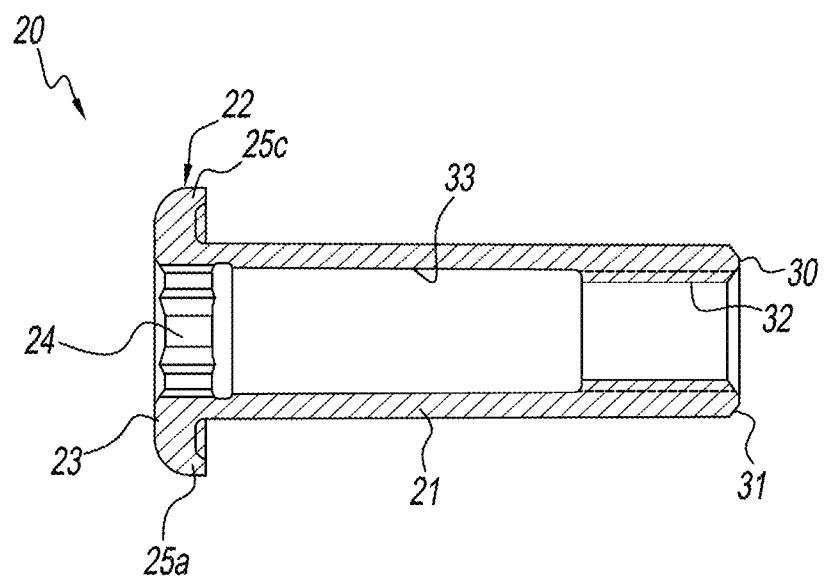
FIG. 12 is a cross-sectional side view of the sleeve of FIG. 7.
Figure 13:
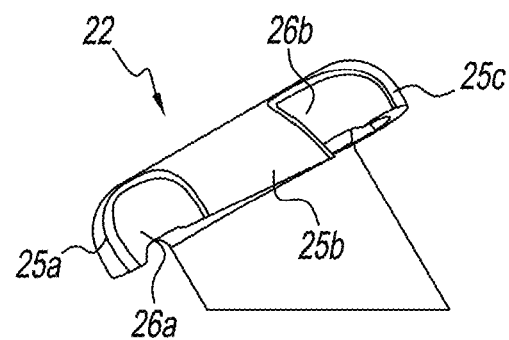
FIG. 13 is an enlarged side view of a head portion of the sleeve of FIG. 7.
Figure 14:
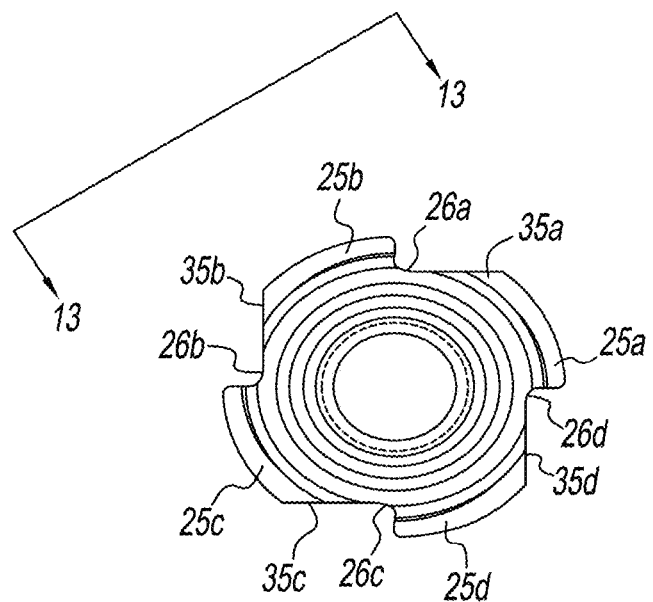
FIG. 14 is a top view of the head portion of the sleeve of FIG. 13.
Figure 15:
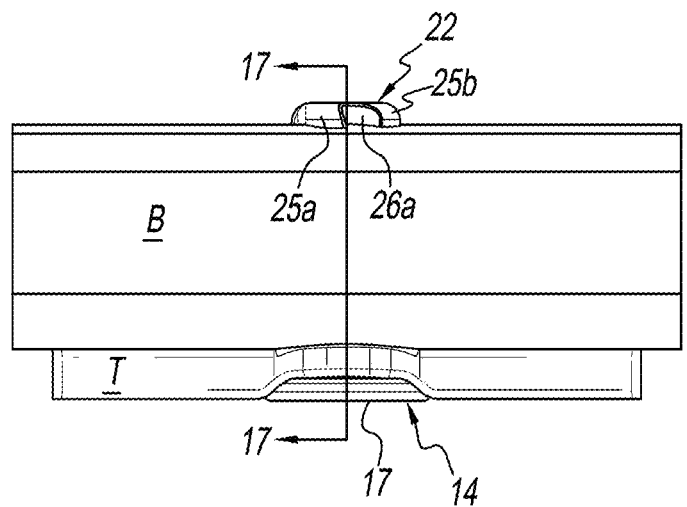
FIG. 15 is a side view of a portion of a bone and associated soft tissue secured with the soft tissue retention device of FIG. 1, in accordance with an aspect of the present disclosure.
Figure 16:
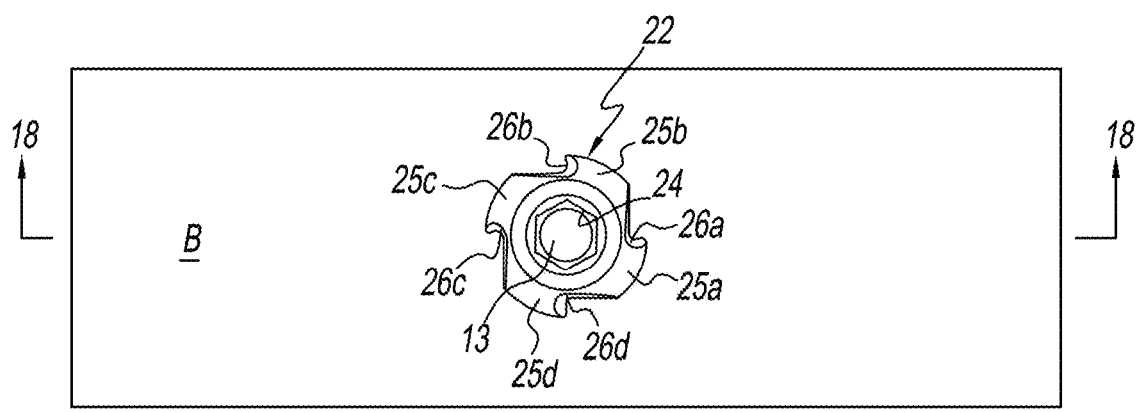
FIG. 16 is a top view of the bone, soft tissue and soft tissue retention device of FIG. 15.
Figure 17:
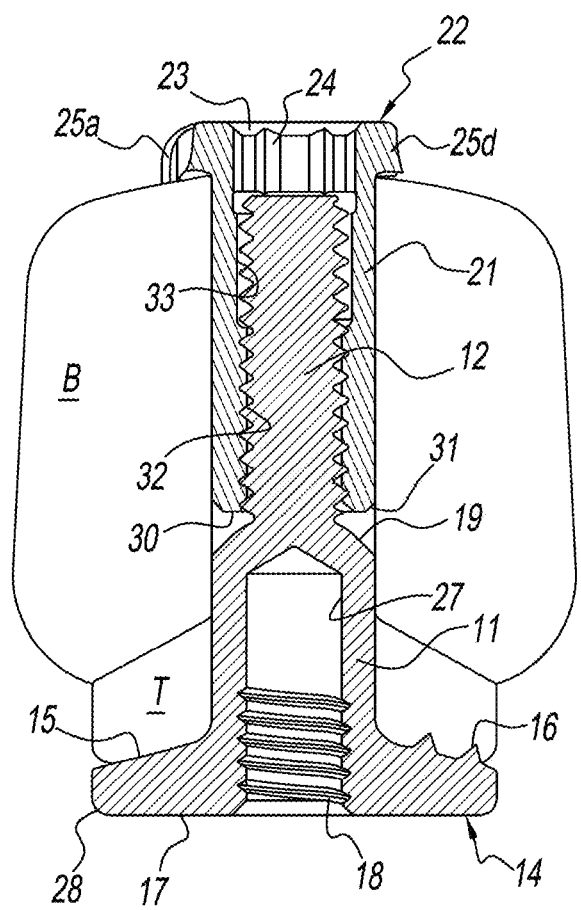
FIG. 17 is a cross-sectional view of the bone, soft tissue and soft tissue retention device of FIG. 15.
Figure 18:
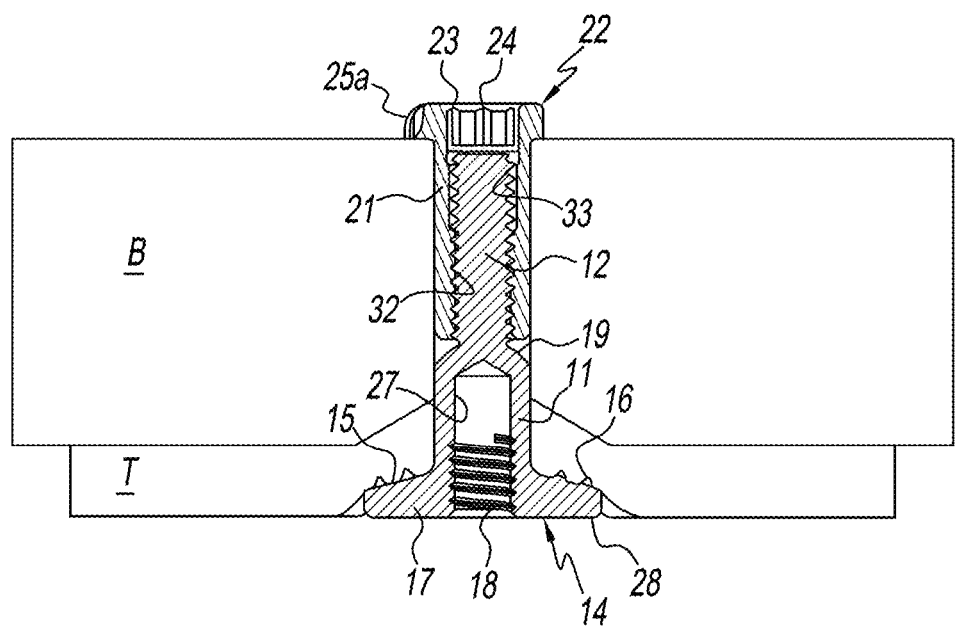
FIG. 18 is another cross-sectional view of the bone, soft tissue and soft tissue retention device of FIG. 15.

Generally stated, disclosed herein are devices, implants, instrumentation, systems and related methods for retaining or coupling soft tissue to bones. The systems, instruments and related methods may facilitate preparation of a bone to accept the devices, implants, and systems therein/therethrough, implantation/insertion of the devices, implants, and systems into the prepared bone, and/or selection of properly sized devices, implants, and systems for a particular bone.

In this detailed description and the following claims, the words proximal, distal, anterior or plantar, posterior or dorsal, medial, lateral, superior and inferior are defined by their standard usage for indicating a particular part or portion of a bone (or any other anatomical structure) or device/implant/system/instrument according to the relative disposition of the natural bone (or any other anatomical structure) or directional terms of reference. For example, "proximal" means the portion of a device/implant/system/instrument nearest the torso, while "distal" indicates the portion of the device or instrument farthest from the torso.

As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot and/or ankle, the term "dorsal" refers to the top of the foot and the term "plantar" refers the bottom of the foot.

Approximating language, as used herein throughout disclosure, may be applied to modify any quantitative representation that could permissibly vary without resulting in a change in the basic function to which it is related. Accordingly, a value modified by a term or terms, such as "about" or "substantially," is not limited to the precise value specified. For example, these terms can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%. In some instances, the approximating language may correspond to the precision of an instrument for measuring the value.

Referring to the drawings, wherein like reference numerals are used to indicate like or analogous components throughout the several views, and with particular reference to FIGS. 1-18, there is illustrated an exemplary embodiment of a soft tissue (such as, but not limited to, tendon or ligament) retention, coupling, fixation or securement device, implant or system 100 configured to couple, retain, fix, and/or secure soft tissue to an associated or desired bone (such as, but not limited to, a relatively small bone (e.g., a bone of the foot or hand)). In some embodiments, the soft tissue retention device 100 may be particularly configured and/or advantageous for retention of a flexor digitorum longus tendon and an associated bone, such as, but not limited to, the plantar aspect of a proximal phalangeal base (bone) particularly, but not necessarily, for the correction of a toe contracture. However, the soft tissue retention device 100 may be configured and/or effectively utilized to retain, couple or fix any soft tissue (e.g., a tendon, ligament or the like) to any bone (e.g., any relatively small bone, such as a phalange, metatarsal or metacarpal bone) of a patient (e.g., a human patient).

The soft tissue retention device 100 may be made of a biocompatible metal such as titanium, stainless steel, an alloy, or the like, or other biocompatible material such as plastic, ceramic or the like. The soft tissue retention device 100 may include by a first component 10 and a second component 20, the nomenclature first and second being arbitrary. The first component 10, without being restrictive, may be termed a tack, while the second component 20, without being restrictive, may be termed a sleeve 20. When implanted, the sleeve 20 is received onto the tack 10.

FIGS. 1-18 show various views of the soft tissue retention device 100 assembled, implanted with respect to a tendon T and associated/adjacent bone B, and separately—the two components, tack 10 and sleeve 20. Any dimensions, angles and/or the like depicted in the figures are illustrative and not necessarily dispositive. Other dimensions, angles and/or the like can be used and are contemplated.

The tack 10 may include a generally disk-shaped base 14, although other shapes may be used, having a generally planar upper side, face or surface 17 and a sloped or angled lower side, face or surface 15, the nomenclature upper and lower being arbitrary. An internally threaded bore, hole, cavity or depression 18 is formed in the upper side 17. The threaded bore 18 is configured to receive a like threaded instrument or tool (not shown) for inserting or aiding in the insertion, installation or implantation of the tack 10 into a tendon and bone.

The tack 10 further includes a shank or the like 11 that extends generally transverse from the lower side 15 of the head 14. The shank 11 has a first diameter. A threaded shaft 12 with a blunt end 13 extends from the shank 11, the threaded shaft 12 having a second diameter (including the external threading) that is less than the first diameter of the shank 11. As shown in FIGS. 2, 4, 5, 1 and 18, the threaded shaft 12 may be externally threaded. In alternative embodiments, the threaded shaft 12 may include an internally threaded aperture that extends partially or entirely through the shaft 12 (and potentially the head 14).

An angled portion 19 may be provided at the transition between the shank 11 and threaded shaft 12, i.e. as a transition between the larger diameter section comprising the shank 11 and the smaller diameter section comprising the threaded shaft 12.

The lower side 15 of the head 14 may include a rough, coarse, bumpy, or textured (collectively, textured) surface, shown as a plurality of bumps, protrusions, spikes or the like (collectively, protrusions) 16 situated about the lower side 15. Other types of textured surfaces may be used including coatings, treatments or otherwise. Moreover, while the protrusions 16 are situated in two rings about the shank 11, other patterns or no patters of protrusions 16 may be used.

The sleeve 20 may include a generally tubular body 21 having a cap, head or top (head) 22 with a generally planar upper surface 23. A socket 24 is provided in the head 22 that is configured to receive a like configured installation tool or instrument (not shown). While the socket 24 is shown as hexagonal, other configurations may be used. The head 22 has one or more anti-loosening features. To this end a plurality of tangs 25a-d radially project from the outer periphery of the head 22. The tangs 25a-d define a plurality of pockets or cutouts 26a-d with a pocket 26 between each tang 25. Each tang 25a-d has a respective flat 35a-d and is generally circumferentially arced in a counterclockwise direction relative to a top view thereof. The configuration of the tangs 25a-d, pockets 26a-d, and flats 35a-d allows generally unrestricted rotation of the head 22 relative to the bone during clockwise threaded rotational installation of the sleeve 20 onto the tack 10 (as view from the top thereof), but provides restricted counterclockwise rotational movement of the head 22 (as view from the top thereof) through gripping of the bone by the head anti-loosening structure (tangs, pockets and/or flats) should the sleeve 20 undergo de-threading or loosening from the tack 10. The cap 22 also defines an undersurface or overhang 29 that may be configured to aid in the anti-loosening feature(s).

The tubular body 21 may include an interior bore that extends from the socket 24 to a lower opening 32 at a bottom 30 of the tubular body 21. The lower opening 32 may be threaded complementary to the external threading of the threaded shaft 12 of the tack 10 such that the sleeve 20 can be threadedly received on the tack 10. An upper portion 33 of the bore 28 axially between the socket 24 and the threaded opening 32 may be unthreaded. The length of the upper portion 33 may allow the sleeve 20 to accommodate various sizes of bones. The outer circumference of the bottom 30 may have a taper 31.

FIGS. 15-18 show several views of the soft tissue retention device 100 of FIGS. 1-14 implanted or installed into a bone B and associated tendon T in order to affix, secure or hold the tendon T to/onto the bone B. The tack 10 and the sleeve 20 are made in a variety of sizes to retain, affix, secure or hold various sized tendons to various sized bones to accommodate a range of anatomical sizes. Thus, varying height of bones can be accommodated by various "sizes" of the first component 10 and/or the second component 20.

For example, in an exemplary "size 1" soft tissue retention device, a minimal bone height (e.g., 6.75 mm) may be accomplished by threading the sleeve 20 completely onto the threaded shaft 12 of the tack 10 such that the end of the sleeve 20 bottoms out on the taper (ledge) 19 of the tack 10 between the shank 11 and the threaded shaft 12. A maximum bone height (e.g., 8.50 mm) may be accomplished by threading the sleeve 20 partially onto the threaded shaft 12 of the tack 10. An exemplary "size 2" soft tissue retention device may be used with a minimal bone height (e.g., 8.60 mm) by threading the sleeve 20 completely onto the threaded shaft 12 of the tack 10 such that the end of the sleeve 20 bottoms out on the taper (ledge) 19 of the tack 10 between the shank 11 and the threaded shaft 12. A maximum bone height (e.g., 11.50 mm) may be accomplished by threading the sleeve 20 partially onto the threaded shaft 12 of the tack 10. An exemplary "size 3" soft tissue retention device may be used with a minimal bone height (e.g., 11.6 mm) by threading the sleeve 20 completely onto the threaded shaft 12 of the tack 10 such that the end of the sleeve 20 bottoms out on the taper (ledge) 19 of the tack 10 between the shank 11 and the threaded shaft 12. A maximum bone height (e.g., 16.5 mm) may be accomplished by threading the sleeve 20 partially onto the threaded shaft 12 of the tack 10. An exemplary "size 4" tendon fixation device consisting of a "size 4" tack 10 and a "size 3" sleeve 20 may be used with a minimal bone height (e.g., 16.6 mm) by threading the sleeve 20 completely onto the threaded shaft 12 of the tack 10 such that the end of the sleeve 20 bottoms out on the taper (ledge) 19 of the tack 10 between the shank 11 and the threaded shaft 12. A maximum bone height (e.g., 21.00 mm) may be accomplished by threading the sleeve 20 partially onto the threaded shaft 12 of the tack 10.

As can be seen from FIGS. 15-18, the soft tissue retention device 100 can be used to retain, affix, fix, secure, or otherwise hold soft tissue (e.g., a tendon, ligament, muscle, cartilage, etc.) onto/to a bone. However, in preparation of securing the soft tissue to the bone, a through hole may be made in the soft tissue (e.g., by a scalpel or other instrument), and a through hole may in the bore (e.g., via drilling). The shaft 11 of the tack 10 may translated through the hole of the soft tissue and into the hole of the bone, and the soft tissue may optionally be appropriately tensioned. The sleeve 21 of the anchor member 20 may be threadably coupled with the threaded shaft 11 of the tack 10 within the hole of the bone until the soft tissue is appropriately compressed.

FIGS. 19-25 illustrate an exemplary assembly and soft tissue retention device implantation procedure to fixedly attach, couple or retain soft tissue to a bone via a soft tissue retention device. By way of example, FIGS. 19-25 illustrate a method of use of an instrument 105 with respect to the non-cannulated (or partially-cannulated) soft tissue retention device 100 of FIGS. 1-18, and the attachment of a flexor digitorum longus tendon 104 (i.e., a soft tissue) to a plantar aspect of a proximal phalangeal base 100 (i.e., a bone). However, use of the instrument 105 is applicable to other soft tissue (e.g., tendon or ligament) to bone attachment procedures, as well as other surgical procedures. Further, the instrument 105 and assembly and soft tissue retention device implantation procedure effectuated thereby may equally or similarly be employed to a fully cannulated soft tissue retention device, such as a cannulated soft tissue retention device described below.

Figure 25:
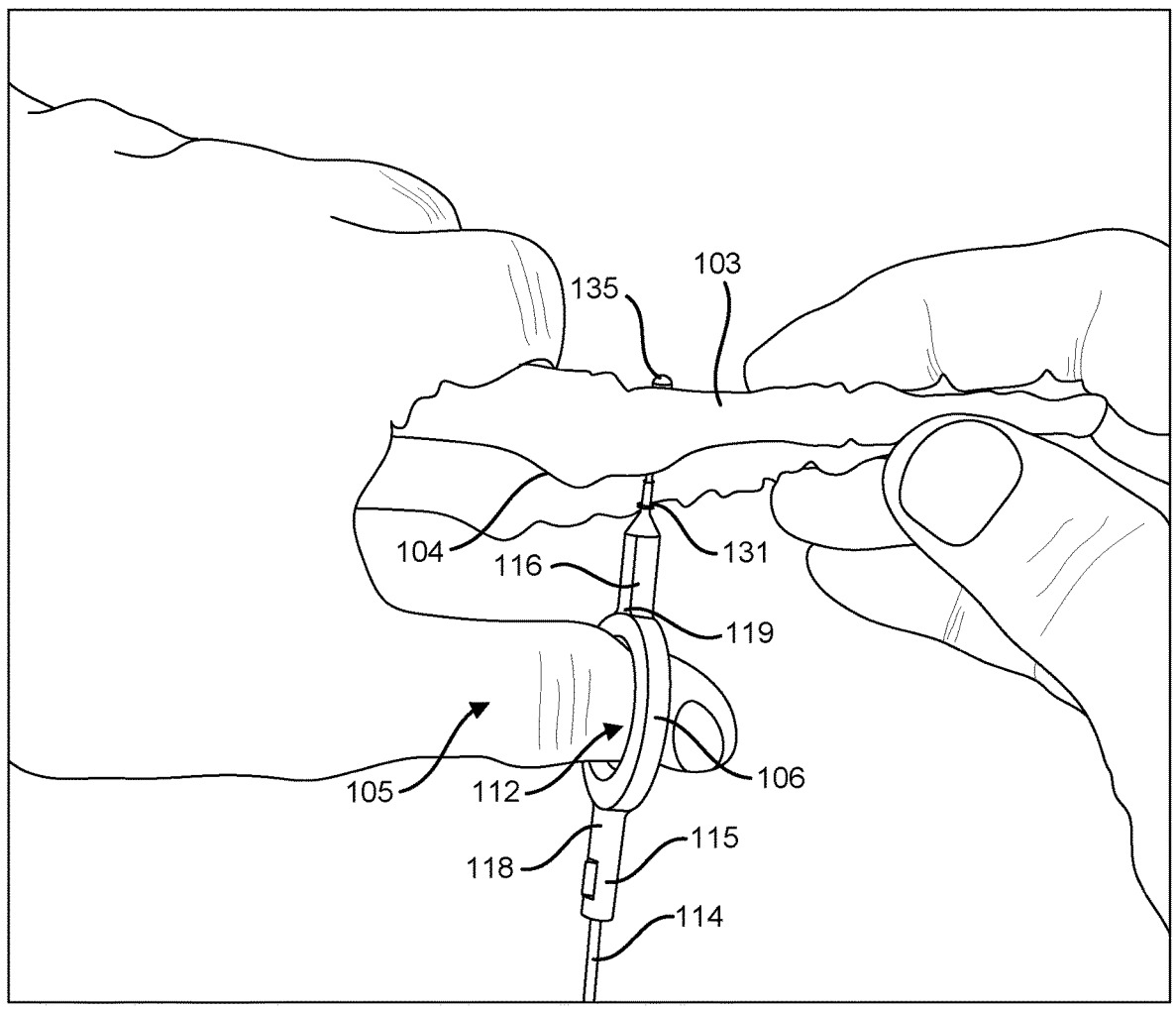
FIG. 25 illustrates a two-handed approach of implanting the soft tissue retention device of FIG. 19 utilizing the instrument of FIG. 19, in accordance with an aspect of the present disclosure.
Figure 26:
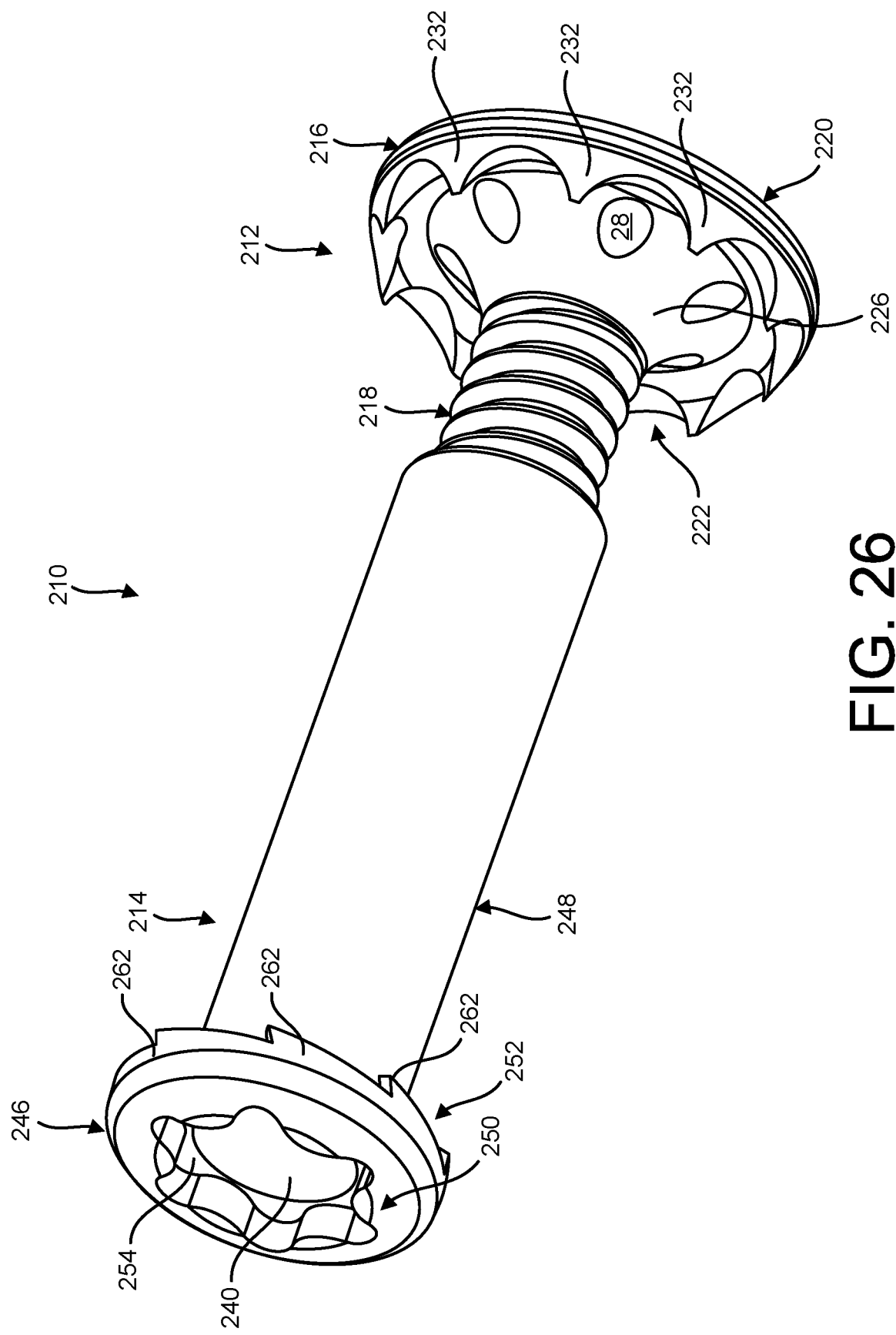
FIG. 26 illustrates a perspective view of an exemplary embodiment of a soft tissue and bone retention device or implant, in an assembled configuration, comprising a soft tissue tack member and a bone anchor member, in accordance with an aspect of the present disclosure.
Figure 27:
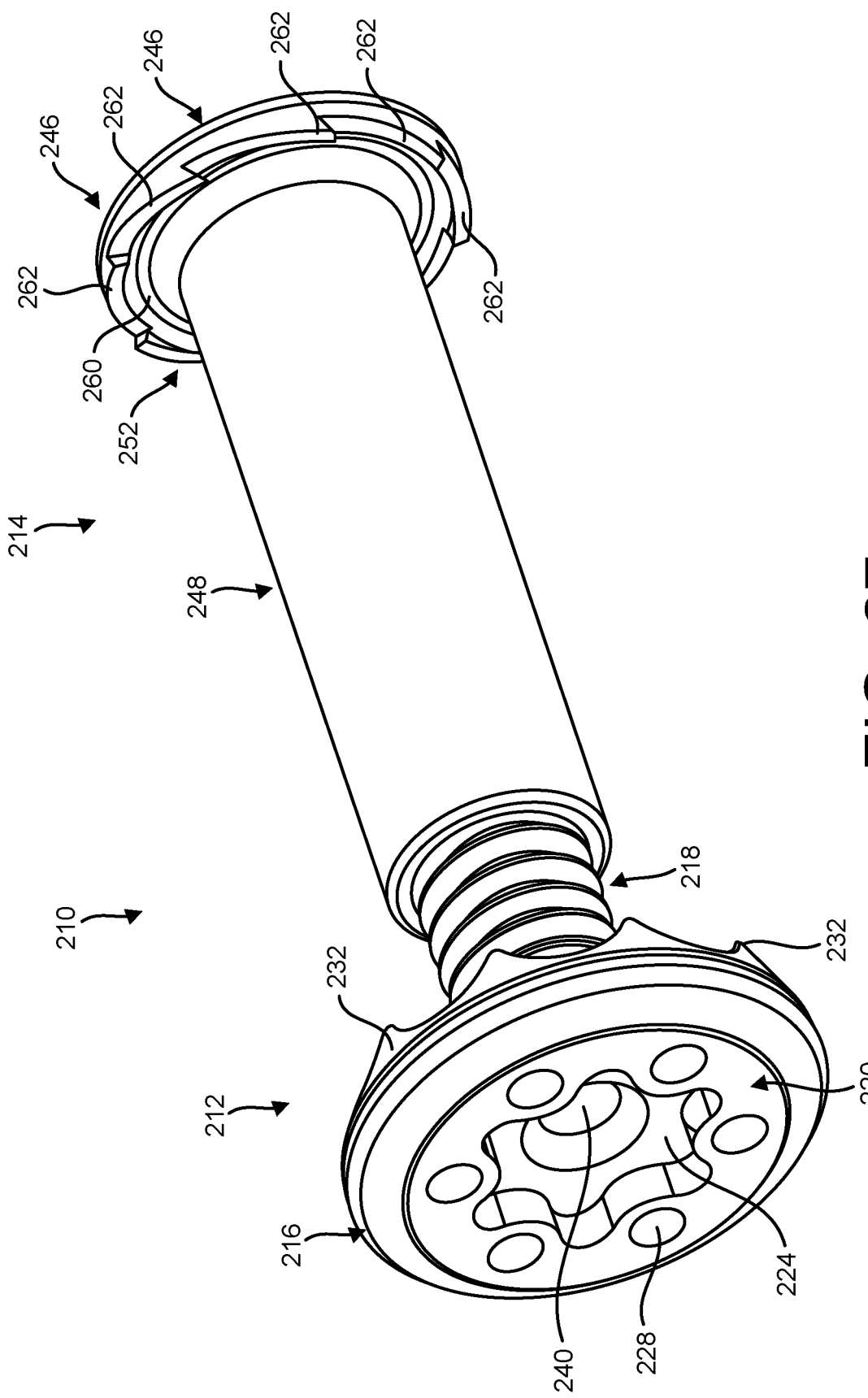
FIG. 27 illustrates another perspective view of the soft tissue and bone retention device of FIG. 1.
Figure 28:
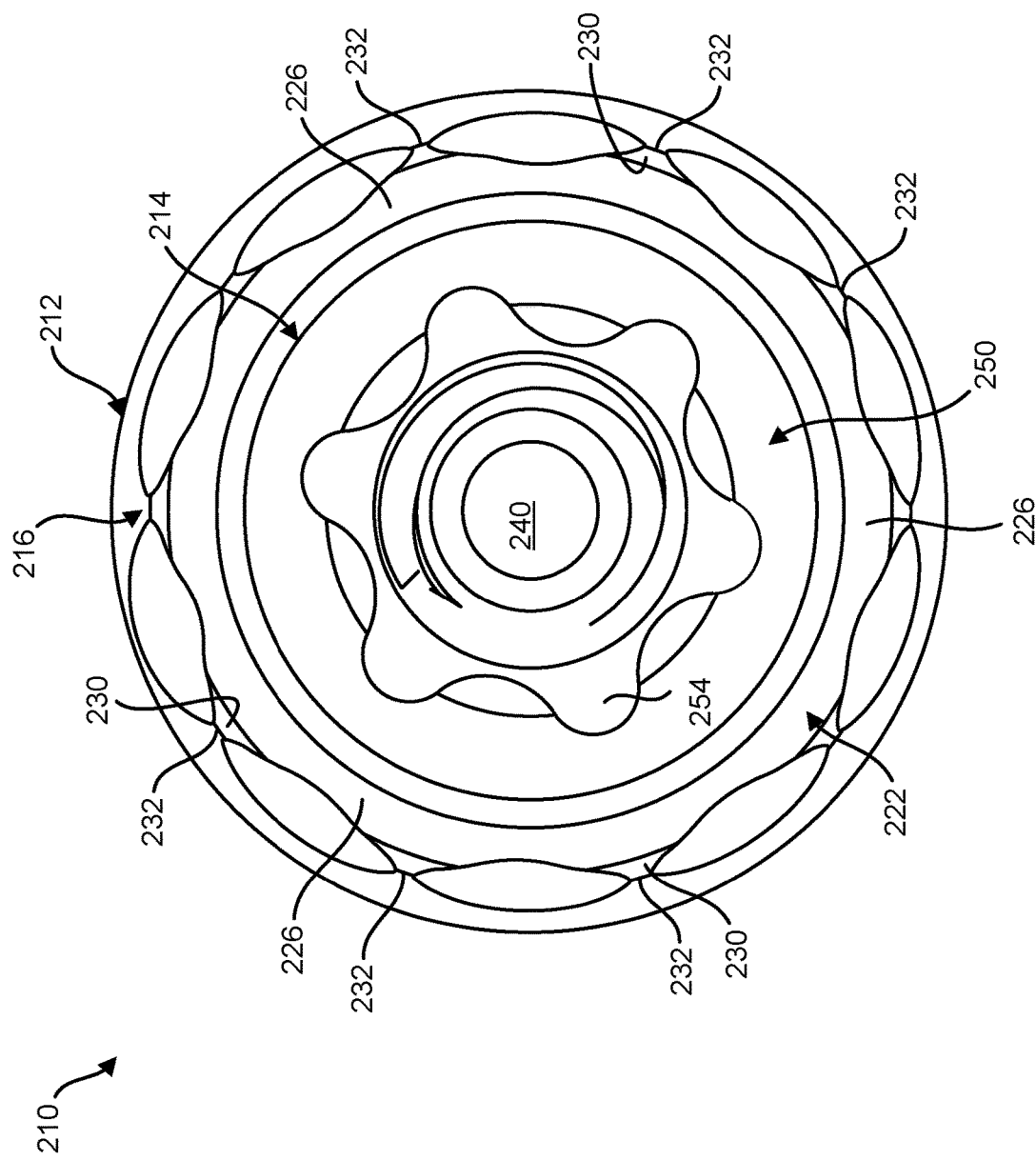
FIG. 28 illustrates a bottom view of the soft tissue and bone retention device of FIG. 1.
Figure 29:
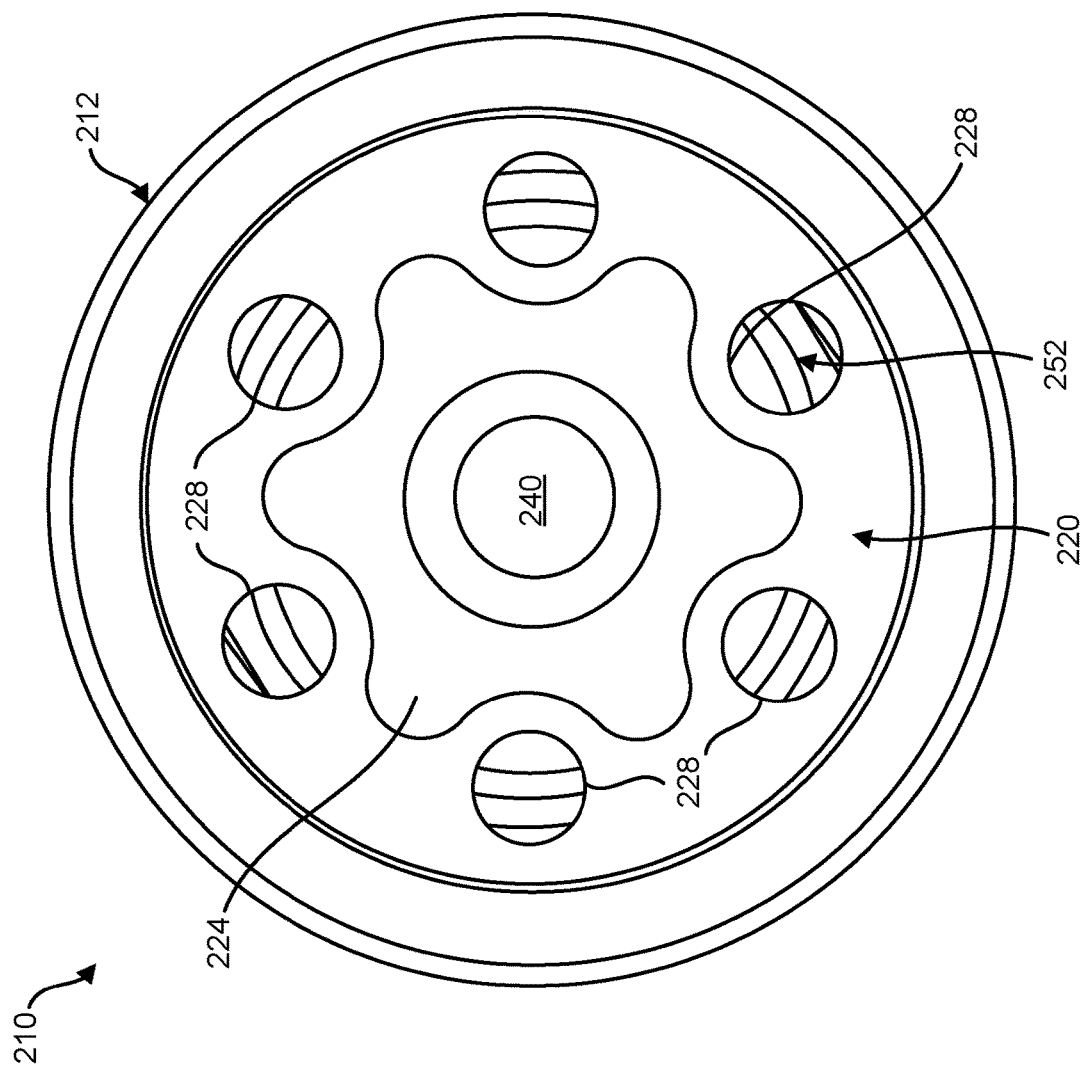
FIG. 29 illustrates a top view of the soft tissue and bone retention device of FIG. 26.
Figure 30:
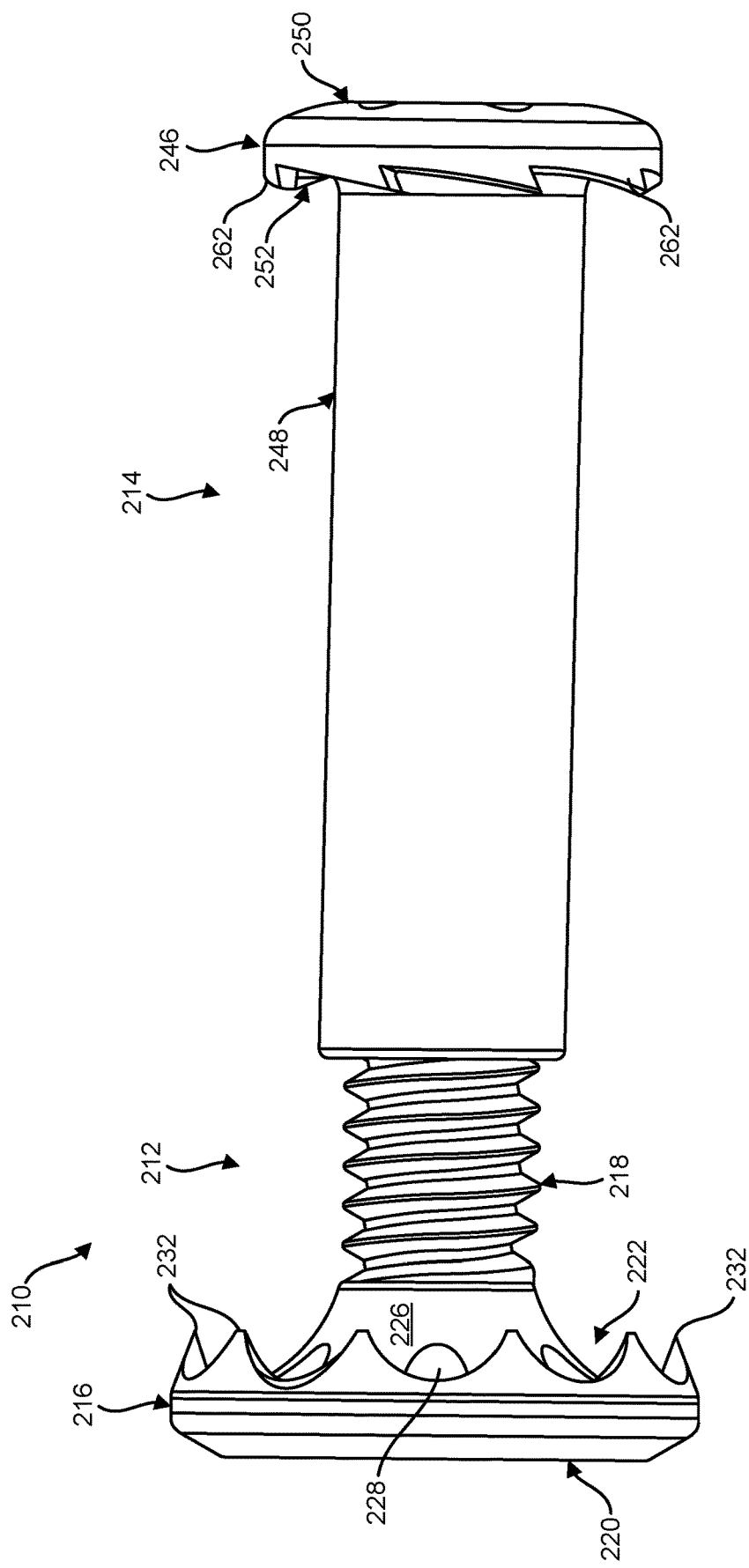
FIG. 30 illustrates a side view of the soft tissue and bone retention device of FIG. 26.
Figure 31:
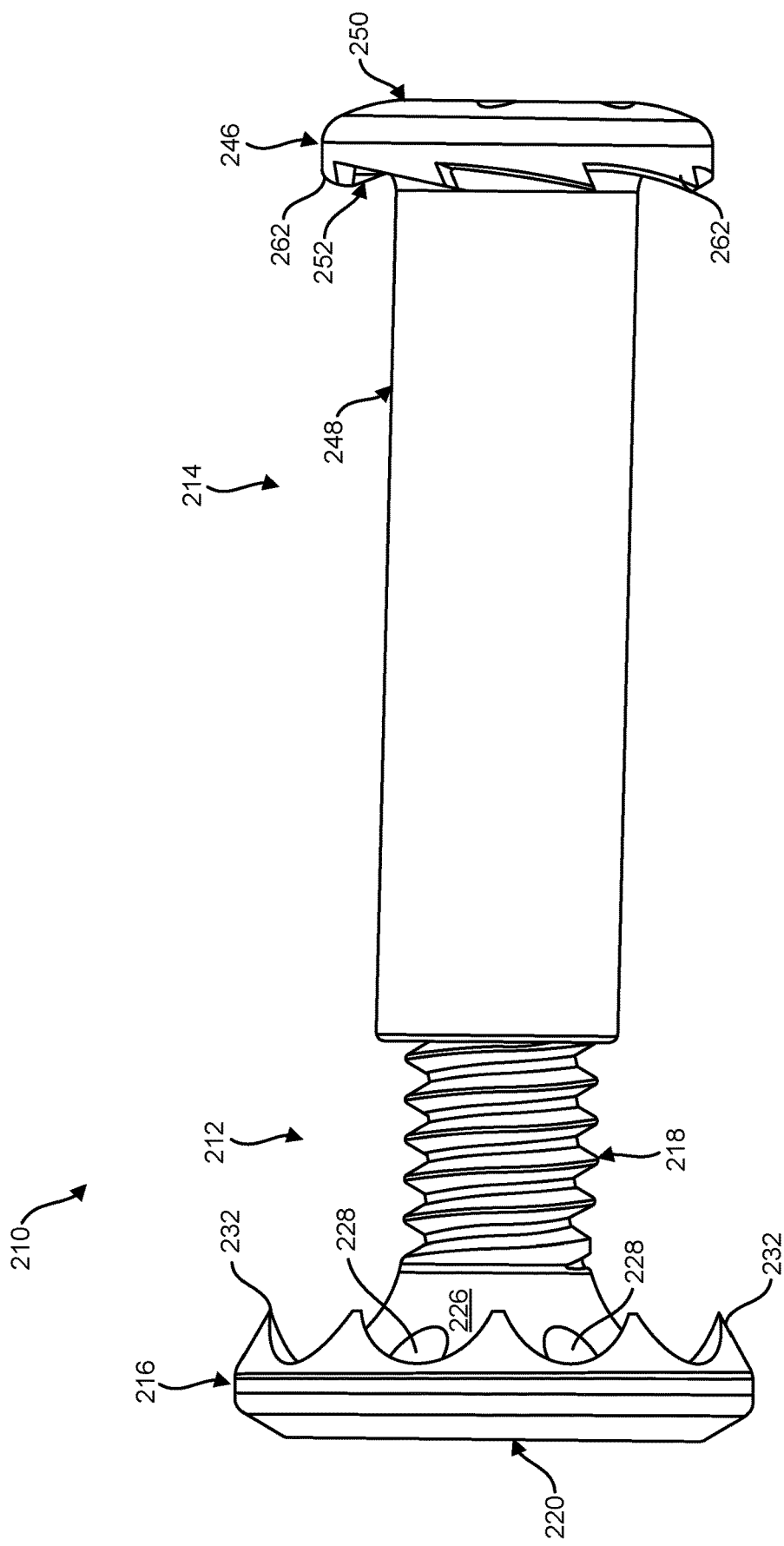
FIG. 31 illustrates another side view of the soft tissue and bone retention device of FIG. 26.
Figure 32:
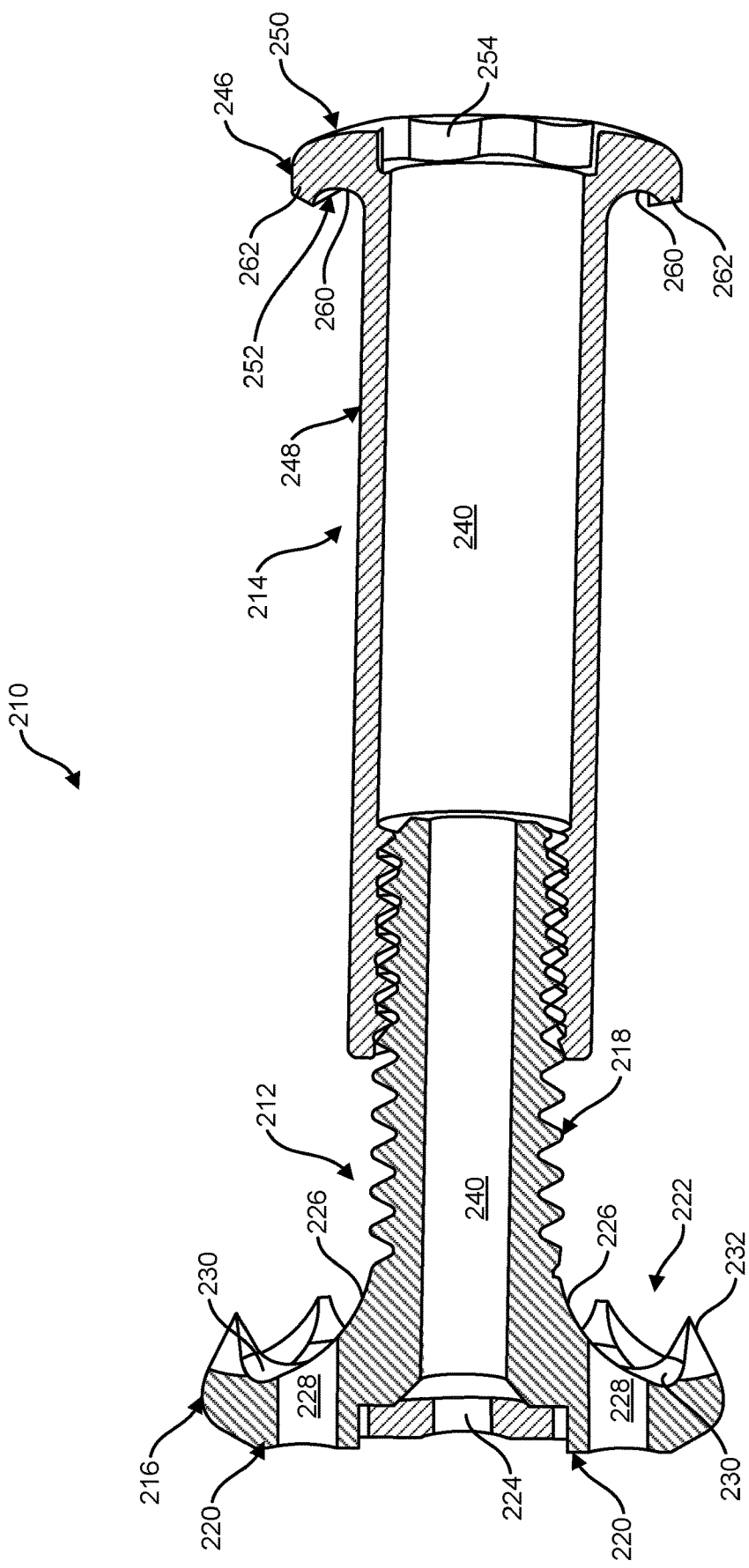
FIG. 32 illustrates a cross-sectional side view of the soft tissue and bone retention device of FIG. 26.
Figure 33:
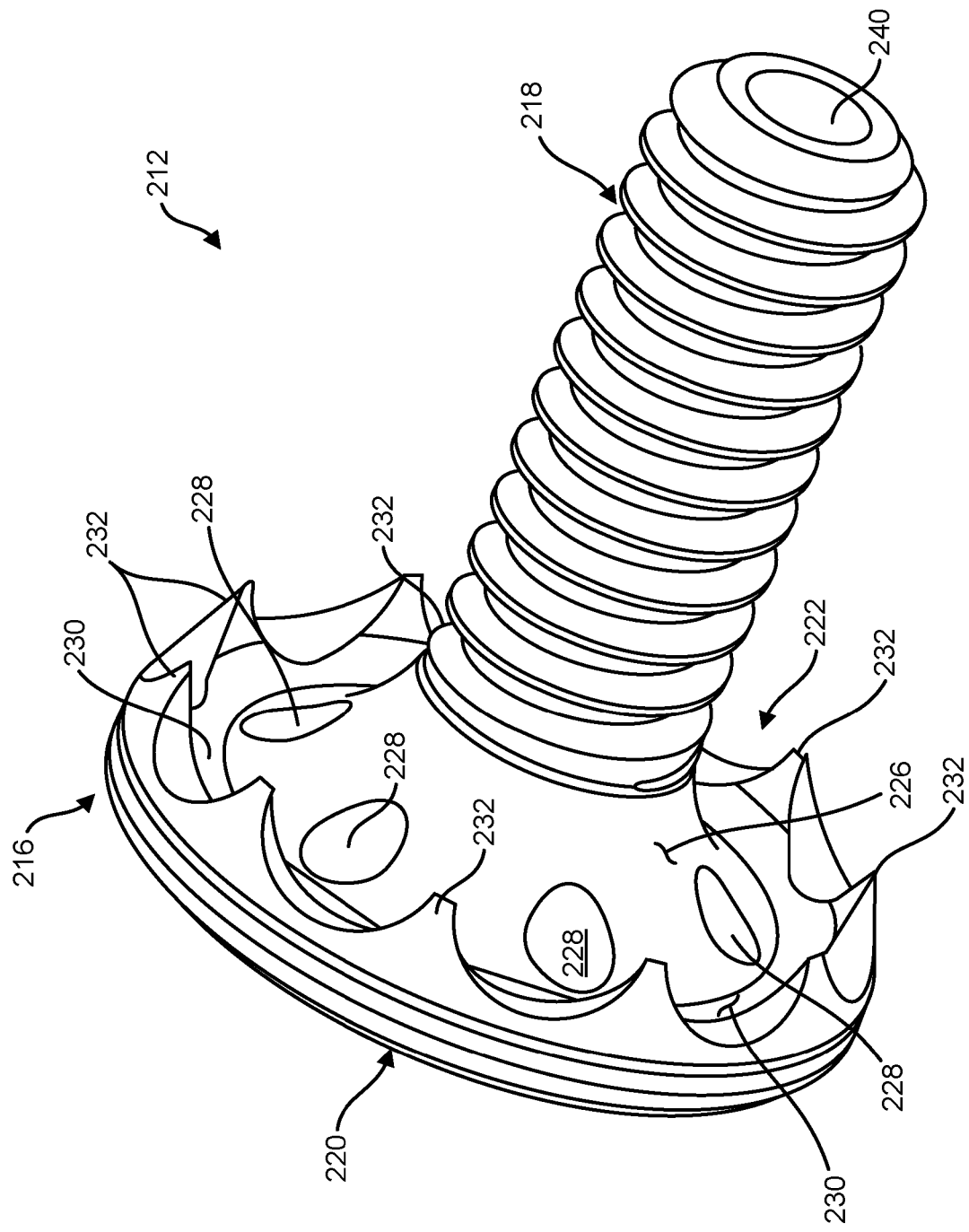
FIG. 33 illustrates a bottom perspective view of a soft tissue tack member of the soft tissue and bone retention device of FIG. 26.
Figure 34:
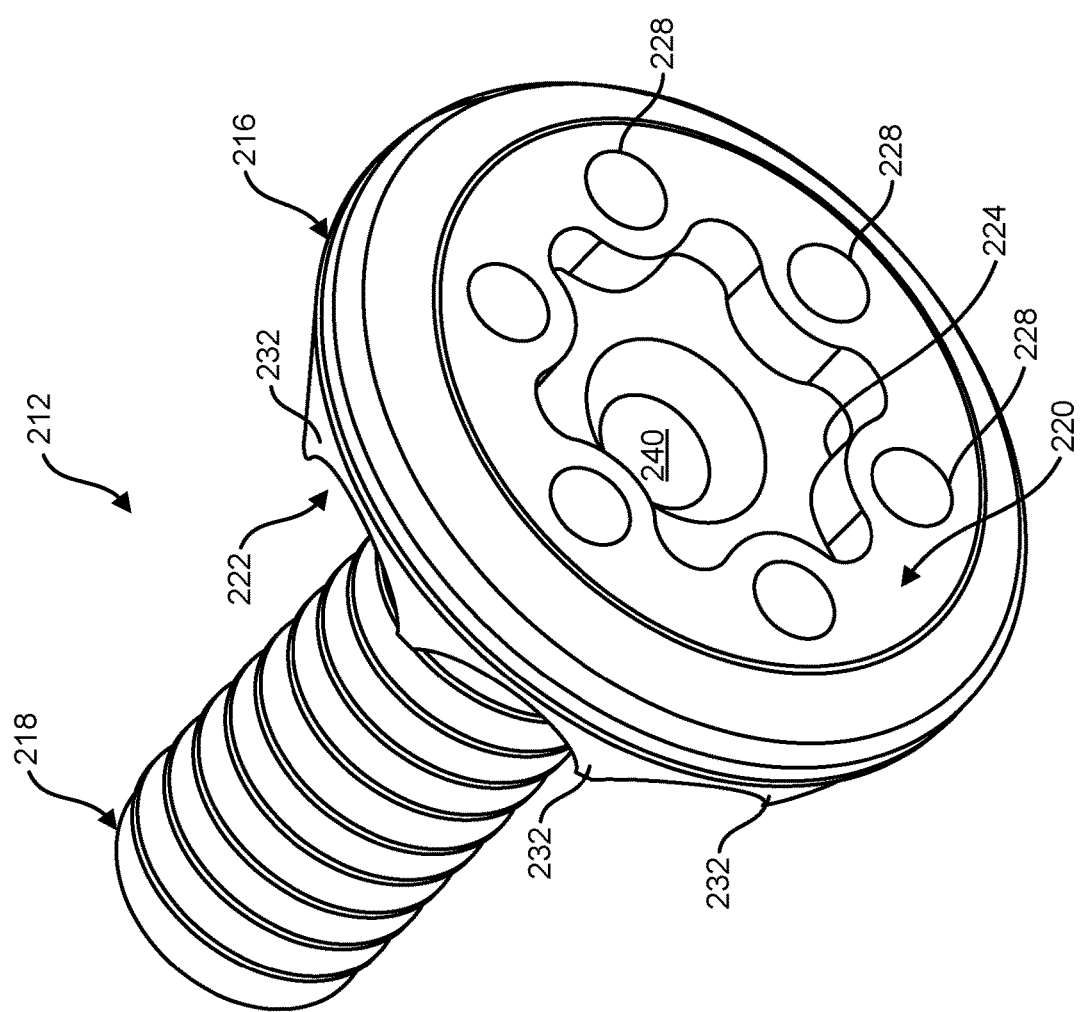
FIG. 34 illustrates an elevational perspective view of the soft tissue tack member of FIG. 34.
Figure 35:
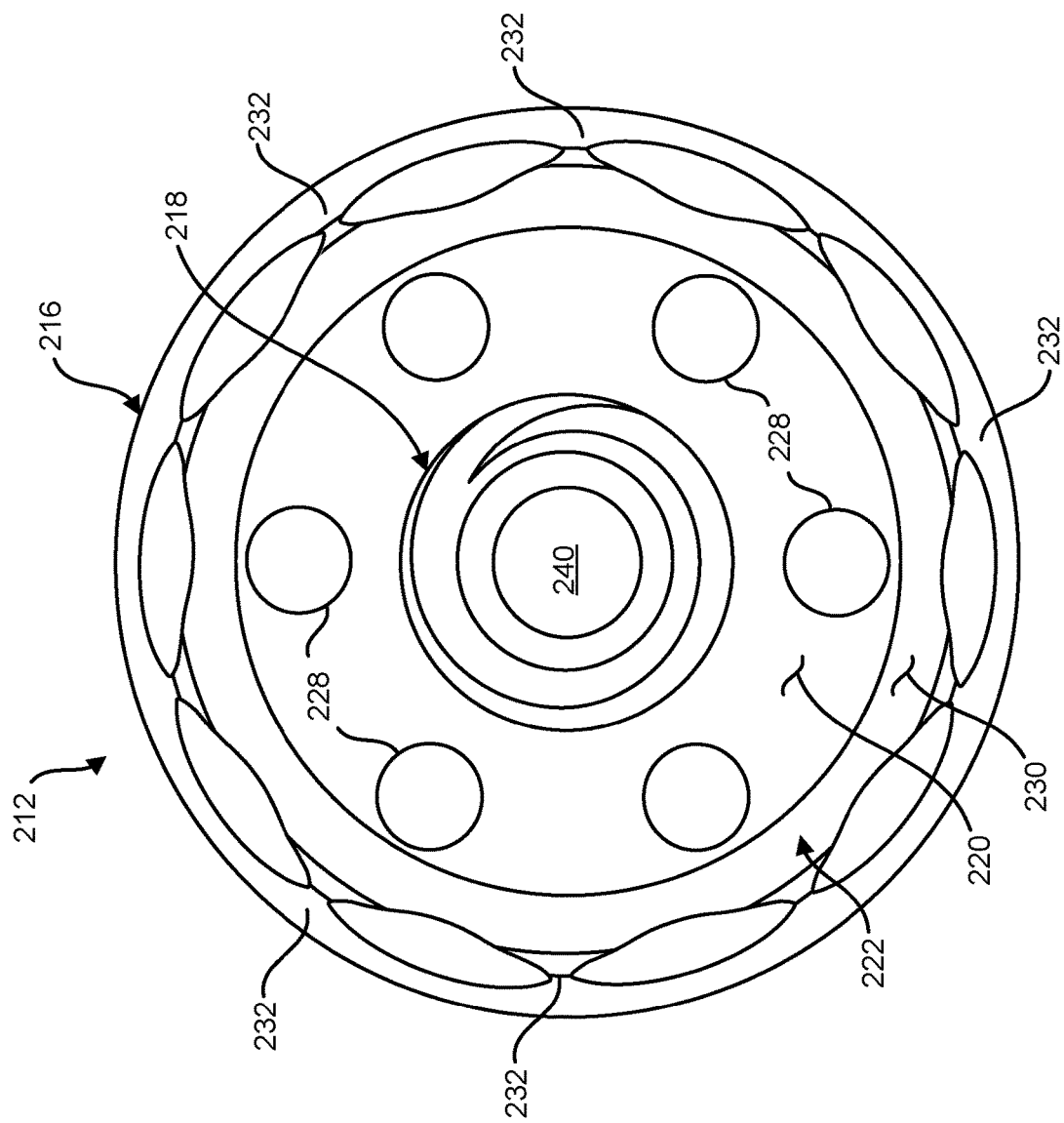
FIG. 35 illustrates a bottom view of the soft tissue tack member of FIG. 34.

FIG. 25 specifically illustrates an exemplary manner of holding the instrument 105 during the procedure by placing one's thumb into/through the aperture 112 of the handle portion 106. Rotation of the instrument 105 about the user's thumb thereby allows one handed fixation and compression of the soft tissue retention implant.

In some embodiments, the instrument 105 is made from one or more suitable surgical grade materials such as, but not limited to, stainless steel. Scaled instruments, for scaled soft tissue retention devices/implants (or portions or members thereof) and/or patient for example, are contemplated. Such scaled instruments and scaled soft tissue retention devices/implants (or portions or members thereof) may form at least part of an installation/implantation set or kit (not shown).

Generally, as shown in FIGS. 20-24, the instrument 105 and the soft tissue retention implant can be utilized to affix, fix, secure, or otherwise hold soft tissue 104 (such as, but not limited to, a tendon) onto bone 103. In preparation of securing the soft tissue 104 to the bone 103 via the soft tissue retention implant, an aperture may be made in the soft tissue (e.g., pierced by a scalpel or other instrument) and a through hole or bore 101 formed (e.g., drilled) in the bone 103. A first member/portion of the soft tissue retention implant may be engaged with the head portion 116 of the instrument 105. A portion of the first member/portion may be translated through the aperture in the soft tissue 104 and into the bone through hole 101, and the soft tissue 104 appropriately tensioned (if desired). The first member/portion of the soft tissue retention implant may be compressed/forced against the soft tissue 104 to retain the relative position/orientation of the soft tissue 104 and the bone 103, such as via the instrument 105 and the user's hand (potentially the same hand that engages the instrument 105). A second member/portion of the soft tissue retention implant may be positioned within the bone through hole 101 from an opposing side thereof as compared to the first member/portion, and engaged with a torque tool. The second member/portion may be rotated with the torque tool, and the first member/portion prevented from rotating via the instrument 105, to threadably couple the first and second members/portions and fixedly retain the soft tissue 104 to the bone 103.

As shown in FIGS. 19-25, the instrument 105 includes a handle section 106 configured to allow a user to hold and manipulate the installation instrument 105 with one hand, a gauging portion 108 extending from one side of the handle section 106, and an insertion and fixation portion 110 extending from another side of the handle section 106. The gauging portion 108 is configured to aid in determining (e.g., gauging) the size of a soft tissue retention device/implant to use with a particular soft tissue and bone complex. The insertion and fixation portion 110 is configured to temporarily hold at least a portion of the retention implant during the insertion and attachment procedure. The handle section 106 may also include more implements for more functions extending therefrom.

The installation instrument 105 allows for one-handed fixation and compression of the retention implant. As shown in FIGS. 19-24, the handle section 106 comprises an aperture, annulus, ring, loop, band, or the like 112 configured (e.g., sized and shaped) to allow a user to extend a digit therethrough, such as a user's thumb. In this way, a user can extend their thumb (for example) through the aperture 112 and use at least a portion of the rest of their hand/fingers to engage the patient (e.g., engage a portion of the patient's foot or other body portion on an opposing side of the portion engaged (indirectly or directly) by the instrument 105), as explained further below and shown in FIG. 25.

Figure 19:
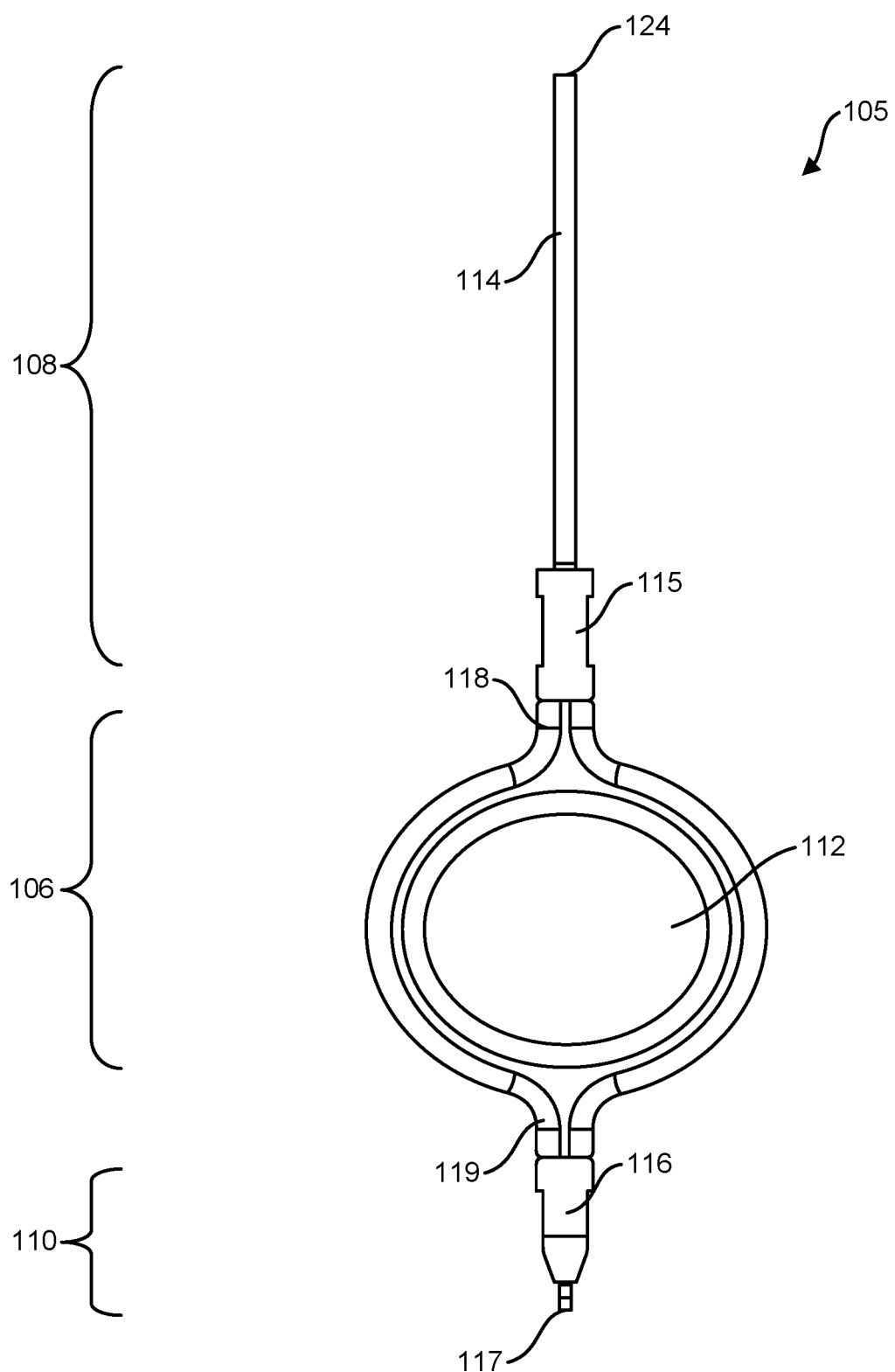
FIG. 19 illustrates side view of an exemplary instrument for installing the soft tissue retention device of FIGS. 1-18 during a soft tissue-to-bone attachment procedure, in accordance with an aspect of the present disclosure.
Figure 20:
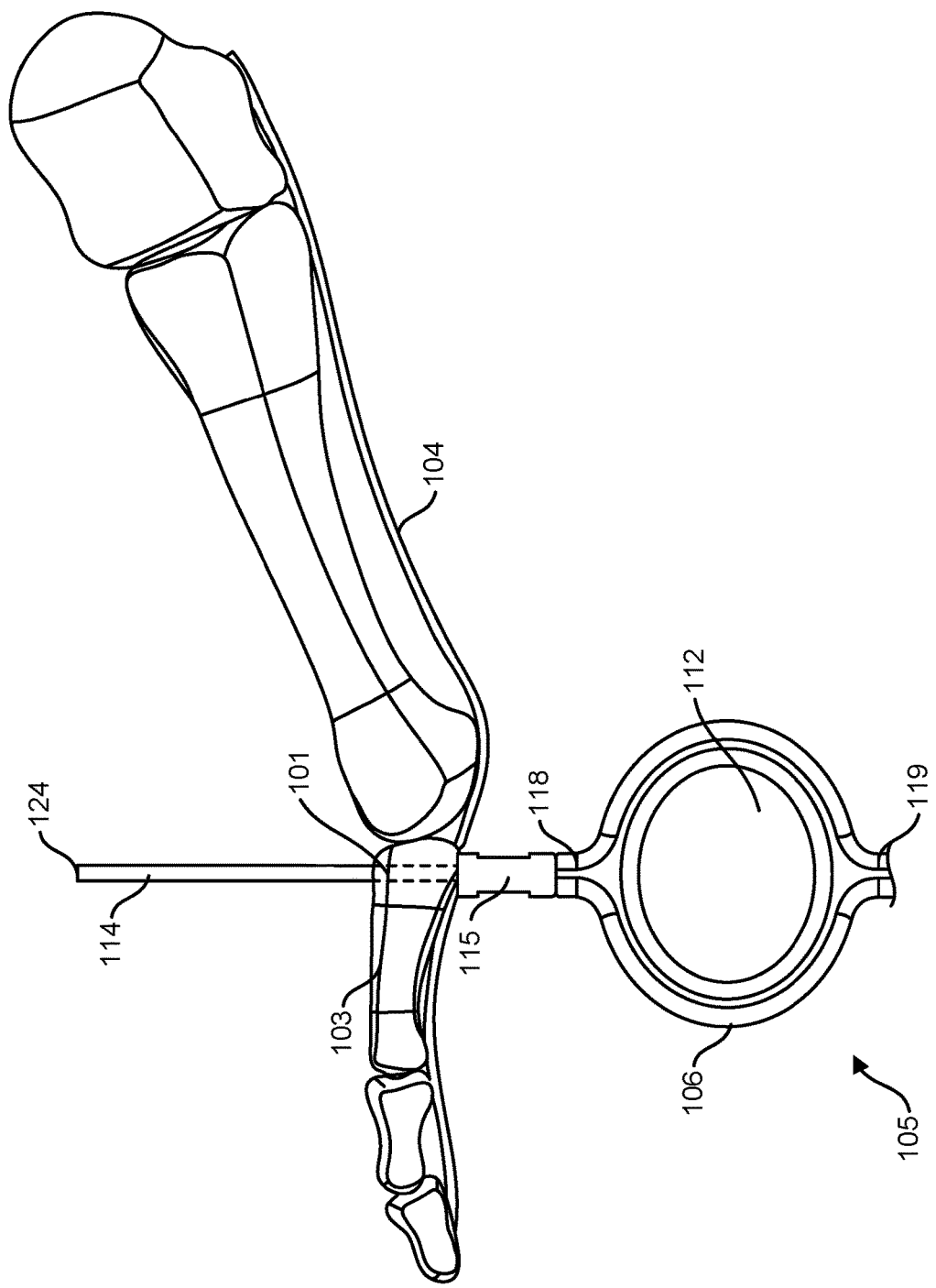
FIG. 20 illustrates a size gauging process utilizing the instrument of FIG. 19 during the soft tissue-to-bone fixation procedure.
Figure 21:
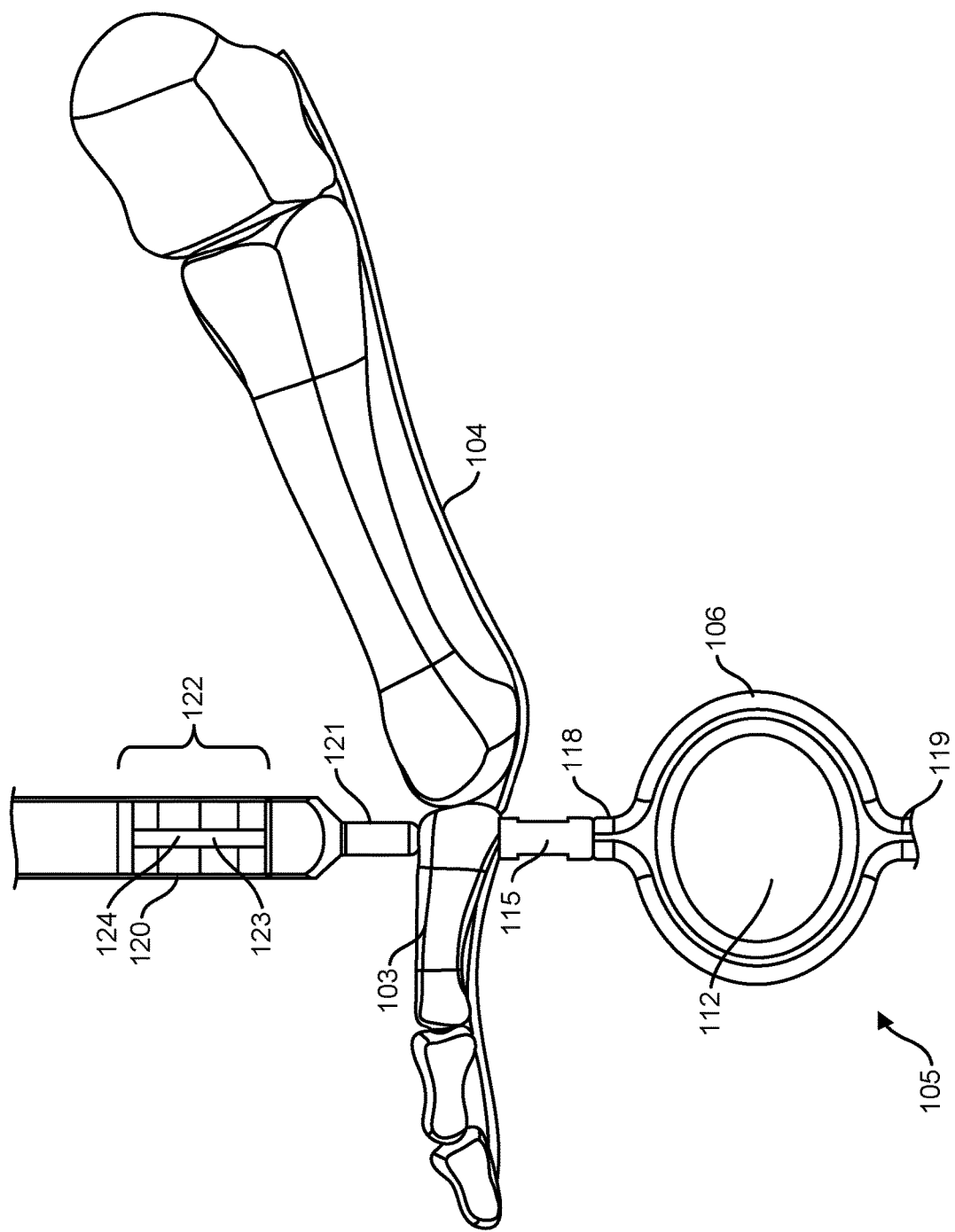
FIG. 21 further illustrates the size gauging process of FIG. 20 utilizing the instrument of FIG. 19 and a size gauge, in accordance with an aspect of the present disclosure.

As shown in FIGS. 19-21, the gauging portion 108 includes a base portion 115 that extends radially from a neck portion 118 situated at one side of the handle section 106. As also shown in FIGS. 19-21, a rod portion 114 extends radially from the base portion 115 and defines a free end or tip 124 of the gauging portion 108. When inserted into a through hole (e.g. drilled) of a bone, the rod portion 114 aids in gauging (e.g., visually determining) an implant size to use with the particular soft tissue and bone complex, while the base 115 provides a stop/seat surface to seat against or interface with the soft tissue and/or bone. In some embodiments, as shown in FIGS. 19-21, the gauge rod portion 114 has a smooth outer texture. In one exemplary embodiment, the gauge rod portion 114 is cylindrical and includes a cross-sectional diameter of about 2 mm. However, other embodiments may include other configurations and/or sizes of the gauge rod portion 114.

The insertion and fixation portion 110 comprises a head portion 116 extending radially from another neck portion 119 situated at another side of the handle portion 106, as shown in FIGS. 19 and 22-25. In some embodiments, the neck portion 119 and the head portion 116 are arranged about 180° from the neck portion 118, base portion 115 and gauge rod 114. However, the instrument 115 may include other arrangements/orientations thereof. As shown in FIGS. 19 and 2-25, the head portion 116 includes a drive projection or tip 117 configured to temporarily engage a threaded and/or non-circular drive aperture of the implant, such as a soft tissue retaining portion or member thereof, for implantation and fixation (e.g., via application of a torque) of the implant. In one embodiment, the tip 117 and the aperture of the implant (e.g., the soft tissue retaining member) are threaded for threaded engagement therebetween (e.g., with a M1.25-0.3 thread). Other threads and/or connection configurations between the tip 117 and the aperture of the implant (e.g., the soft tissue retaining member) may be employed. The head portion 116 also provides another stop/seat surface to seat against or interface with the implant (e.g., the soft tissue retaining member thereof) and/or soft tissue and/or bone. When received on a user's digit (e.g., thumb as shown in FIG. 25), the handle portion 106 of the instrument 105 can easily rotate about the thumb for easy manual manipulation of the instrument 105 and selective usage of the gauge rod 114 or the tip 117.

FIG. 20 illustrates determining a size of a soft tissue retention implant size (e.g., size of the soft tissue anchor member and/or size of the bone anchor member thereof) to use with the particular soft tissue/tendon 104 and bone 103, which may comprise gauging the height or thickness of the combined bone 103 and tendon 104. As shown in FIG. 20, after a through hole 101 has been formed (e.g., drilled) through the bone 103, the gauge rod portion 114 may be manually inserted through the tendon 104 and the through hole 101 until the bone 103 engages or comes into contact with the base portion 115 of the instrument 105, and the tendon 104 is slightly compressed. For example, the user may insert a digit (e.g., a thumb) through the aperture 112 of the handle portion 106 and wrap one or more other finger on the opposing side of the bone (e.g., the dorsal side).

As shown in FIG. 21, with the gauge rod portion 114 extending through the tendon 104 and the through hole 101, and the base portion 115 abutting, and potential compressing, the tendon 104 and/or bone 103, a gauge 120 may be received onto the exposed portion of the gauge rod portion 114. A lower sleeve portion 121 of the gauge 120 may include an aperture of the like such that the lower sleeve portion 121 is received over the rod portion 114 and contacts a top or opposing side or surface of the bone 103, as shown in FIG. 21. As also shown in FIG. 21, the gauge 120 may include a recess, opening or surface area 123 along within the rod portion 114 of the gauge 120 extends. The area 123 may include a plurality of visual and/or tactile indications 122 that form a size chart or otherwise indicate differing sized soft tissue retention devices/implants (or a component thereof). The position of the gauge rod tip 124 relative to the markings 122 of the gauge 120 (e.g., the marking 122 positioned closest to the tip 124) can thereby be utilized by the user to indicate the size of the tissue retention device/implant that corresponds to the size of the patient's bone 103 and/or tendon 104.

Figure 22:
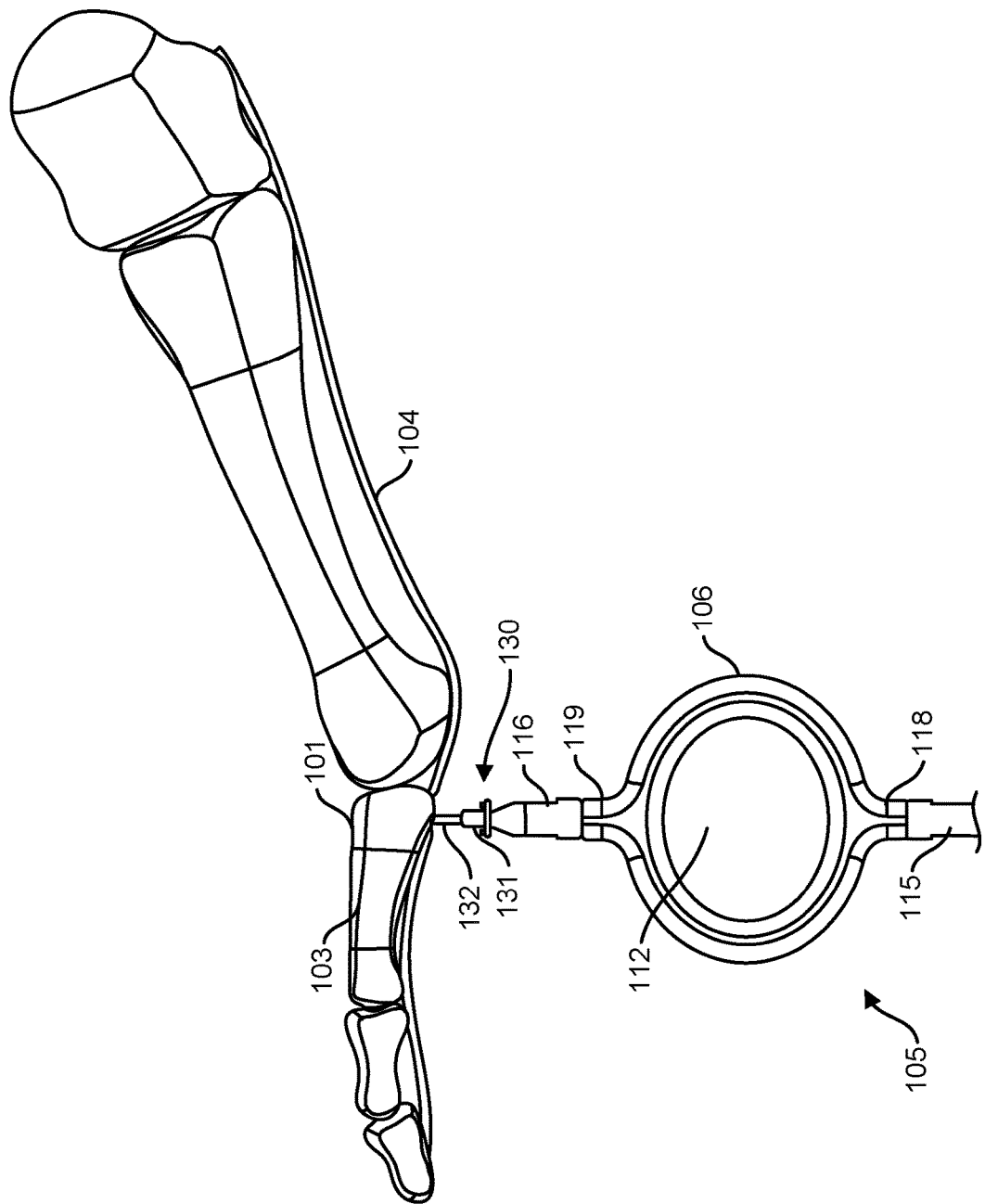
FIG. 22 illustrates the positioning of the tack member of the soft tissue retention device of FIG. 19 through the soft tissue and into a hole within the bone utilizing the instrument of FIG. 19.

With the size of the soft tissue retention device/implant determined/gauged, the instrument 105 may then be utilized to install/implant the soft tissue retention device/implant by rotating the instrument 105 about the user's digit/finger (e.g., thumb) and removably coupled the drive tip 117 with a drive aperture or opening of a soft tissue retention tack member or portion 130 of the soft tissue retention device/implant. For example, the tip 117 may be threadably coupled with the drive aperture/opening of the soft tissue retention tack member 130. As shown in FIG. 22, the instrument 105 may then be utilized to insert the soft tissue retention tack member or portion 130 into the through hole 101 of the bone 103 and against the soft tissue/tendon 104. Thereafter, with the soft tissue retention tack member 130 removably coupled with the drive tip 117 of the head portion 116 of the instrument 105, a threaded stem portion 132 of the soft tissue retention tack member 130 may be held or maintained within the through hole 101 of the bone 103 (and/or a head portion of the soft tissue retention tack member 130 engaged/in abutment against the soft tissue/tendon 104) via one handed manipulation of the instrument 105 by the user (e.g., via a user's digit/finger (e.g., a thumb) extending through the aperture 112 of the handle portion 106 of the instrument 105).

Figure 23:
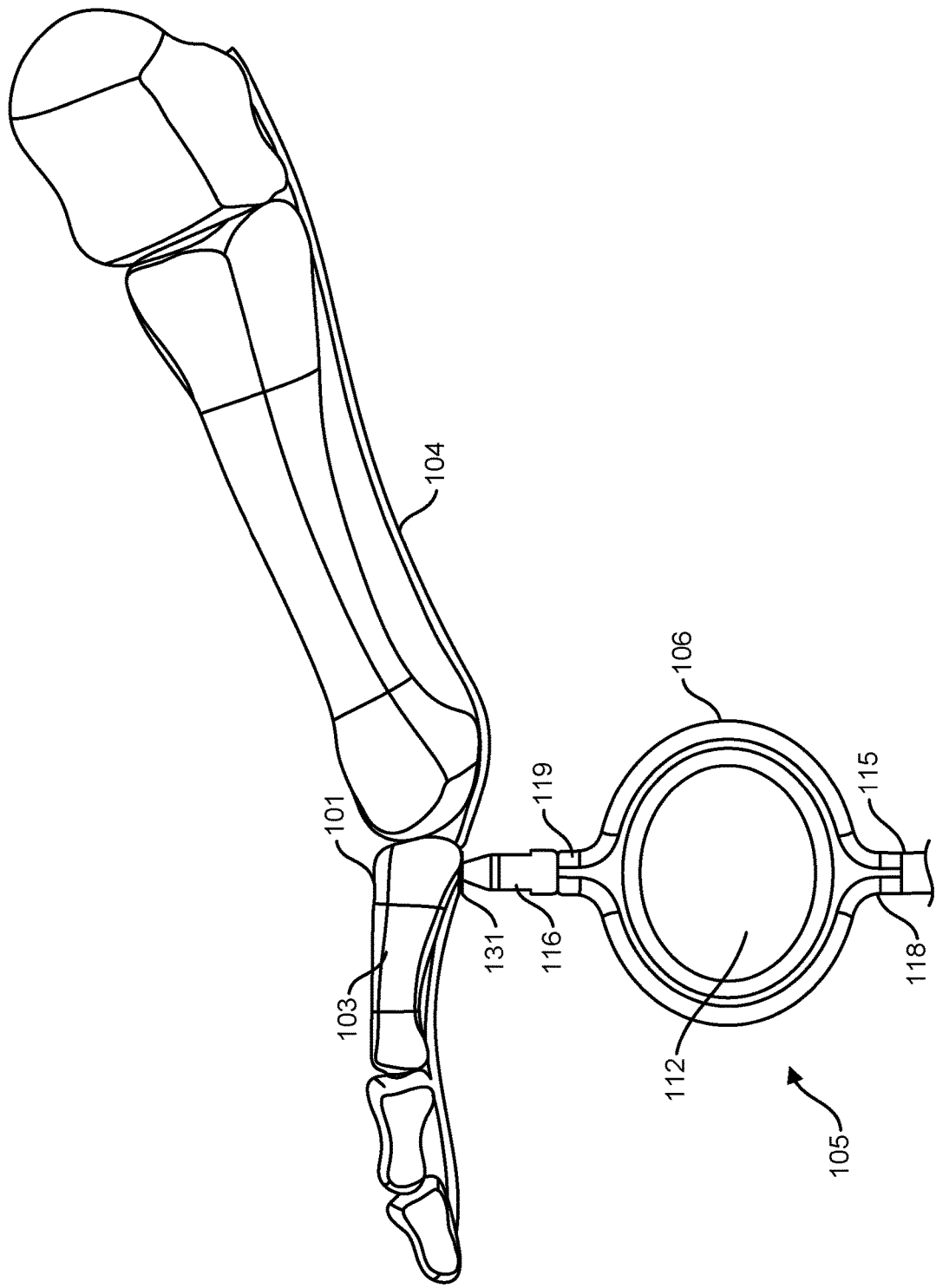
FIG. 23 illustrates compression of the soft tissue between the bone and the tack member via the instrument of FIG. 19.

With the soft tissue retention tack member 130 extending within the through hole 101 of the bone 103 and/or against the soft tissue/tendon 104, the soft tissue/tendon 104 may be compressed against the bone 103, as shown in FIG. 23. In some embodiments, the bone 103 and soft tissue/tendon 104 may be relatively arranged into a particular anatomical arrangement/configuration, and the instrument 105 used to force the soft tissue retention tack member 130 against the soft tissue/tendon 104, and thereby compress the soft tissue/tendon 104 between the soft tissue retention tack member 130 and the bone 103. For example, in some embodiments, the user may manually straighten the toe bone 103 of the patient's foot, and then force the soft tissue retention tack member 130 against the tendon 104, and thereby compress the tendon 104 between the soft tissue retention tack member 130 and the bone 103, to maintain the relative orientation of the toe bone 103 (after letting go of the toe bone 103), as shown in FIGS. 23 and 25. In such a configuration, the tendon 104 can be held in its desired location by compression of the instrument 105 via the user's hand and the hand of the user that engages the instrument 105 being wrapped around the patient's foot/toe bone 103 (i.e., a one-handed technique or method). Alternatively, the tendon 104 can be held in its desired location by compression of the instrument 105 via a user's hand and the other hand of the user engaging/forcing an opposing side of the patient's foot/toe bone 103 (i.e., a two-handed technique or method), as shown in FIG. 25.

Figure 24:
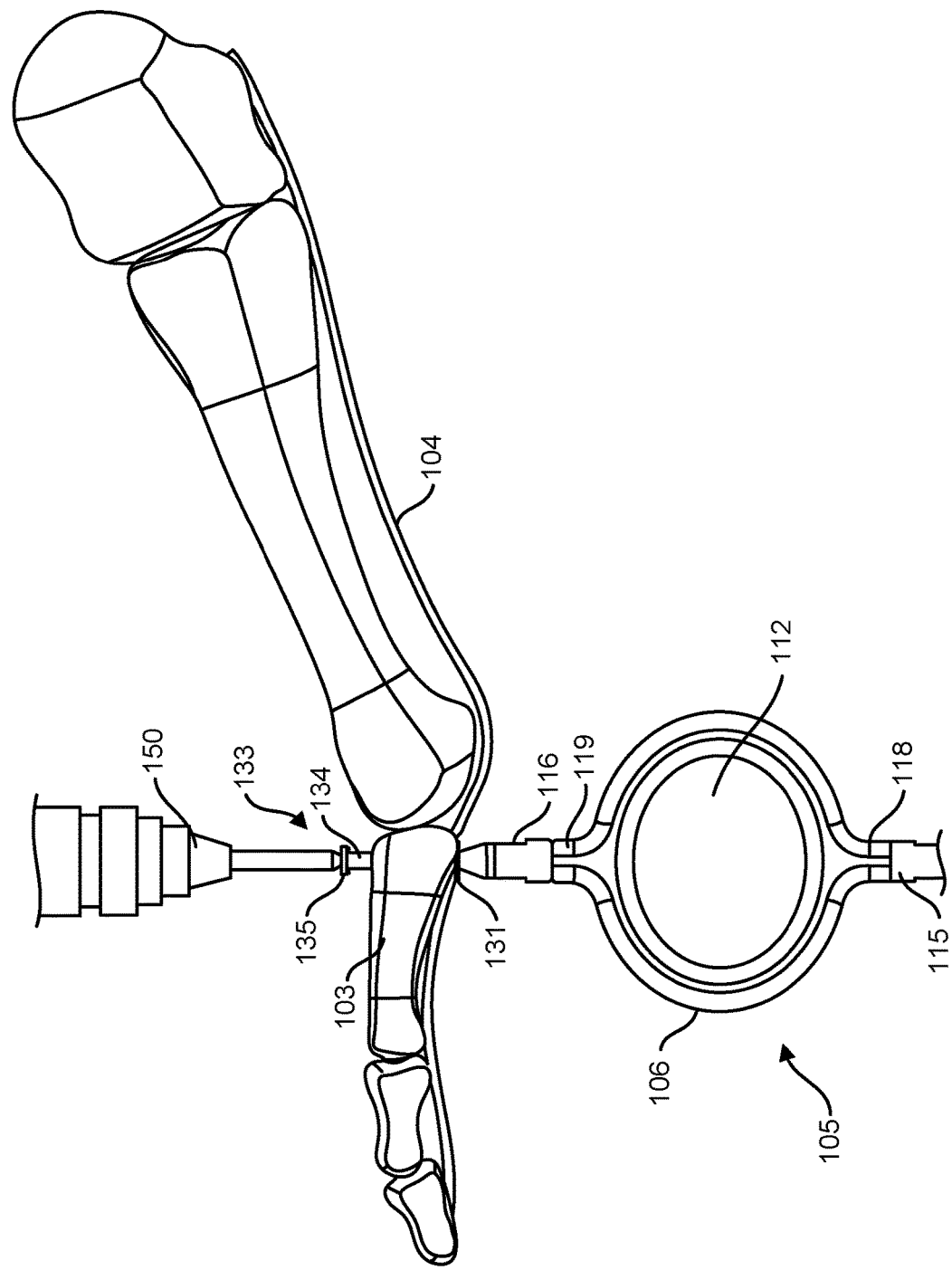
FIG. 24 illustrates the fixation of the soft tissue retention device of FIGS. 1-18, and the soft tissue and the bone, via threadably coupling the bone anchor member of the soft tissue retention device of FIG. 19 to the tack member.

FIG. 24 shows the compression of the soft tissue/tendon 104 against the bone 103 maintained by the user via the instrument 105 and the soft tissue retention tack member 130, a bone anchor member or portion 133 of the soft tissue retention device/implant may be positioned into the bone through hole 101 from an opposing side thereof relative to the soft tissue/tendon 104 and soft tissue retention tack member 130. As shown in FIG. 24, a threaded stem portion 134 of the bone anchor member 133 may be positioned within the through hole 101 of the bone 103, and a torque device or tool 150 may be engaged with a drive aperture or opening of a head portion 135 of the bone anchor member 133. The bone anchor member 133 may be rotated/torqued via the torque device 150 such that the threaded stem portion 134 of the bone anchor member 133 threadably engages, mates or couples with the threaded stem portion 132 of the soft tissue retention tack member 130 within the through hole 101 of the bone 103. Rotation of the soft tissue retention tack member 130 may be manually prevented (e.g., torque applied thereto) by the user via the engagement of the drive tip 131 of the instrument 105 with the drive aperture/opening of the head portion of the soft tissue retention tack member. Rotation of the bone anchor member 133 can thereby provide compression onto the soft tissue retention tack member to compress/force the soft tissue/tendon 104 onto the bone 103.

Referring to the drawings, wherein like reference numerals are used to indicate like or analogous components throughout the several views, and with particular reference to FIGS. 26-43, there is illustrated an exemplary embodiment of a soft tissue (such as, but not limited to, tendon or ligament) retention, coupling, fixation or securement device, implant or system 210 configured to couple, retain, fix, and/or secure soft tissue to an associated or desired bone (such as, but not limited to, a relatively small bone (e.g., a bone of the foot or hand)). In some embodiments, the soft tissue retention device 210 may be particularly configured and/or advantageous for retention of a flexor digitorum longus tendon and an associated bone, such as, but not limited to, the plantar aspect of a proximal phalangeal base (bone) particularly, but not necessarily, for the correction of a toe contracture. However, the soft tissue retention device 210 may be configured and/or effectively utilized to retain, couple or fix any soft tissue (e.g., a tendon, ligament or the like) to any bone (e.g., any relatively small bone, such as a phalange, metatarsal or metacarpal bone) of a patient (e.g., a human patient).

The soft tissue retention device 210 may be made of a biocompatible metal such as titanium, stainless steel, an alloy, or the like, or other biocompatible material such as plastic, ceramic or the like.

The soft tissue retention device (or system or implant) 10 may comprise a first component 212 and a second component 214, the nomenclature first and second being arbitrary. The first component 212, without being restrictive, may be configured as a soft tissue tack member, portion or component, while the second component 214, without being restrictive, may be may be configured as bone anchor member, portion or component 212. When implanted, the soft tissue tack member 212 and the bone anchor member 214 are configured to nest and removably or fixedly couple together. As explained further below, one of the soft tissue tack member 212 and the bone anchor member 214 may be configured as an externally threaded male portion, and the other of the soft tissue tack member 212 and the bone anchor member 214 may be configured as an internally threaded female portion (for threadably mating with the externally threaded male portion).

In some embodiments, the soft tissue retention device 210 may be a two-piece device comprised of only the soft tissue tack member 212 and the bone anchor member 214. In some other embodiments, the soft tissue retention device 210 may comprise additional components over the soft tissue tack member 212 and the bone anchor member 214. In some embodiments, the soft tissue tack member 212 may be a one-piece or integral (e.g., monolithic) component. In some other embodiments, the soft tissue tack member 212 may be comprised of two or more separate and distinct components coupled together. In some embodiments, the bone anchor member 214 may be a one-piece or integral (e.g., monolithic) component. In some other embodiments, the bone anchor member 214 may be comprised of two or more separate and distinct components coupled together.

As shown in FIGS. 26-38, the soft tissue tack member 212 includes a head or base portion 216 and a threaded shaft portion 218 extending from the head portion 216. The head portion 216 and the threaded shaft portion 218 may be rigidly or fixedly attached or integral such that movement therebetween is prevented. The shaft portion 218 may be externally threaded (i.e., configured as a male portion or component) as shown in FIGS. 26-38, or alternatively the shaft portion 218 may be internally threaded (i.e., configured as a female portion or component) (not shown). The head portion 216 may be generally disc-shaped (i.e., substantially flat, thin and curricular shaped) (although other shapes may be used). As also shown in FIGS. 26-38, the head portion 216 may have a generally planar outer or upper side, face or surface 220 and an inner or under side, face or surface 222. The shaft portion 218 extends from a central or center portion of the inner side 222 of the head portion 216. The shaft portion 218 may extend generally transverse from the inner side 222 of the head portion 216. The shaft portion 218 may define a first diameter, and the head portion 216 may define a second diameter that is larger than the first diameter.

As shown in FIGS. 27, 29, 32, 34, 36 and 38, the head portion 216 includes a drive or torque aperture, indentation, cavity or slot 224 in the outer side 220 thereof that is configured to mate with an instrument, tool or guide member for rotating (or preventing rotation), inserting or aiding in the insertion, guiding, installation or implantation of the soft tissue tack member 212 into/through soft tissue and a bone, as explained further below. The drive aperture 224 is of a non-circular cross-sectional shape so that that a torque device can mate therein and an apply a rotational force to the soft tissue tack member 212.

Figure 36:
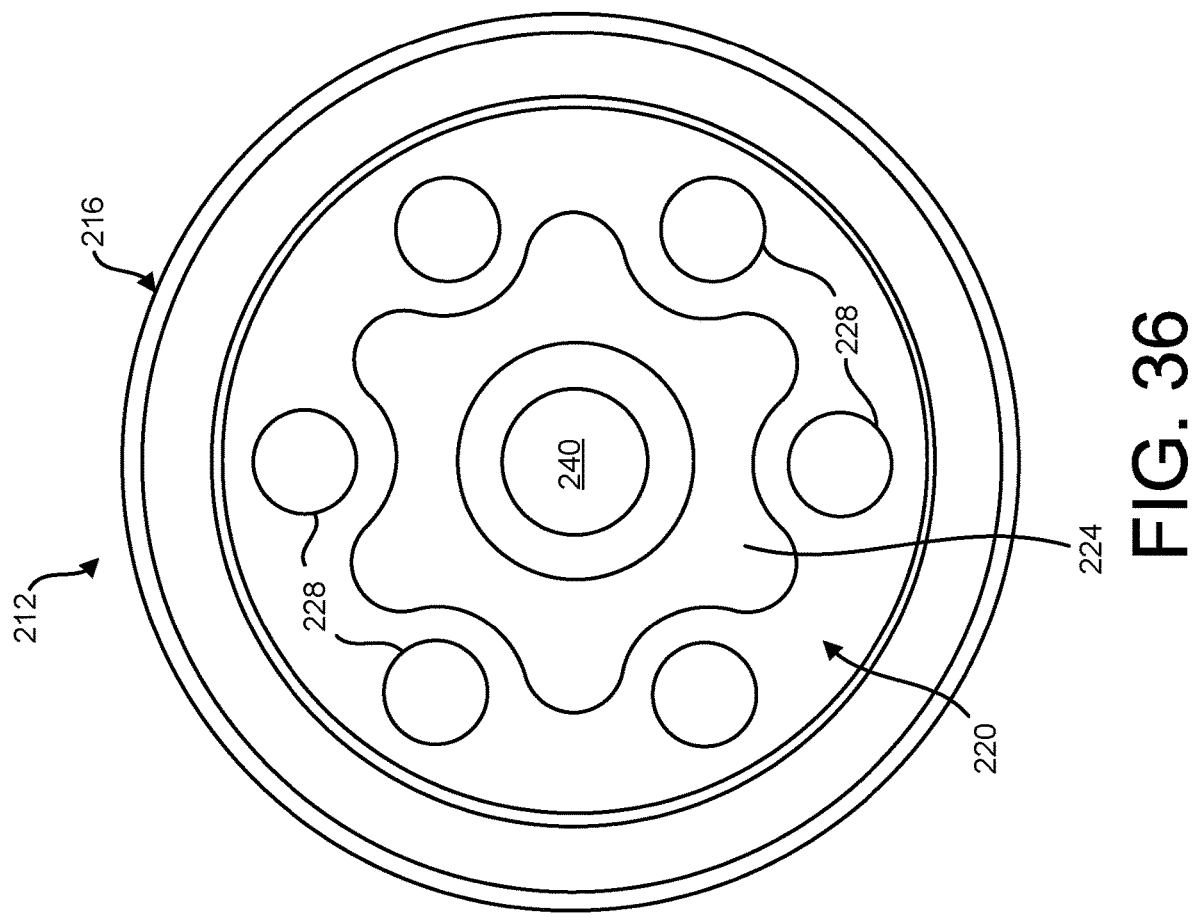
FIG. 36 illustrates a top view of the soft tissue tack member of FIG. 34.
Figure 37:
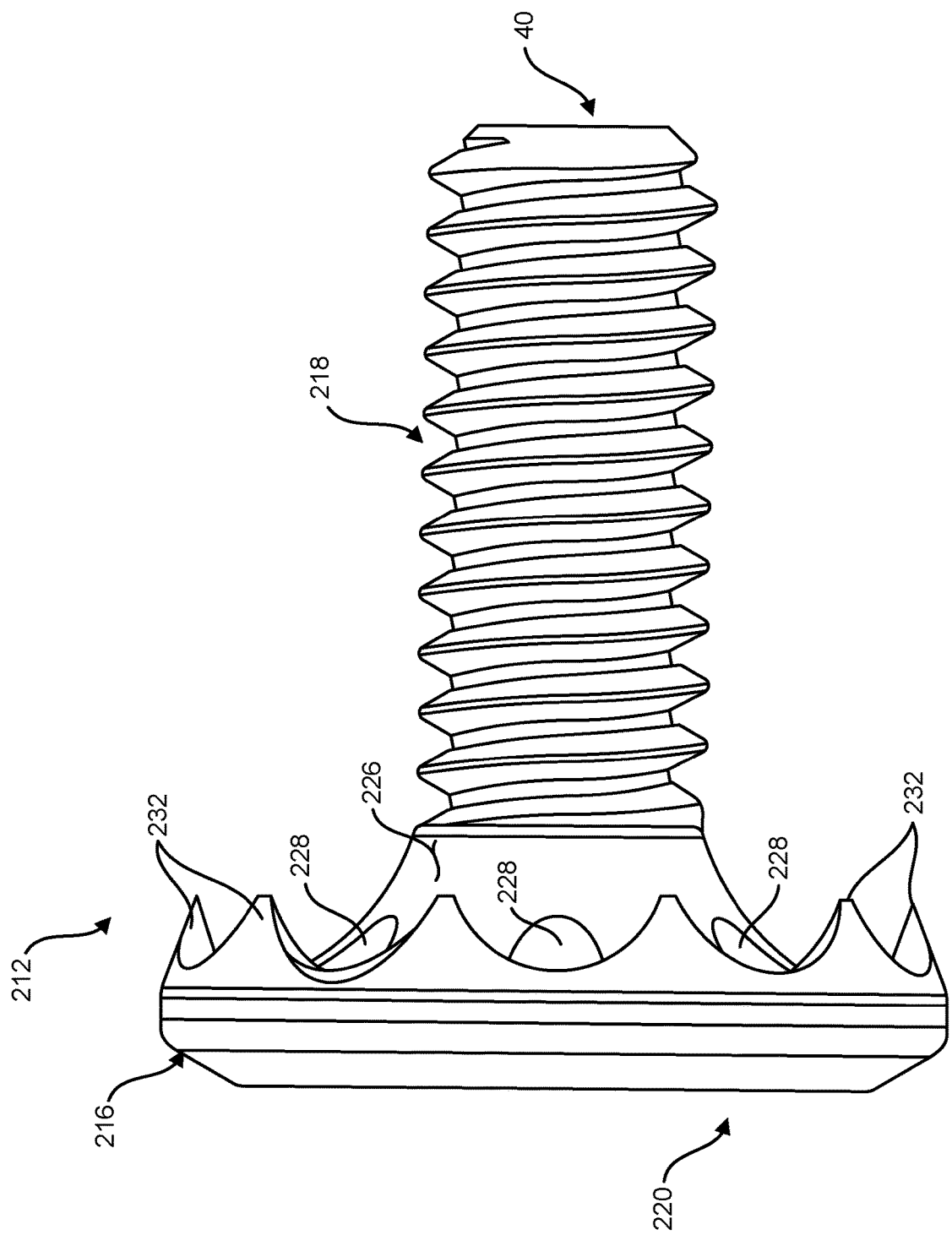
FIG. 37 illustrates a side view of the soft tissue tack member of FIG. 34.
Figure 38:
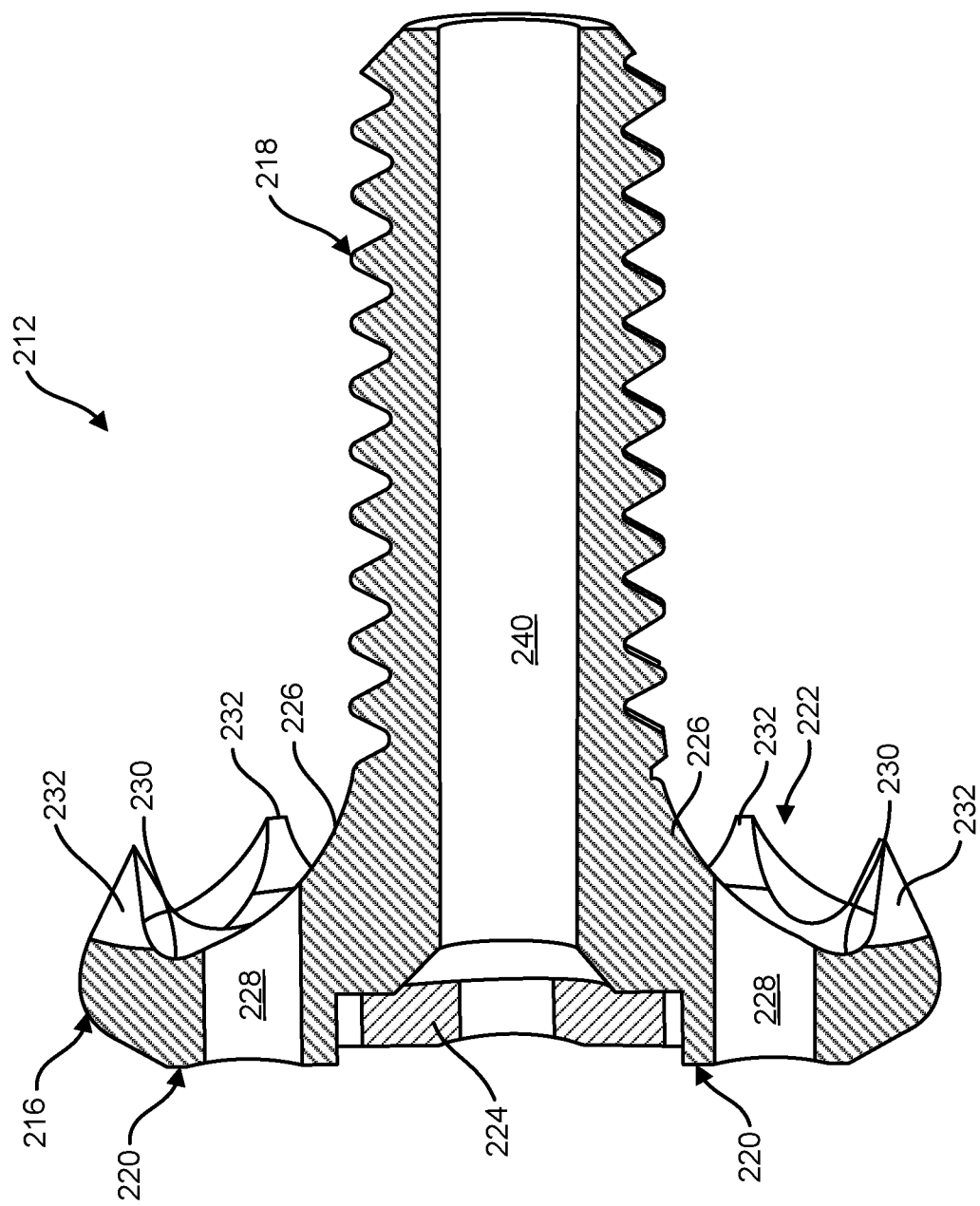
FIG. 38 illustrates a cross-sectional side view of the soft tissue tack member of FIG. 34.
Figure 39:
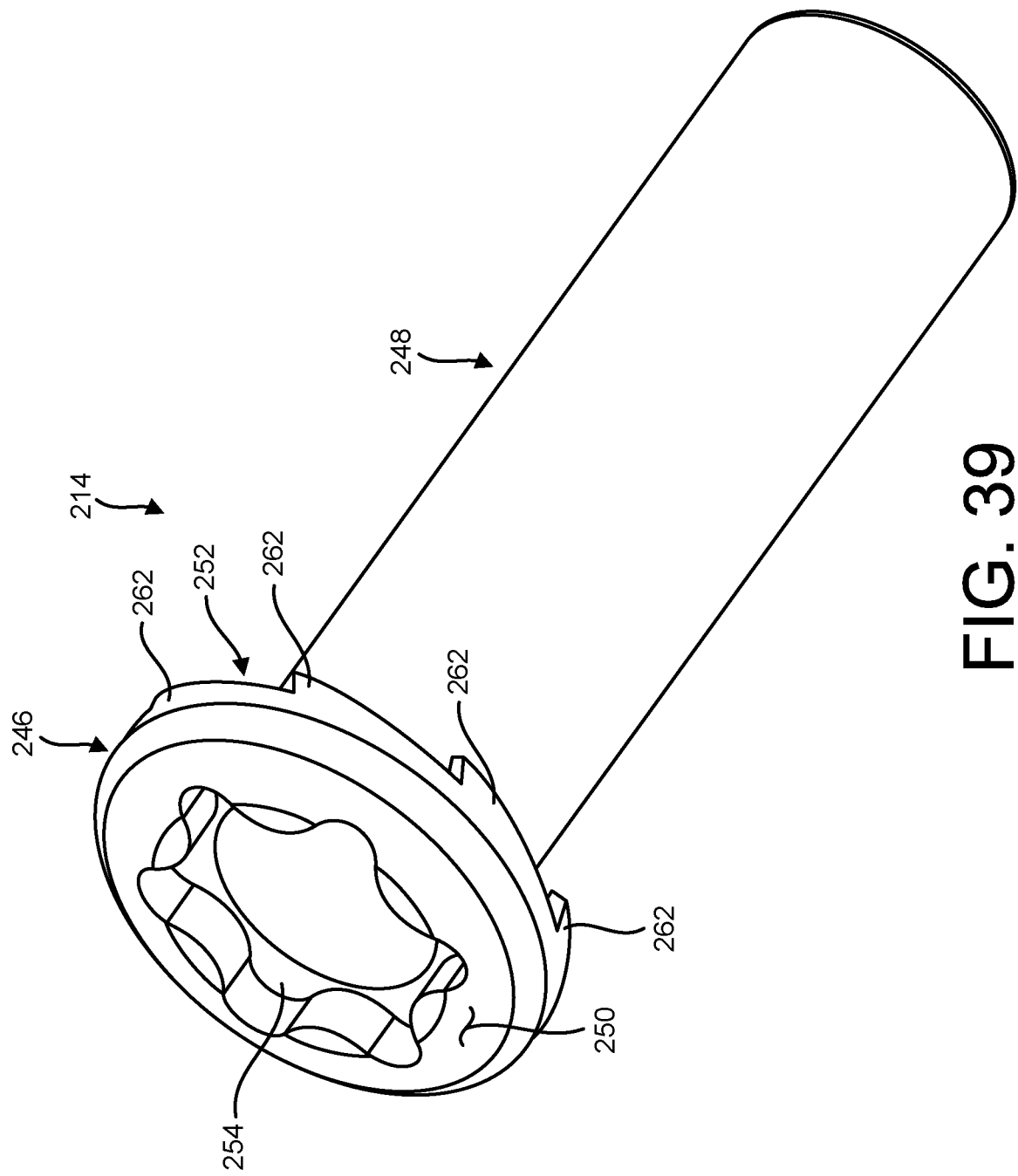
FIG. 39 illustrates a bottom perspective view of a bone anchor member of the soft tissue and bone retention device of FIG. 26.
Figure 40:
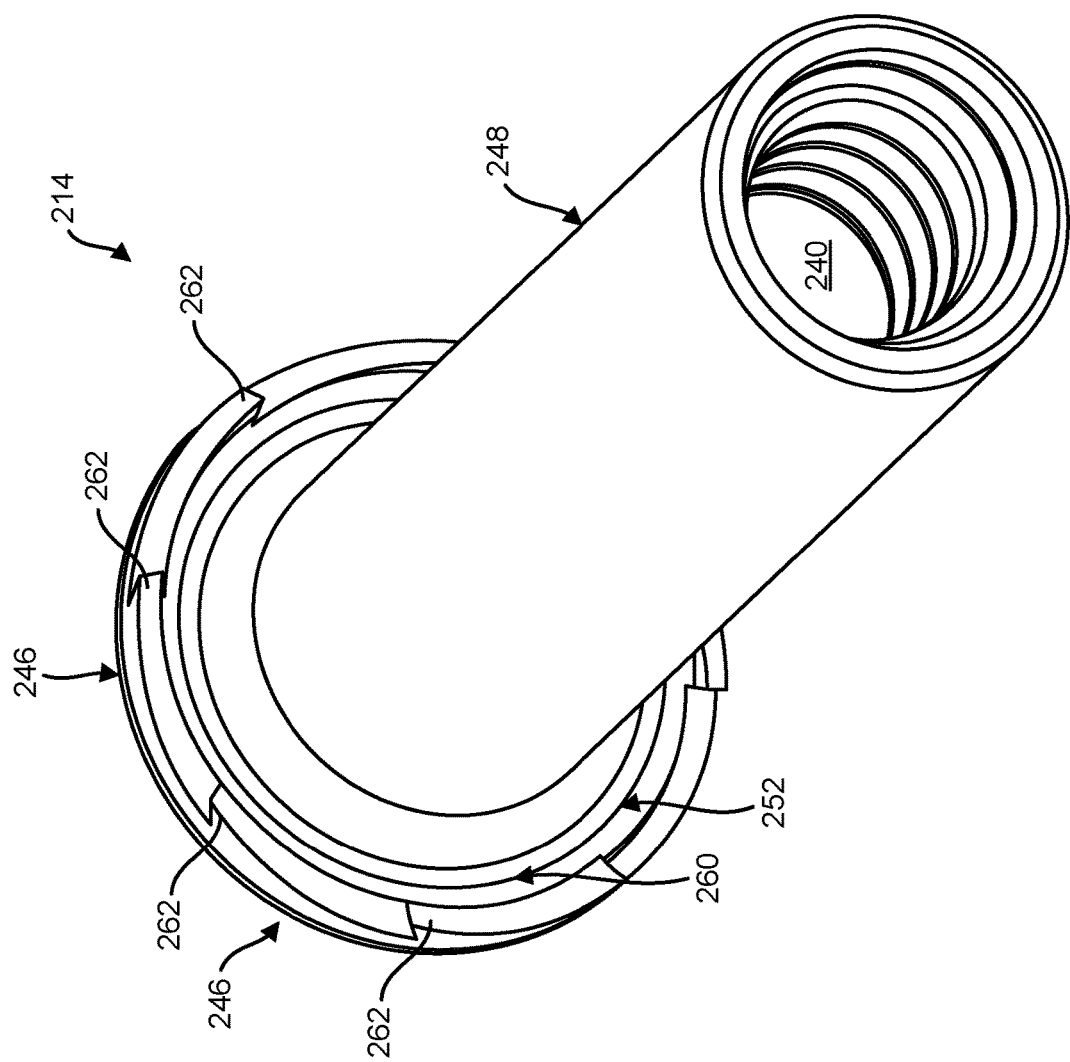
FIG. 40 illustrates a top perspective view of the bone anchor member of FIG. 39.
Figure 41:
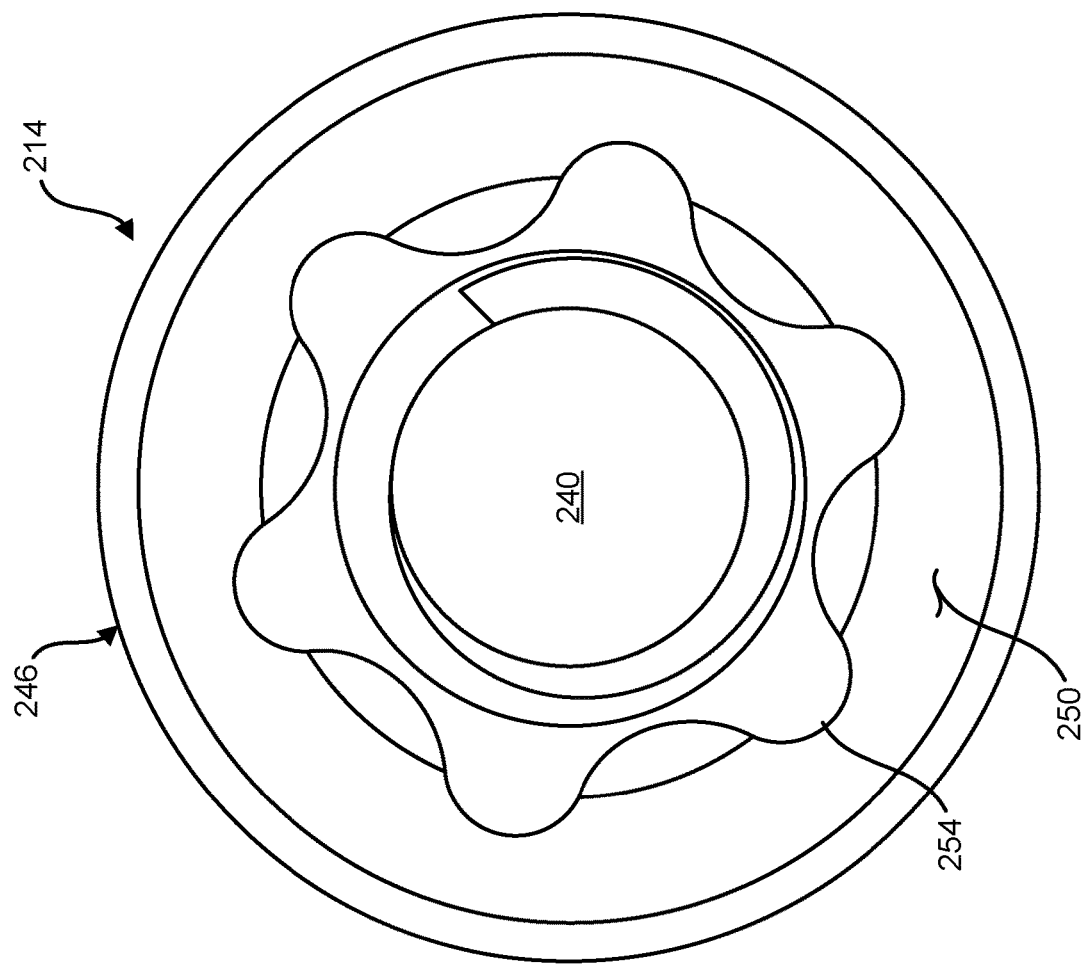
FIG. 41 illustrates a bottom view of the bone anchor of FIG. 39.
Figure 42:
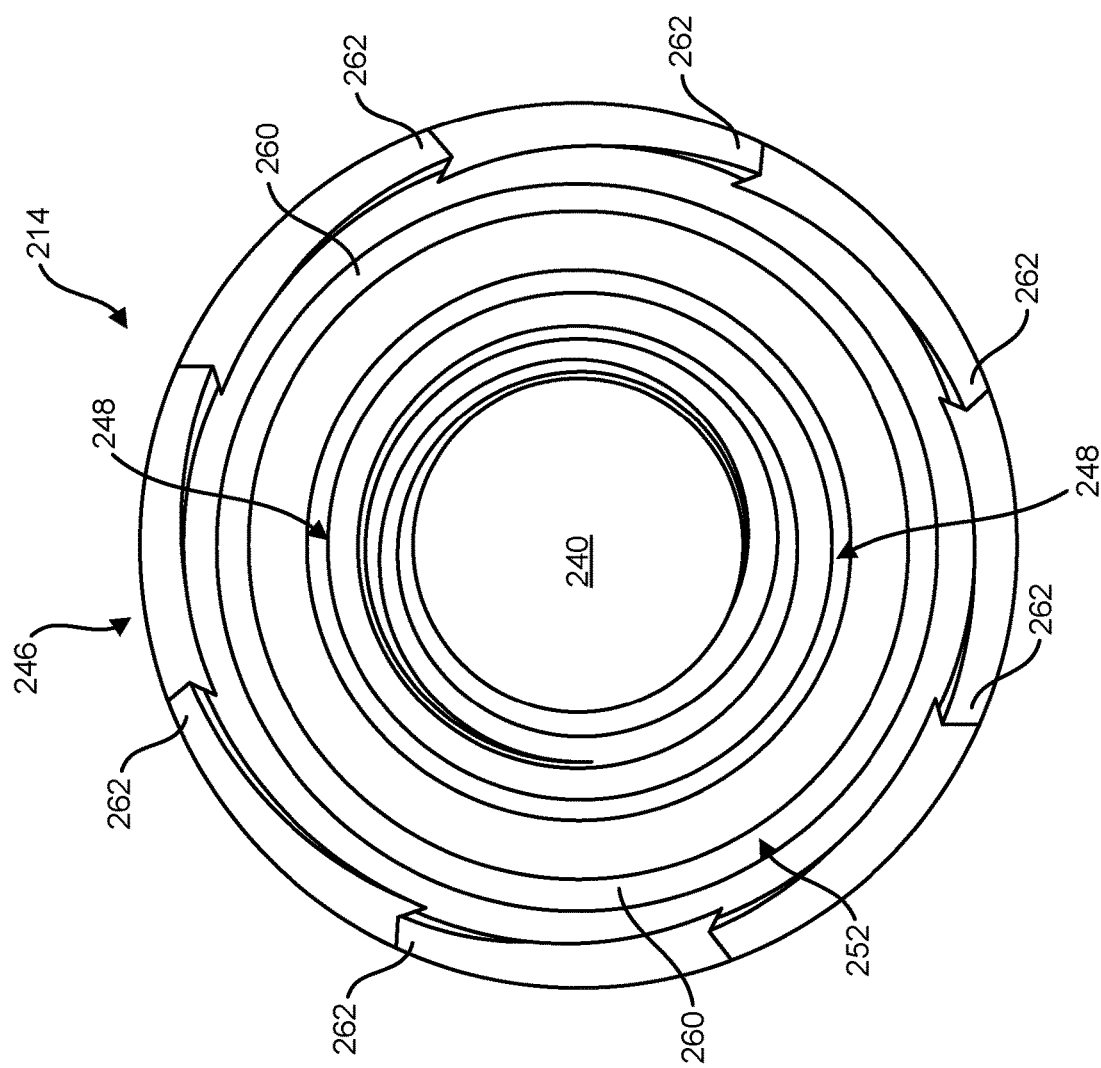
FIG. 42 illustrates a top view of the bone anchor member of FIG. 39.
Figure 43:
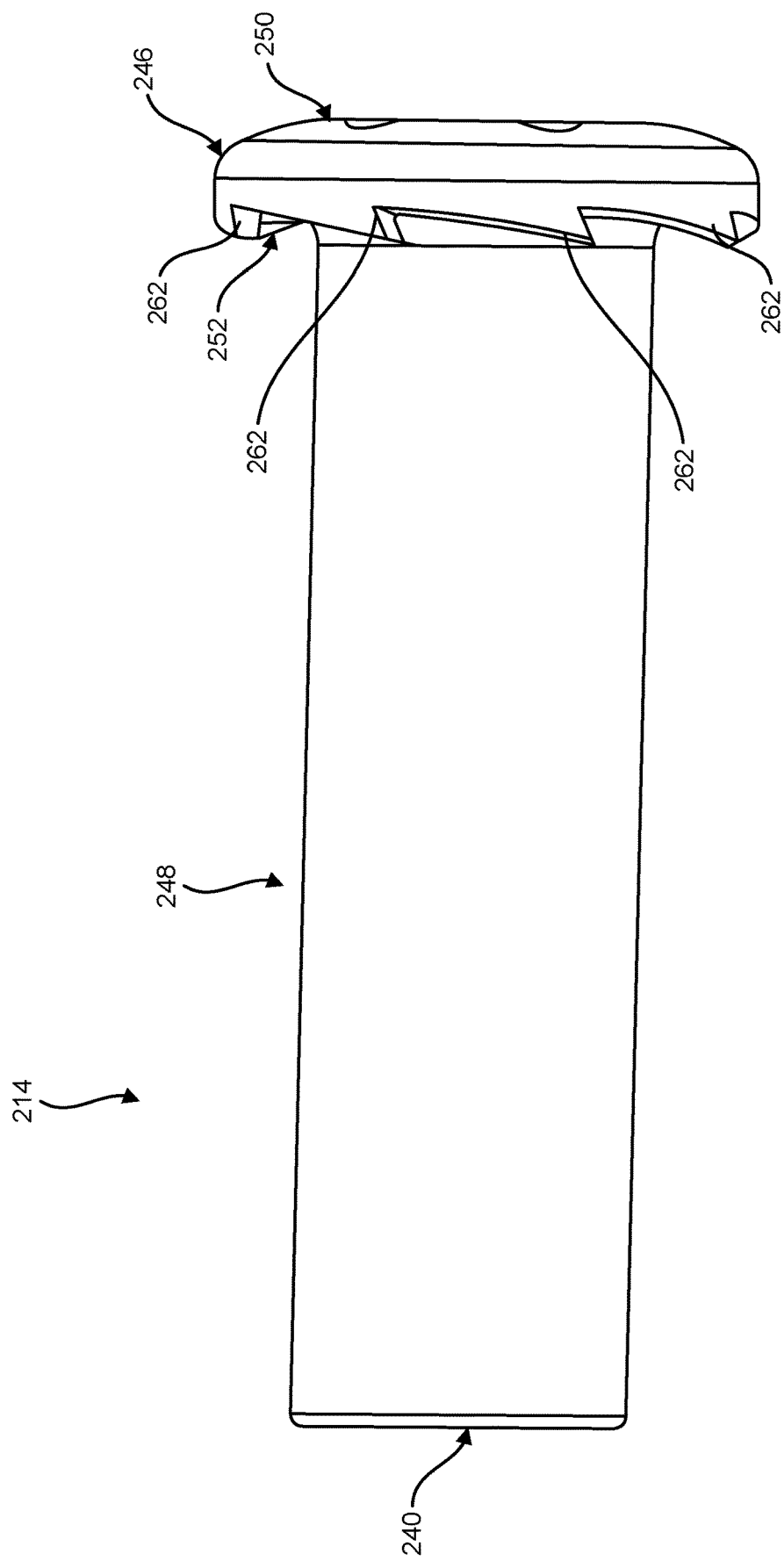
FIG. 43 illustrates a side view of the bone anchor member of FIG. 39.
Figure 44:
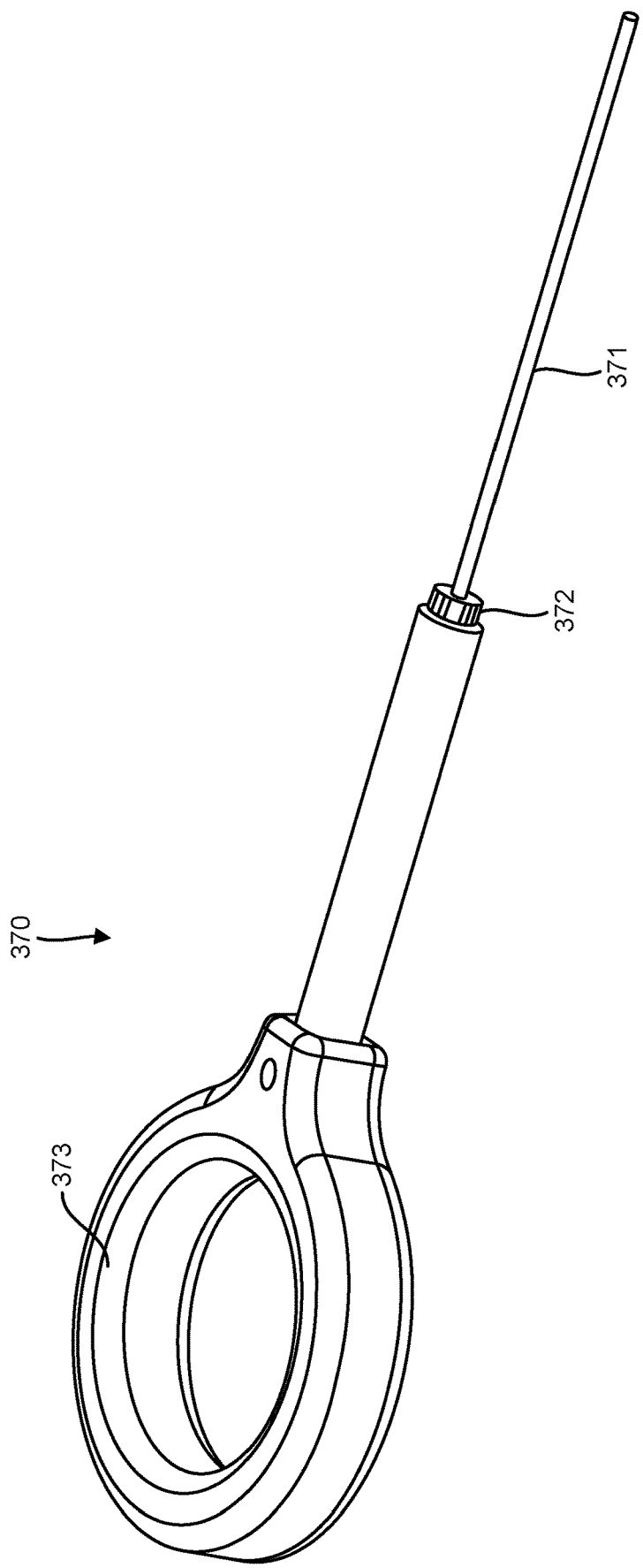
FIG. 44 illustrates a perspective view of an exemplary tack member drive and guide instrument, in accordance with an aspect of the present disclosure.
Figure 45:
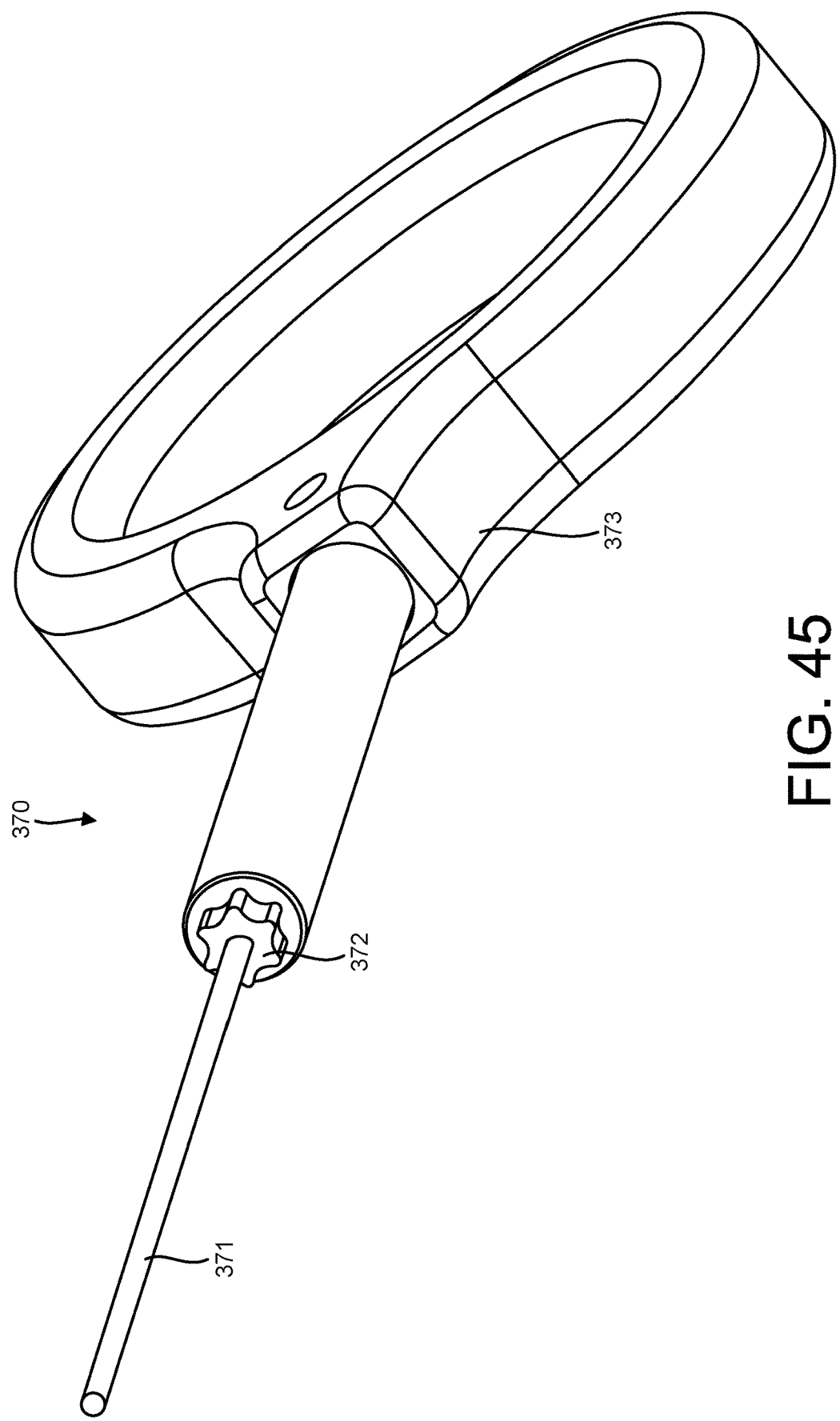
FIG. 45 illustrates another perspective view of the tack member drive and guide instrument of FIG. 44.
Figure 46:
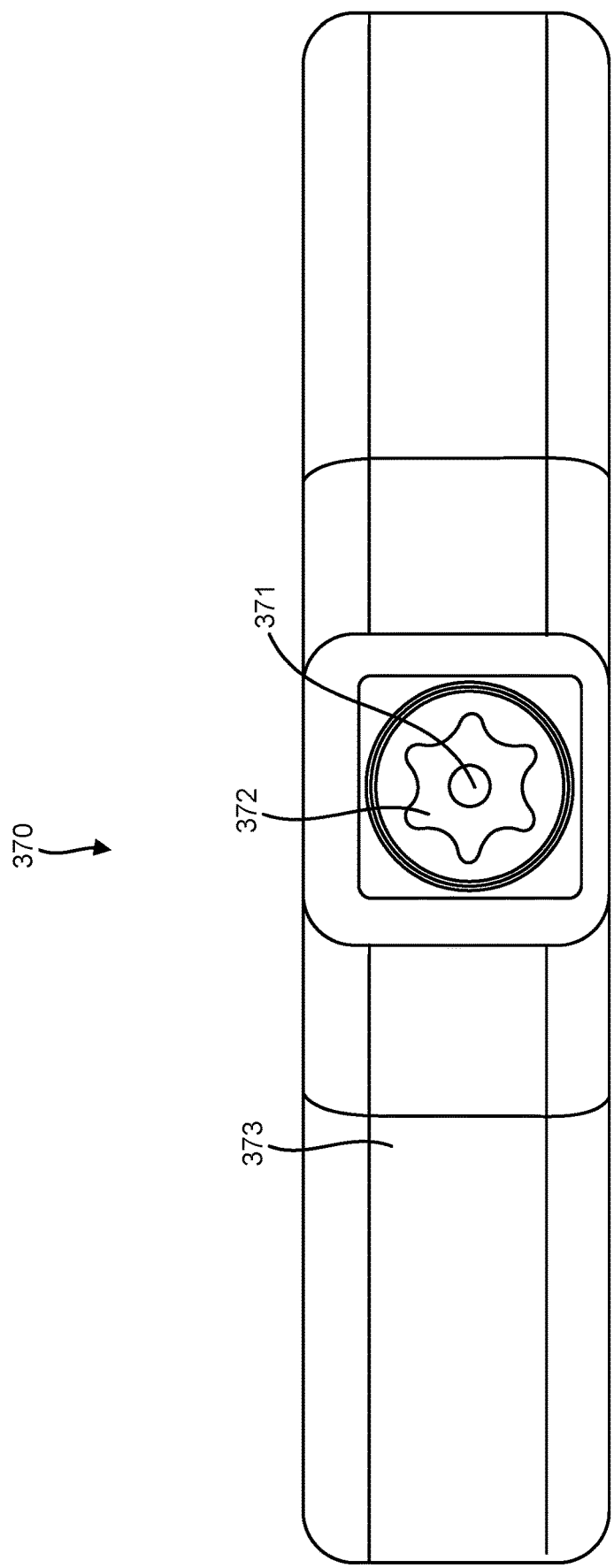
FIG. 46 illustrates a drive end view of the tack member drive and guide instrument of FIG. 44.

As shown in FIGS. 27-29, 32-36 and 38, the head portion 216 and the shaft portion 218 may include a cannulated opening 240 extending therethrough about an axis (e.g., a longitudinal axis and/or an axis of rotation) of the tack member 212. The tack member 212, as a whole, may thereby be cannulated. The drive aperture 224 may be aligned with, or formed as part as, the outer portion of the cannulated opening 240 of the tack member 212. If the shaft portion 218 is internally threaded as opposed to being externally threaded as shown in FIGS. 36-38, the cannulated opening 240 thereof may include the internal threads.

As shown in FIGS. 26, 28, 30-33, 35, 37 and 38, the inner side 222 of the head portion 216 may include an annular sloped (e.g., arcuately concave) or angled transition surface portion 226 that extends or transitions to/from the threaded shaft portion 218. As shown in FIGS. 25, 26 and 29-38, the head portion 216 may include a plurality of through holes 228 extending therethrough that are circumferentially spaced about the periphery or outer sides of the drive aperture 224 and shaft portion 218. The through holes 228 may extend from the (planar) outer side surface 220 of the head portion 216 to the outer peripheral portion of the transition portion 226 of the inner side 222 of the head portion 216. The through holes 228 are configured to allow soft tissue to extend therein/therethrough when the soft tissue retention device 210 is tightened/compressed onto the soft tissue and adjacent bone to exsanguinate and securely grip/couple the soft tissue.

As shown in FIG. 38, the inner side 222 of the head portion 216 may also include an annular arcuately concave groove or depression portion 230 that extends between an inner or back side of an outer peripheral row of teeth or projections 232 and the transition portion 228. The annular depression 230 may be configured to contain or filled by the soft tissue when the soft tissue retention device 210 is tightened/compressed onto the soft tissue and adjacent bone. As also shown in FIG. 38, the row of teeth 232 may define the outer periphery of the head portion 216. In some embodiments, the inner side 222 of the head portion 216 may only comprise a single row of the teeth 232 at the periphery thereof. The inner or back side of the teeth 232 may be arcuate (e.g., arcuately concave) and/or planar. The outer side of the teeth 232 may planar and/or arcuate (e.g., arcuately convex or concave). The lateral sides of the teeth 232 (and the gullets extending therebetween) be arcuate (e.g., arcuately concave), and the teeth 232 may narrow as they extend longitudinally away from the inner side 222 of the head portion 216, as shown in FIGS. 26, 27, 30, 31, 33, 34 and 37. In some other embodiments, the lateral sides of the teeth 232 be planar and/or arcuate. The tips of the teeth 232 may be linear/flat or planar. In some other embodiments, the tips of the teeth 232 may be arcuate. The teeth 232 may define an axis that is aligned with the axis of the tack member 212. Stated differently, the teeth 232 may extend along a direction that is aligned or parallel to the axis of the tack member 212 in all directions (and thereby perpendicular or normal to the head portion 216).

As explained above, the threaded shaft portion 218 of the soft tissue tack member 212 is configured to threadably couple with a corresponding or mating threaded shaft portion 248 of the bone anchor member 214, as shown in FIGS. 26-38. As shown in FIGS. 26-32 and 39-43, the bone anchor member 214 includes a head or base portion 246 and the threaded shaft portion 248 extending from the head portion 246. The head portion 246 and the threaded shaft portion 248 may be rigidly or fixedly attached or integral such that movement therebetween is prevented. The shaft portion 248 may be internally threaded (i.e., configured as a tubular hollow female portion or component) as shown in FIGS. 26-32 and 29-43, or alternatively the shaft portion 248 may be externally threaded (i.e., configured as a male portion or component) (not shown).

The head portion 246 may be generally disc-shaped (i.e., substantially flat, thin and curricular shaped) (although other shapes may be used). As also shown in FIGS. 26-32 and 29-43, the head portion 246 may have a generally planar outer or upper side, face or surface 250 and an inner or under side, face or surface 252. The shaft portion 248 extends from a central or center portion of the inner side 252 of the head portion 246. The shaft portion 248 may extend generally transverse from the inner side 252 of the head portion 246. The shaft portion 248 may define a first diameter, and the head portion 246 may define a second diameter that is larger than the first diameter.

As shown in FIGS. 26, 28, 32, 39 and 41, the head portion 246 of the bone anchor member 214 includes a drive or torque aperture, indentation, cavity or slot 254 in the outer side 250 thereof that is configured to mate with an instrument, tool or guide member for rotating (or preventing rotation), inserting or aiding in the insertion, guiding, installation or implantation of the bone anchor member 214 into/through a bone, as explained further below. The drive aperture 254 is of a non-circular cross-sectional shape so that that a torque device can mate therein and an apply a rotational force to the bone anchor member 214.

As shown in FIGS. 26, 28, 32 and 39-42, the head portion 246 and the shaft portion 248 may include a cannulated opening 240 extending therethrough about an axis (e.g., a longitudinal axis and/or an axis of rotation) of the bone anchor member 214. The bone anchor member 214, as a whole, may thereby be cannulated. The drive aperture 254 may be aligned with, or formed as part as, the outer portion of the cannulated opening 240 of the bone anchor member 214. If the shaft portion 248 is externally threaded as opposed to being internally threaded as shown in FIGS. 26-32 and 39-43, the cannulated opening 240 may be void of the threads.

As shown in FIGS. 27, 32, 39 and 42, the inner side 252 of the head portion 246 may include an annular sloped (e.g., arcuately concave) or angled transition surface portion that extends or transitions to/from the threaded shaft portion 248. As also shown in FIGS. 27, 32, 39 and 42, the inner side 252 of the head portion 246 may also include an annular groove or depression portion 260 that extends between an inner or back side of an outer peripheral row of teeth or projections 262 and the transition portion. The annular depression 260 may include an annular planar or flat bottom surface, and arcuately concave side portions formed by the transition surface portion and the inner sides of peripheral teeth 262. The annular depression 260 may be configured to contain or be filled by bone material when the retention device 210 is tightened/compressed onto the adjacent bone.

As also shown in FIGS. 26, 27, 30-32, 39, 40, 42 and 43, the peripheral row of teeth 262 may define the circular outer periphery of the head portion 246. In some embodiments, the inner side 252 of the head portion 246 may only comprise a single row of the teeth 262 at the periphery thereof. The inner or back side of the teeth 262 may be arcuate (e.g., arcuately concave) and/or planar. The outer side of the teeth 262 may planar and/or arcuate (e.g., arcuately convex or concave). The teeth 232 may define an axis that is aligned with the axis of the bone anchor member 214. Stated differently, the teeth 232 may extend along a direction that is aligned or parallel to the axis of the bone anchor member 214 (and thereby perpendicular or normal to the head portion 246).

As also shown in FIGS. 26, 27, 30, 31, 39 and 43, the peripheral row of teeth 262 may be angled laterally or annularly/circumferentially. The teeth 262 may be "aggressive" such that the teeth 262 (e.g., the front faces thereof) are oriented at an acute angle. The teeth 262 may be oriented (e.g., angled) annularly/circumferentially in a direction that opposes the direction of the thread of the shaft portion 248. In this way, the teeth 262 may be configured to dig into bone and resist rotation of the bone anchor member 214 in a direction that would unscrew or threadably de-couple from the threaded shaft 218 of the tack member 212 (when coupled therewith and implanted/installed in/on a bone).

Figure 50:
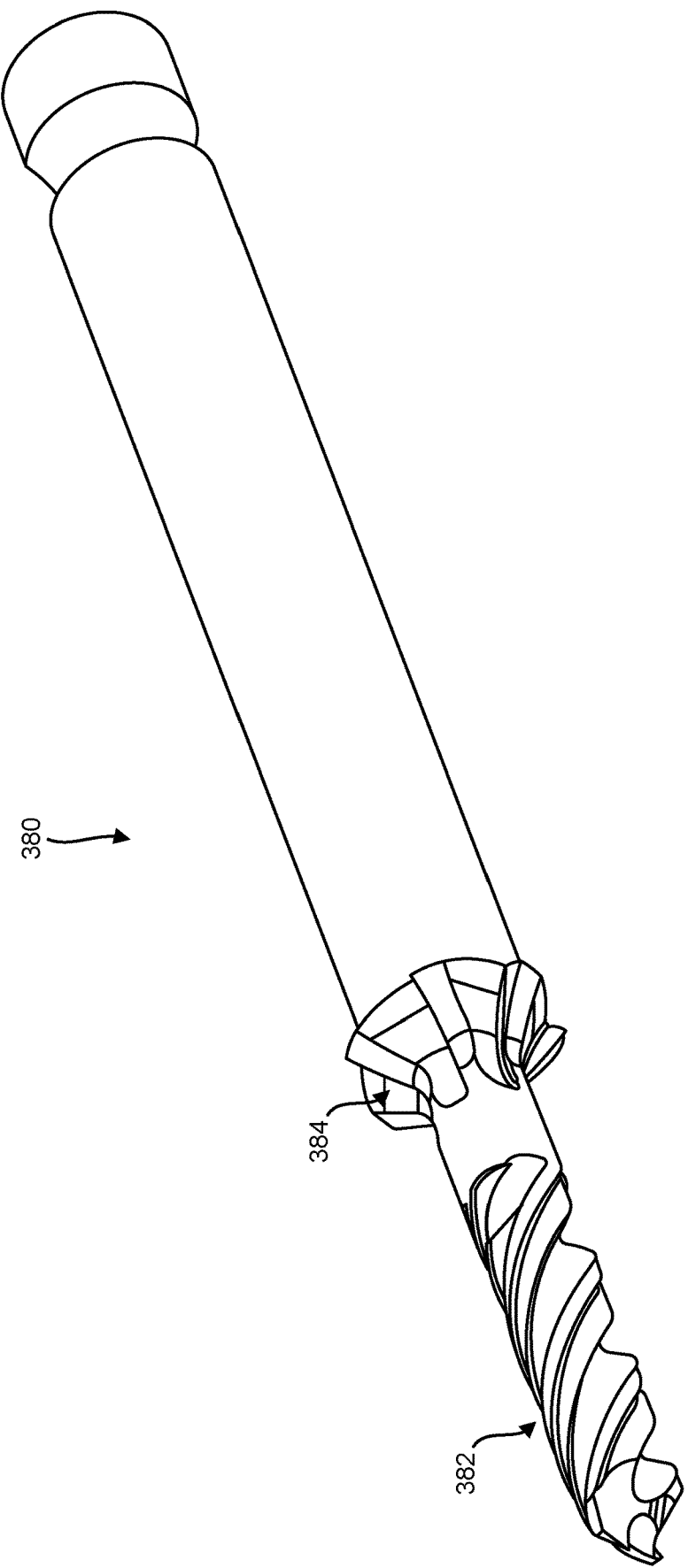
FIG. 50 illustrates a perspective view of an exemplary drill bit for preparing a counter-sunk through hole in a bone for use with the soft tissue and bone retention device of FIGS. 26-32, in accordance with an aspect of the present disclosure.
Figure 51:
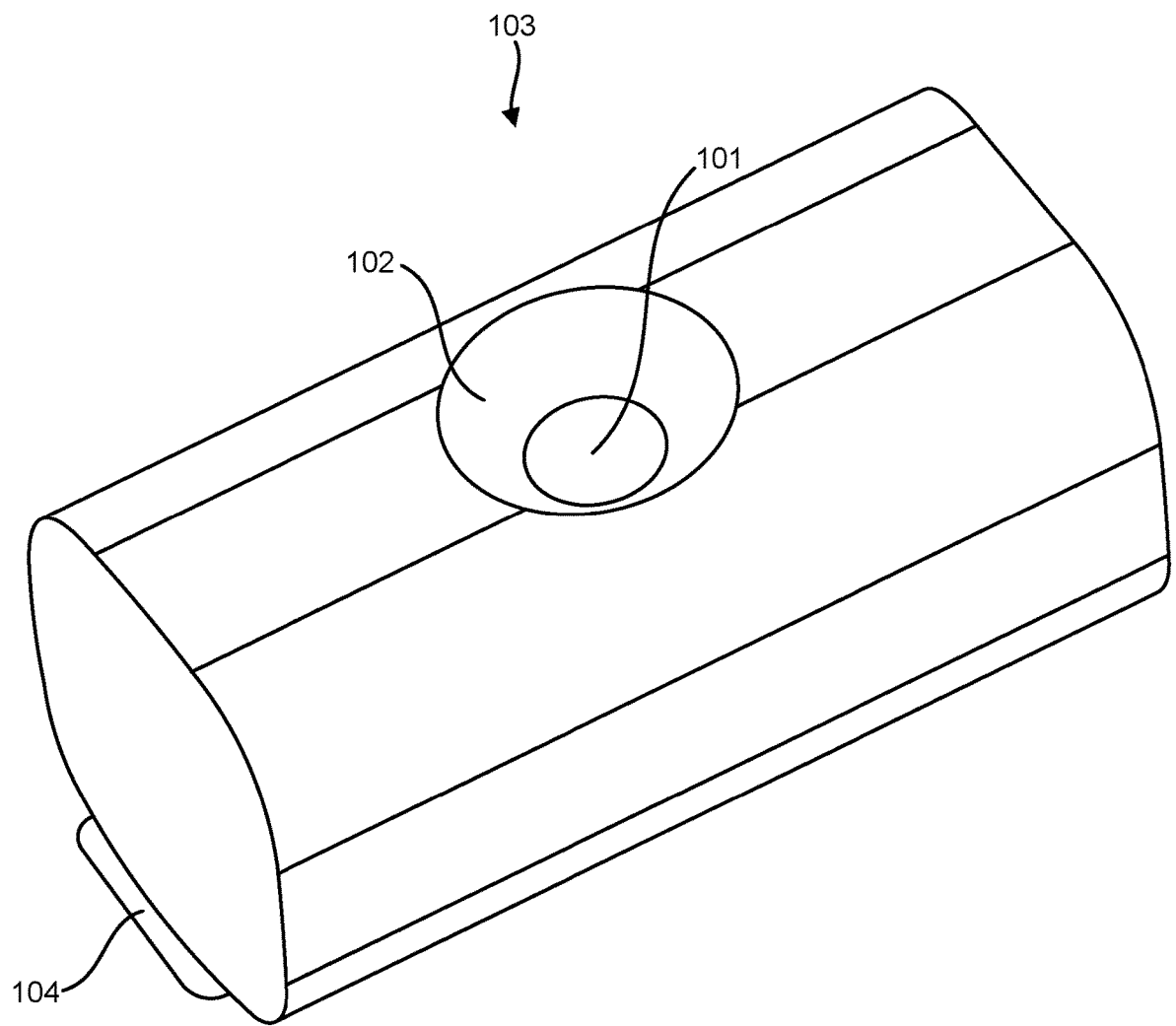
FIG. 51 illustrates an elevational perspective view of an exemplary bone with a counter-sunk through hole prepared via the drill bit of FIG. 50 and adjacent soft tissue, in accordance with an aspect of the present disclosure.

An exemplary soft tissue retention drill bit 380 as shown in FIG. 50 may be utilized to form a soft tissue retention aperture 101 in a bone 103 as shown in FIG. 51. As shown in FIGS. 50 and 51, the drill bit 380 may include an aperture or through hole cutting portion 382 configured to form the aperture or through hole 101 that extends through the bone 103 via rotation of the cutting portion 382. As also shown in FIGS. 50 and 51, the drill bit 380 may include a countersink portion 384 that is configured to form a countersink 102 in the through hole 101 on the side of the bone 103 that opposes soft tissue 104 via rotation of the countersink portion 384.

The cannulated opening 240 and drive aperture 224 of the soft tissue tack member 212, and the cannulated opening 240 and drive aperture 254 of the bone anchor member 214, may facilitate assembly and implantation of the soft tissue retention device 210 via instrumentation, as shown in FIGS. 44-56. The instrumentation may include a tack member drive and guide instrument 370 configured to facilitate assembly and implantation of the soft tissue retention device 210, and the selection of a properly sized bone anchor member 214 for a specific bone 103, as shown in FIGS. 44-46 and 54-56.

As shown in FIGS. 44-46 and 54-56, the exemplary tack member drive and guide instrument 370 includes a guide and sizing wire, post, member or portion 371 extending from a drive or torque projection 372 at an end of a handle portion 373. As shown in FIGS. 44, 45, 54, 55, the handle portion 373 of the instrument 370 includes an aperture, annulus, ring, loop, band, or the like that allows a user to hold and manipulate the installation instrument 370, potentially with one hand. For example, the aperture of the handle portion 373 of the instrument 370 may be configured (e.g., sized and shaped) to allow a user to extend a digit therethrough, such as a user's thumb therethrough. In this way, a user can extend their thumb (for example) through the aperture of the instrument 370 and use at least a portion of the rest of their hand/fingers to engage the patient (e.g., engage a portion of the patient's foot or other body portion on an opposing side of the portion engaged (indirectly or directly) by the instrument 370) (see, for example, FIG. 25).

Figure 54:
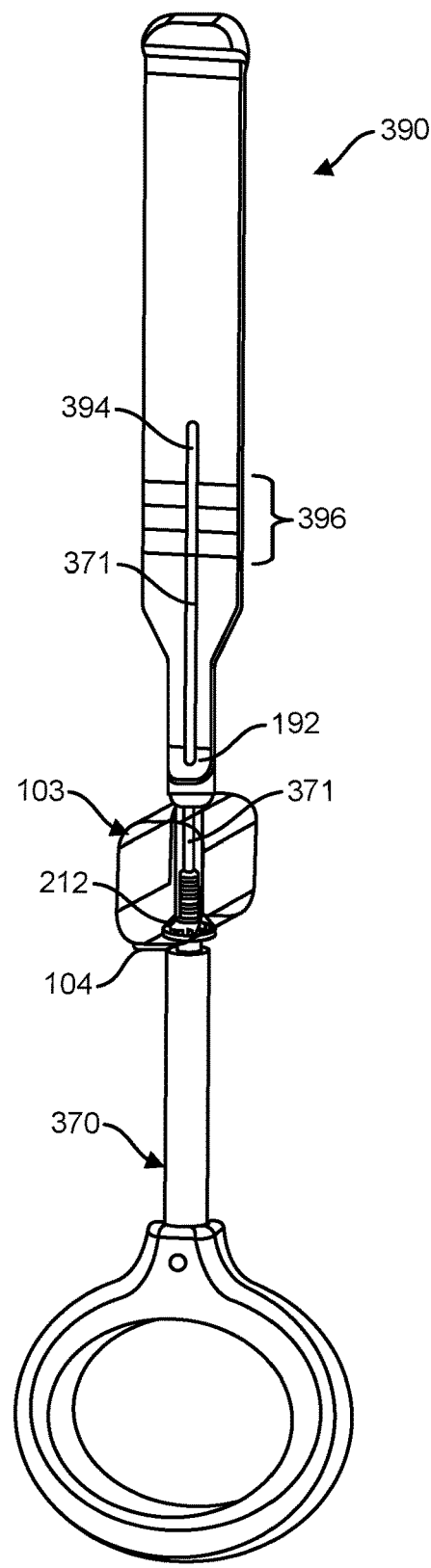
FIG. 54 illustrates a perspective view of the soft tissue tack member of FIGS. 26-32 extending through the soft tissue and held within the through hole of the prepared bone of FIG. 51 via the tack member drive and guide instrument of FIGS. 44-46 and the bone anchor member sizing guide of FIGS. 52 and 53 utilized therewith to determine a properly sized bone anchor member, in accordance with an aspect of the present disclosure.
Figure 55:
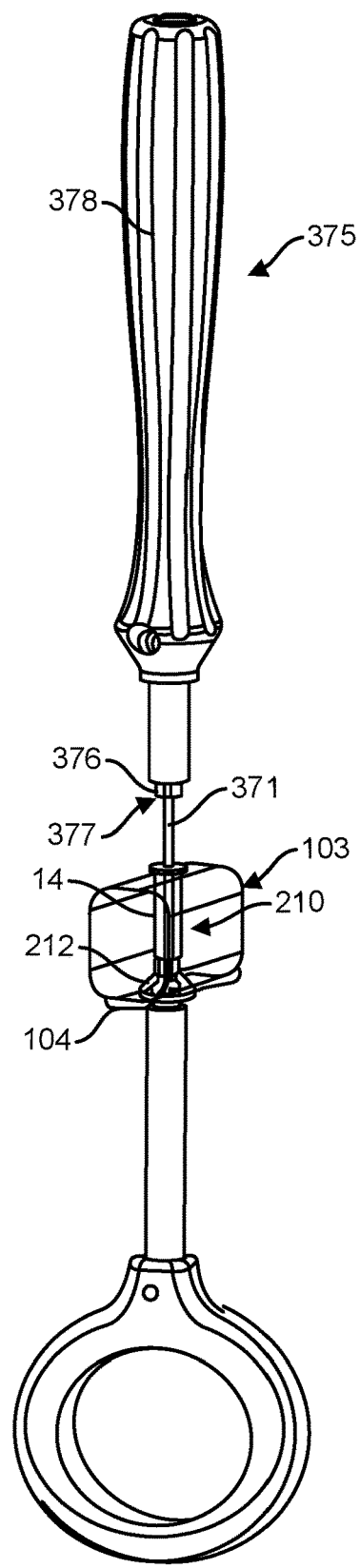
FIG. 55 illustrates a perspective view of the soft tissue tack member, the soft tissue, the prepared bone, and the tack member drive and guide instrument of FIG. 54 with the bone anchor member of FIGS. 26-32 being coupled to the soft tissue tack member within the through hole of the bone via the bone anchor member drive and guide instrument of FIGS. 47-49, in accordance with an aspect of the present disclosure.
Figure 56:
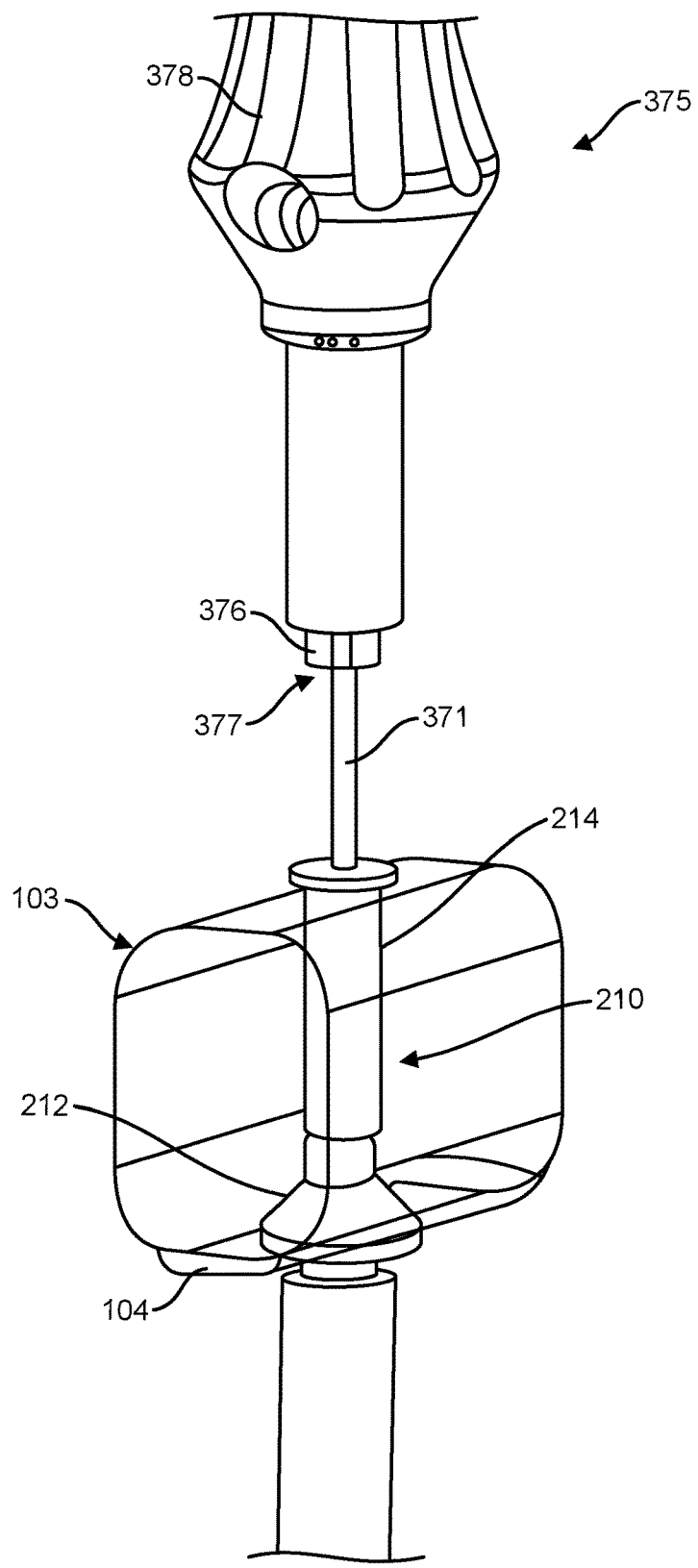
FIG. 56 illustrates an enlarged perspective view of a portion of the arrangement of the soft tissue tack member, the soft tissue, the prepared bone, the tack member drive and guide instrument and the bone anchor member drive and guide instrument of FIG. 55.
Figure 57:
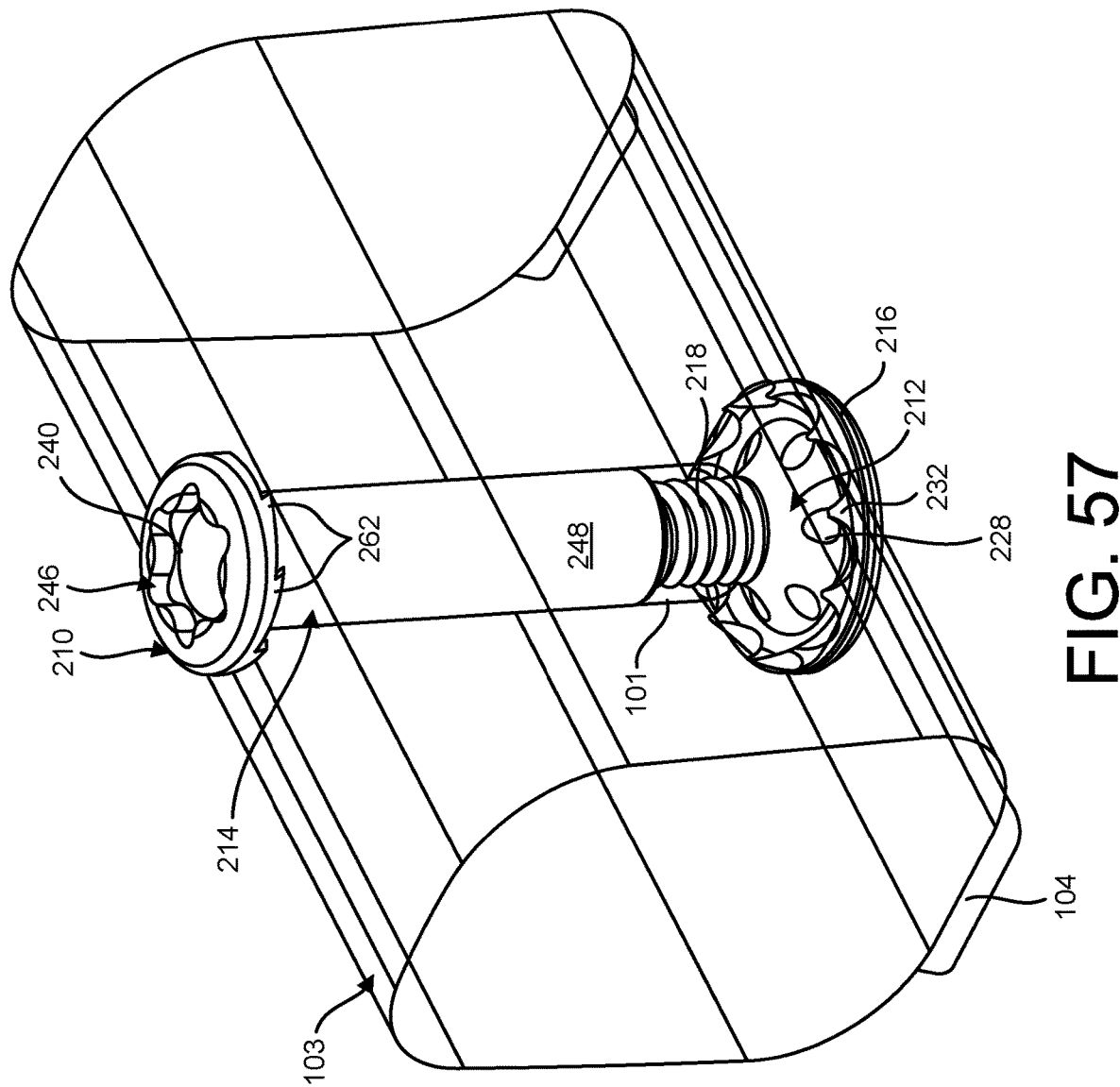
FIG. 57 illustrates an elevational perspective view of the coupled soft tissue tack member and bone anchor member retaining the soft tissue to the bone of FIGS. 55 and 56 with the instrumentation removed, in accordance with an aspect of the present disclosure.
Figure 58:
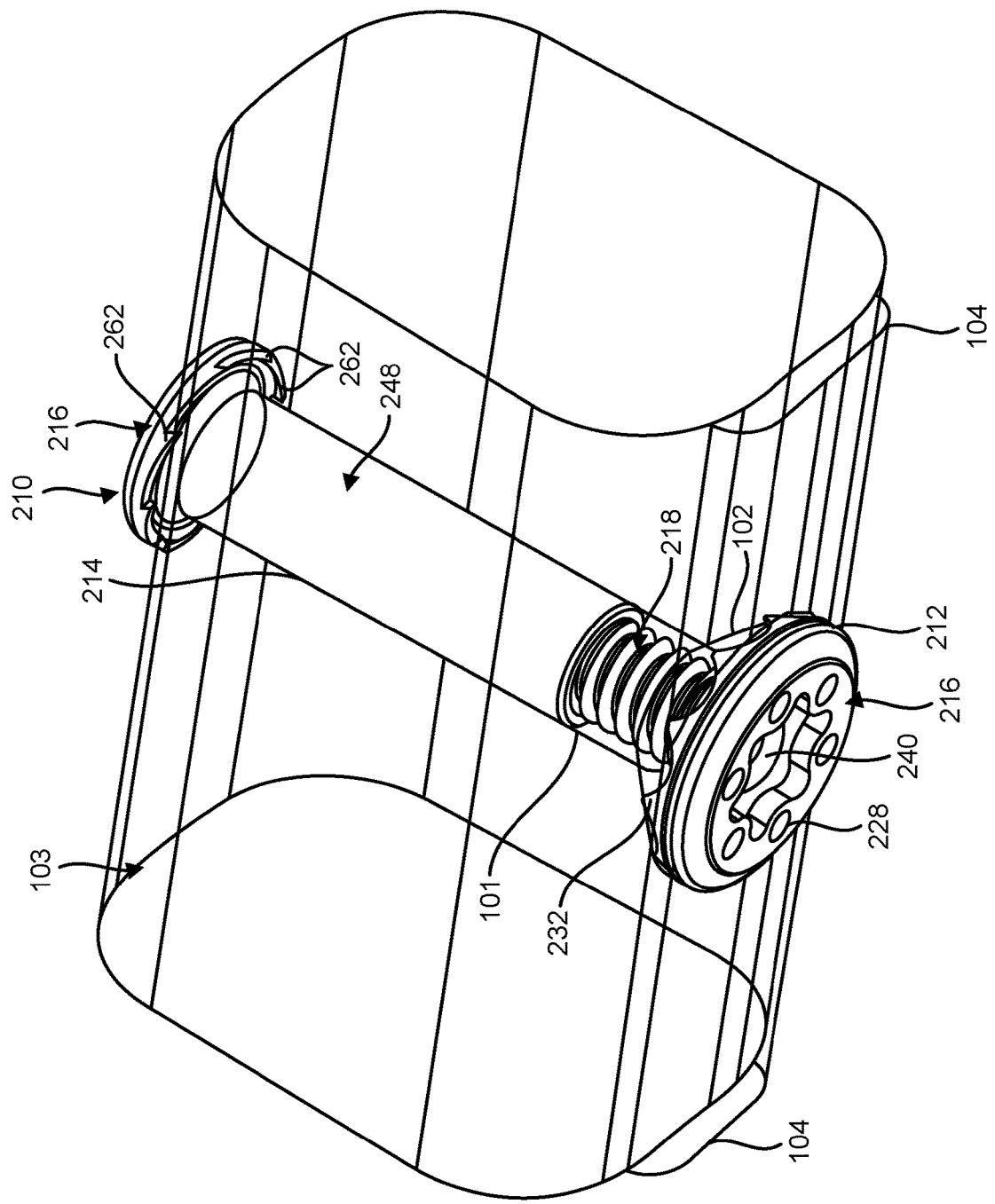
FIG. 58 illustrates a bottom perspective view of the coupled soft tissue tack member and bone anchor member retaining the soft tissue to the bone of FIG. 57.
Figure 59:
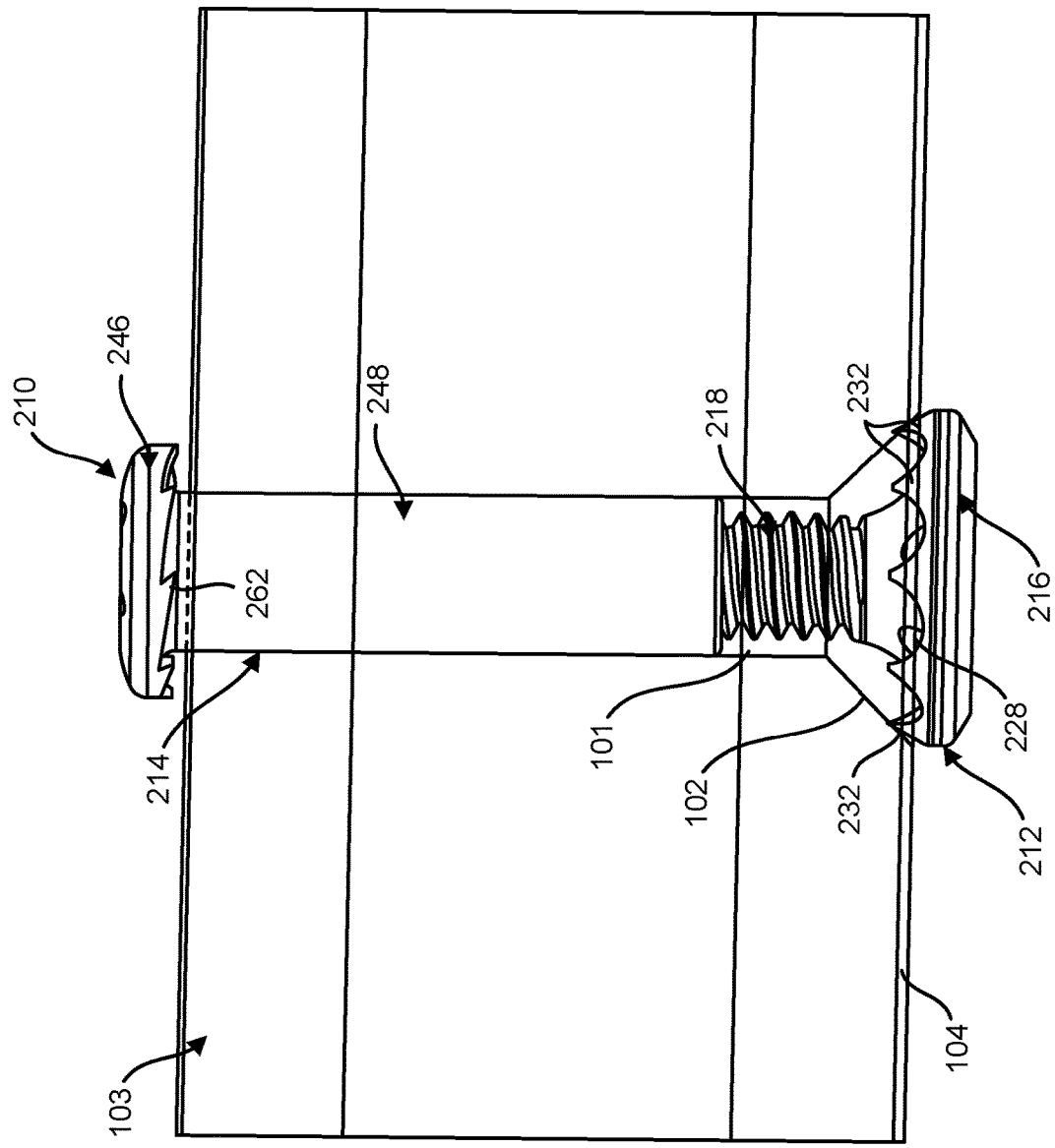
FIG. 59 illustrates a side view of the coupled soft tissue tack member and bone anchor member retaining the soft tissue to the bone of FIG. 57.
Figure 60:
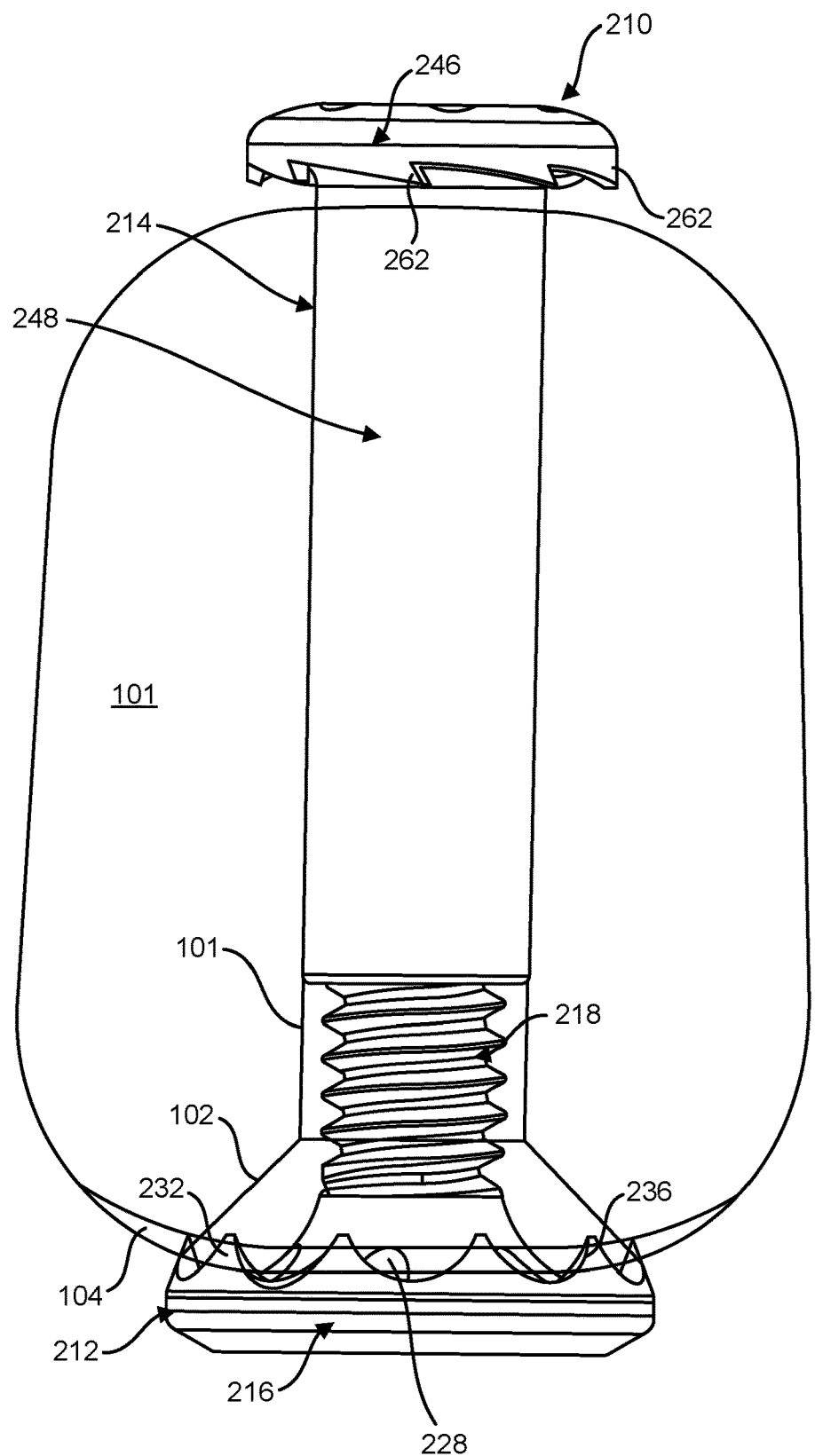
FIG. 60 illustrates an end view of the coupled soft tissue tack member and bone anchor member retaining the soft tissue to the bone of FIG. 57.

The guide and sizing wire 371 is configured to extend through the cannulated openings 240 of the soft tissue tack member 212 and the bone anchor member 214 (i.e., the cannulated opening 240 of the soft tissue retention device 210). The guide and sizing wire 371 is of a fixed predetermined length such that the free end or tip of the wire 371 is at a fixed pre-defined distance from the drive projection 372. The drive projection 372 is configured to mate or extend within the drive aperture 224 of the soft tissue tack member 212. As such, the drive projection 372 may be of the same non-circular cross-sectional shape and size as the drive aperture 224 of the soft tissue tack member 212. The handle portion 373 may be fixed to the drive projection 372 such that torque/rotation (e.g., manual rotation) of the handle portion 373 rotates the drive projection 372 (or that prevention of rotation of the handle portion 373 prevents rotation of the drive projection 372). In this way, as shown in FIGS. 54-56, the tack member drive and guide instrument 370 may be manipulated such that the guide and sizing wire 371 is passed/positioned into and through the cannulated opening 240 of the soft tissue tack member 212 (from the head portion 216 thereof) and the drive projection 372 is positioned/mated within the drive aperture 224. The handle portion 373 can then be utilized to support and manipulate the soft tissue tack member 212 to position the soft tissue tack member 212 through soft tissue and into the aperture 101 of the bone 103 with the guide wire portion 371 extending through the aperture 101, and to ultimately rotate/apply torque to the soft tissue tack member 212 (or prevent rotation thereof), as shown in FIGS. 54-56.

Figure 47:
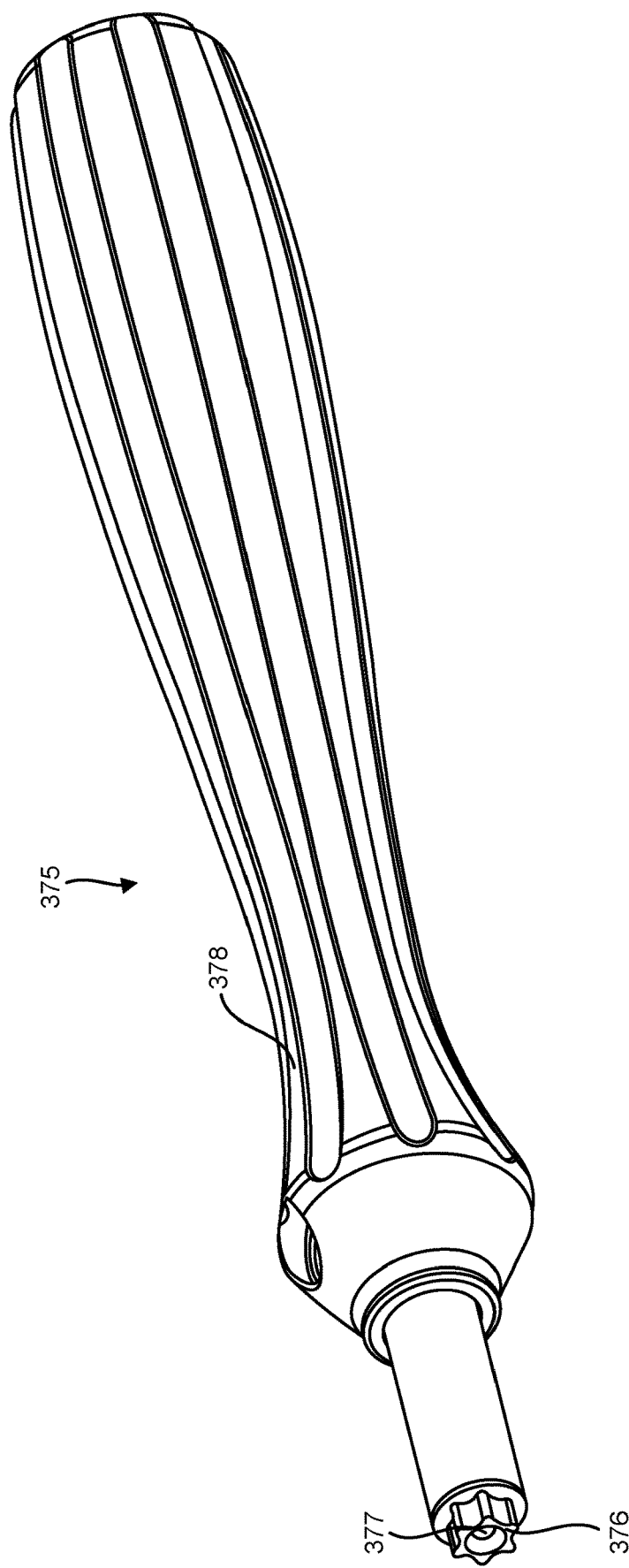
FIG. 47 illustrates a perspective view of an exemplary bone anchor member drive and guide instrument, in accordance with an aspect of the present disclosure.
Figure 48:
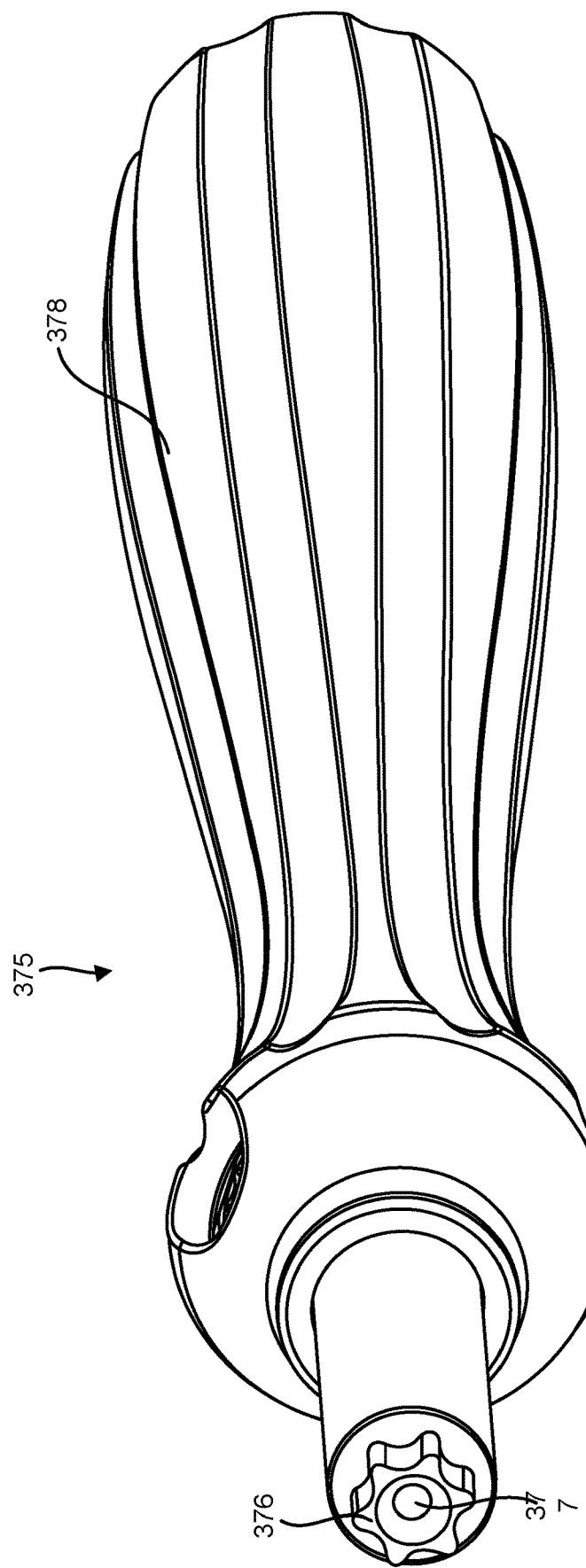
FIG. 48 illustrates another perspective view of the bone anchor member drive and guide instrument of FIG. 47.
Figure 49:
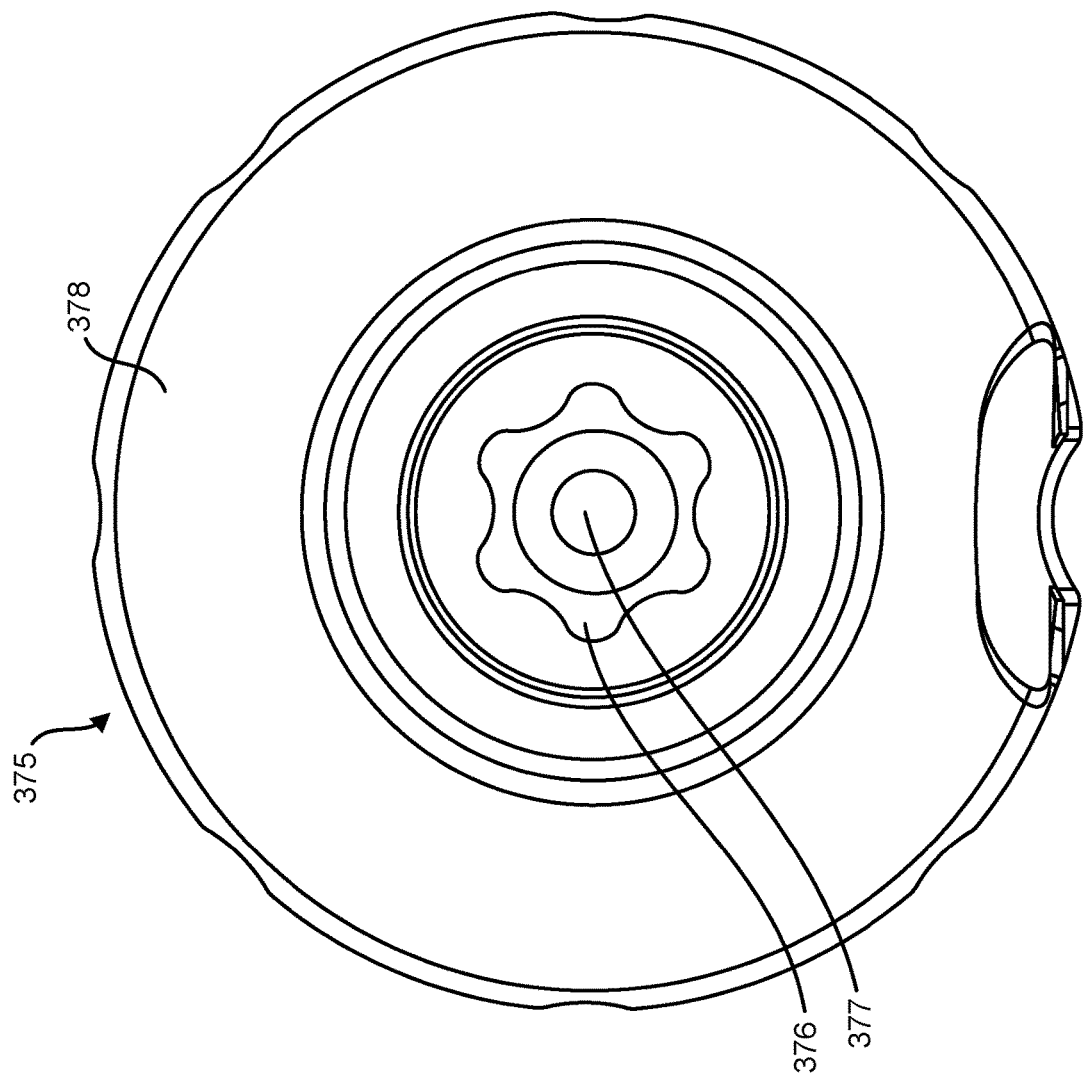
FIG. 49 illustrates a drive end view of the bone anchor member drive and guide instrument of FIG. 47.

An exemplary bone anchor member drive and guide instrument 375 configured to facilitate assembly and implantation of the cannulated soft tissue retention device 210 is shown in FIGS. 47-49, 55 and 56. As shown in FIGS. 47-49, 55 and 56, the anchor member drive and guide instrument 375 includes a drive or torque projection 376 provided at an end of a handle portion 378. As shown in FIGS. 47-49, the anchor member drive and guide instrument 375 also includes a cavity or opening 377 extending from and into the drive projection 376 that is configured to accept or house the guide and sizing wire 371 of the tack member drive and guide instrument 370 therein. In this way, the cavity 377 of the anchor member drive and guide instrument 375 is configured to allow the guide and sizing wire 371 of the tack member drive and guide instrument 370 to extend therein.

The drive projection 376 is configured to mate or extend within the drive aperture 254 of the bone anchor member 214. As such, the drive projection 376 may be of the same non-circular cross-sectional shape and size as the drive aperture 254 of the bone anchor member 214. The handle portion 378 may be fixed to the drive projection 376 such that torque/rotation (e.g., manual rotation) of the handle portion 378 rotates the drive projection 376 (or that prevention of rotation of the handle portion 378 prevents rotation of the drive projection 376). In this way, as shown in FIGS. 55 and 56, the bone anchor member drive and guide instrument 375 (and the tack member drive and guide instrument 370) may be manipulated such that the drive projection 376 is positioned/mated within the drive aperture 254 of the bone anchor member 214. The handle portion 378 can then be utilized to support and manipulate the bone anchor member 214 to position the guide and sizing wire 371 of the tack member drive and guide instrument 370 into the cavity 377 of the bone anchor member drive and guide instrument 375 to align the soft tissue tack member 212 and the bone anchor member 214 (and align the bone anchor member 214 with the aperture 101), position the bone anchor member 214 into the aperture 101 of the bone 103, and to ultimately rotate/apply torque to the bone anchor member 214 (or prevent rotation thereof) to threadably couple the shaft portion 218 of the soft tissue tack member 212 and the shaft portion 248 of the bone anchor member 214 and compress the soft tissue retention device on the bone 103, as shown in FIGS. 55 and 56.

Figure 52:
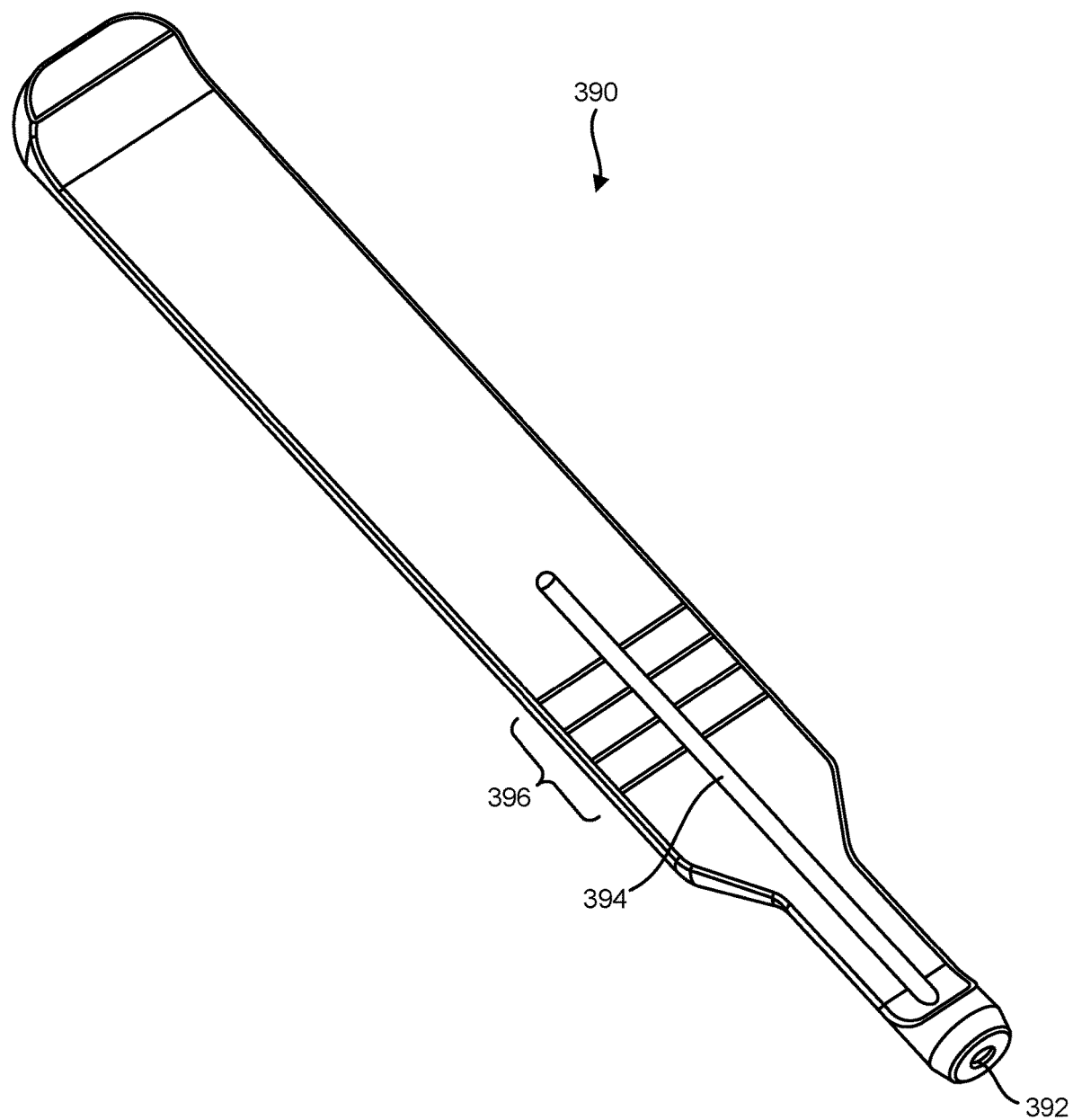
FIG. 52 illustrates an elevational perspective view of an exemplary bone anchor member sizing guide, in accordance with an aspect of the present disclosure.
Figure 53:
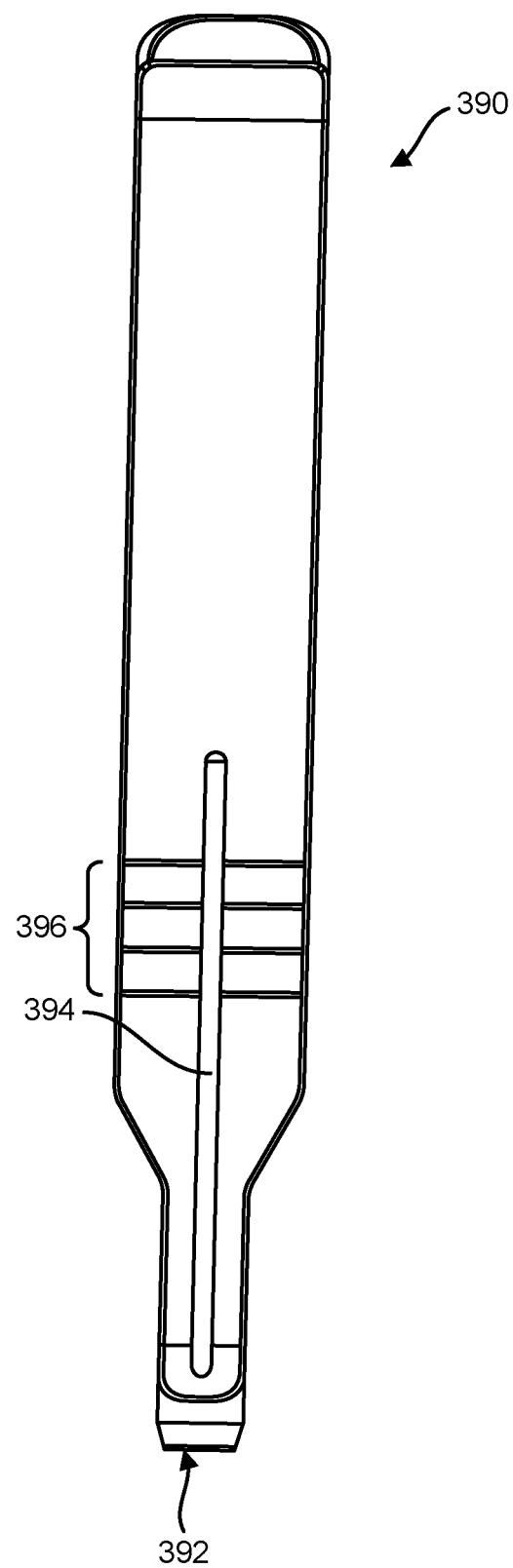
FIG. 53 illustrates a front view of the bone anchor member sizing guide of FIG. 52.

As noted above, the tack member drive and guide instrument 370 may be utilized to facilitate the selection/determination of a properly sized bone anchor member 214 for the specific bone 103. As shown in FIGS. 52-54, a bone anchor member sizing guide 390 may be configured to be utilized with the tack member drive and guide instrument 370 to facilitate the selection/determination of a properly sized bone anchor member 214 for the specific bone 103. The bone anchor member sizing guide 390 may include an opening or through hole/aperture 392 at an end or tip of the bone anchor member sizing guide 390 that is configured to accept the wire portion 371 of the tack member drive and guide instrument 370 therein/therethrough (see FIG. 54). The bone anchor member sizing guide 390 may also include a groove, indentation and/or marking 394 that aligns with and accepts the portion of the wire portion 371 of the tack member drive and guide instrument 370 that passes through the opening 392, as shown in FIG. 54. As shown in FIG. 54, the bone anchor member sizing guide 390 also includes a plurality of sizing markings 396 proximate to the groove 394 that correspond to differently sized bone anchor members 214. For example, the plurality of sizing markings 396 of the bone anchor member sizing guide 390 may correspond to bone anchor members 214 with differing axial/longitudally sized shaft portions 248 (with the head portions 246 being of the same size or different sizes).

As shown in FIG. 54, the bone anchor member sizing guide 390 may thereby be utilized to determine a properly sized bone anchor member 214 for a bone 103 which includes the soft tissue tack member 212 positioned in the through aperture 101 thereof (and through soft tissue) (such as on/in abutment with the countersink 102 in the bone 103) via the tack member drive and guide instrument 370. The tip or end of the bone anchor member sizing guide 390 may be positioned on/in abutment with the opposing side of the bone 103 as the soft tissue and soft tissue tack member 212 with the wire portion 371 of the tack member drive and guide instrument 370 extending through the opening 392 and along the groove 394, as shown in FIG. 54. The end of the wire portion 371 of the tack member drive and guide instrument 370 may substantially align (or most closely align) with one of the size indications 396. The size indications 396 thereby indicate how thick the bone 103 is (or how thick/long the through aperture 101 is), and a correspondingly sized bone anchor member 214 that is configured to extend through the aperture 101 and to the soft tissue tack member 212 (to threadably mate with the soft tissue tack member 212, as discussed above), as shown in FIGS. 54-56.

As shown in FIGS. 57-60, with a properly sized bone anchor member 214 selected/determined, the bone anchor member 214 may be threadably coupled to the soft tissue tack member 212 and the torqued/drawn together (via rotation) to compress the head portion 216 of the soft tissue tack member 212 against the soft tissue 104 (see FIGS. 59 and 60) and bone 103 and the head portion 246 of the bone anchor member 214 against the bone 103. As noted above, the teeth 232 of the head portion 216 of the soft tissue tack member 212 may engage (and potentially penetrate into) the soft tissue 104 (and potentially the bone 103) to retain the soft tissue 104 (see FIGS. 59 and 60), and the teeth 262 of the bone anchor member 214 may engage (and potentially penetrate into) the bone 103, when the bone anchor member 214 and the soft tissue tack member 212 are torqued/drawn together as shown in FIGS. 57-60. As also discussed above, the through holes 228 in the head portion 216 of the soft tissue tack member 212 may allow the soft tissue 104 (see FIGS. 59 and 60) to extend therein to securely retain the soft tissue 104 when the bone anchor member 214 and the soft tissue tack member 212 are torqued/drawn together, as shown in FIGS. 57-60.

Figure 61:
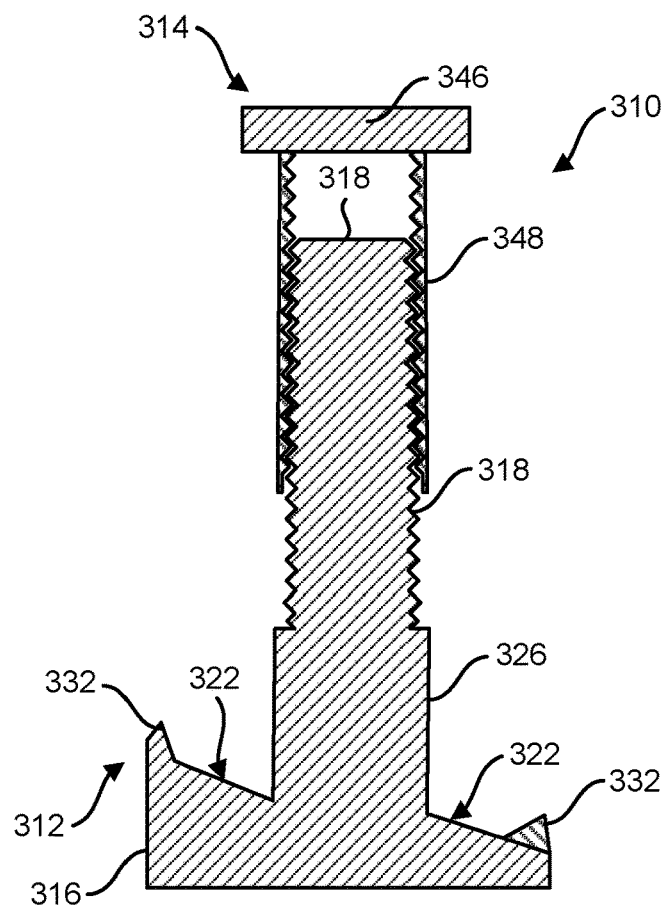
FIG. 61 illustrates a side cross-sectional view of another exemplary soft tissue and bone retention device, in accordance with an aspect of the present disclosure.
Figure 62:
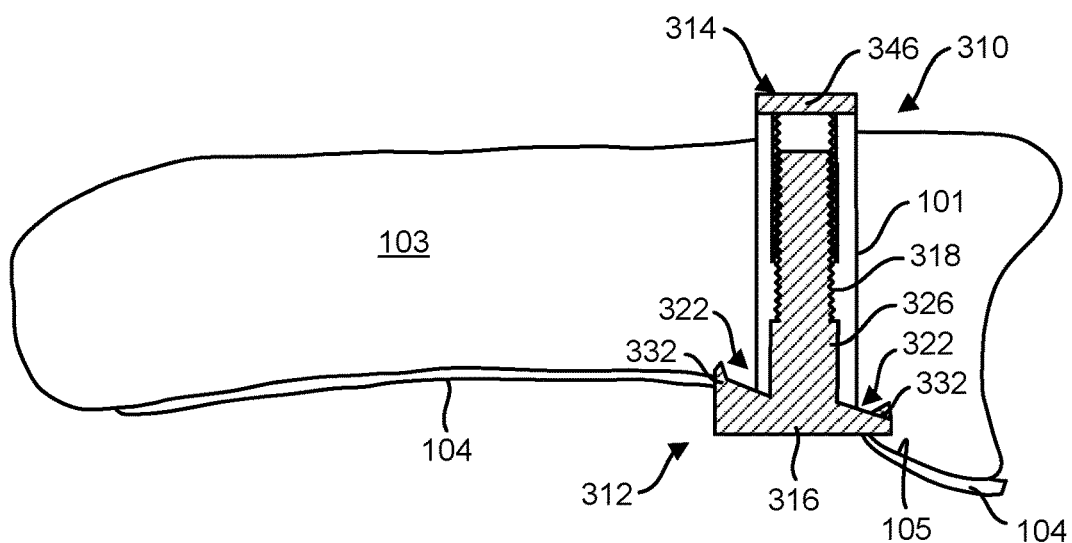
FIG. 62 illustrates a cross-sectional view of the soft tissue and bone retention device of FIG. 61 retaining a soft tissue to a bone, in accordance with an aspect of the present disclosure.

FIGS. 61 and 62 illustrate another exemplary embodiment of a soft tissue retention device or system 310 configured to couple, retain, fix, and/or secure soft tissue 104 to an associated or desired bone 103 (such as, but not limited to, a relatively small bone (e.g., a bone of the foot or hand)). In some embodiments, the soft tissue retention device 310 may be particularly configured and/or advantageous for retention of a flexor digitorum longus tendon and an associated bone 103, such as, but not limited to, the plantar aspect of a proximal phalangeal base (bone) particularly, but not necessarily, for the correction of a toe contracture. However, the soft tissue retention device 310 may be configured and/or effectively utilized to retain, couple or fix any soft tissue 104 (e.g., a tendon, ligament or the like) to any bone 103 (e.g., any relatively small bone, such as a phalange, metatarsal or metacarpal bone) of a patient (e.g., a human patient).

Aspects of the soft tissue retention device 310 may be configured the same as or similar to aspects of the soft tissue retention device 100 and/or the soft tissue retention device 210 described above. For example, the soft tissue retention device 310 may include a soft tissue tack portion or member 312 and a bone anchor portion or member 314 configured to threadably couple within a through aperture 101 of the bone 103 to retain or fix the associated soft tissue 104 to the bone 103, as described above. The description of such common aspects, elements and/or functions of soft tissue retention device 310 that are the same or similar in structure and/or function, at least in part, to that of the soft tissue retention device 100 and/or the soft tissue retention device 210 are not repeated herein for brevity sake. However, it is specifically contemplated that the soft tissue retention device 310 may include components, aspects, configurations, functions or processes that are the same or similar to that of the soft tissue retention device 100 and/or the soft tissue retention device 210 (even if not shown/depicted in FIGS. 61 and 62), and the description above directed thereto (and the alternative embodiments thereof) equally applies to the soft tissue retention device 310.

As shown in FIGS. 61 and 62, the soft tissue retention device 310 differs from the soft tissue retention device 100 and the soft tissue retention device 210 in the configuration of the head portion 316 and shaft portion 318 of the soft tissue tack member 312. As shown in FIGS. 61 and 62, at least the inner side 322 of the head portion 316 is angled with respect to the shaft portion 318 (such as opposed to being oriented normal thereto) such that a first portion of the inner side 322 of the head portion 316 positioned on a first lateral side of the shaft portion 318 is positioned further toward the bone anchor portion or member 314 than a second portion of the inner side 322 of the head portion 316 positioned on a second lateral side of the shaft portion 318. The inner side 322 of the head portion 316, including the teeth or projections 232 thereof, may thereby be sloped from the first lateral side to the second lateral side thereof.

In some embodiments, the inner side 322 of the head portion 316 may extend along or define (e.g., the tips of the teeth 232 may define) a plane that is angled to an axis of the shaft portion 318 (and potentially a transition portion 326, as described further below), such as the long axis of the portion 318. In some such embodiments, the plane of the head portion 316 may be angled 45 degrees or less from normal to the long axis of the shaft portion 318 (and potentially a transition portion 326) (e.g., the first portion of the inner side 322 of the head portion 316 may be angled within the range of about 45 degrees to about 90 degrees from the long axis of the shaft portion 318, and the second portion of the inner side 322 of the head portion 316 may be angled within the range of about 90 degrees and about 135 degrees from the long axis of the shaft portion 318). In some other such embodiments, the plane of the head portion 316 may be angled 30 degrees or less from normal to the long axis of the shaft portion 318 (and potentially a transition portion 326) (e.g., the first portion of the inner side 322 of the head portion 316 may be angled within the range of about 60 degrees to about 90 degrees from the long axis of the shaft portion 318, and the second portion of the inner side 322 of the head portion 316 may be angled within the range of about 90 degrees and about 120 degrees from the long axis of the shaft portion 318). In some other such embodiments, the plane of the head portion 316 may be angled 15 degrees or less from normal to the long axis of the shaft portion 318 (and potentially a transition portion 326) (e.g., the first portion of the inner side 322 of the head portion 316 may be angled within the range of about 75 degrees to about 90 degrees from the long axis of the shaft portion 318, and the second portion of the inner side 322 of the head portion 316 may be angled within the range of about 90 degrees and about 105 degrees from the long axis of the shaft portion 318).

As shown in FIG. 62, it may be desirable to retain, attach or fix a soft tissue 104 to a sloped or angled outer surface 105 of a bone 103. For example, it may be desirable to implant the device 310 in a portion of a bone 104 that lies on a metaphyseal slope 105. In such embodiments, the angulation or sloped inner side 322 of the head portion 316 of the soft tissue tack member 312 may extend substantially parallel to or approximate the sloped or angled outer surface 105 of the bone 103 when the shaft portion 318 is positioned within the through hole 101 and threadably coupled with the bone anchor member 314, as shown in FIG. 62. In this way, at least a substantial majority or entirety of the inner side 322 of the head portion 316 may engage and grip the soft tissue 104 and fix and compress the soft tissue 104 to the angled outer surface 105 of the bone 103, as shown in FIG. 63.

In some embodiments, the head portion 316 of the soft tissue tack member 312 may be integral or fixedly attached to the shaft portion 318. In some other embodiments, as shown in FIGS. 61 and 62, the head portion 316 may be assembled with the shaft portion 318 via the transition portion 326 of the head portion 316, potentially after the shaft portion 318 is (threadably) coupled with the bone anchor member 314 and/or positioned within the through hole 101 of the bone 103. For example, the transition portion 326 may be slip fit over the shaft portion 318, the transition portion 326 may be swaged over a diameter of the shaft portion 318, the transition portion 326 may be forced or clicked over a lip or boss of the shaft portion 318 (e.g., such that the lip or boss is positioned within an indentation in the transition portion 326), or the transition portion 326 may threadably coupled with the shaft portion 318.

Figure 63:
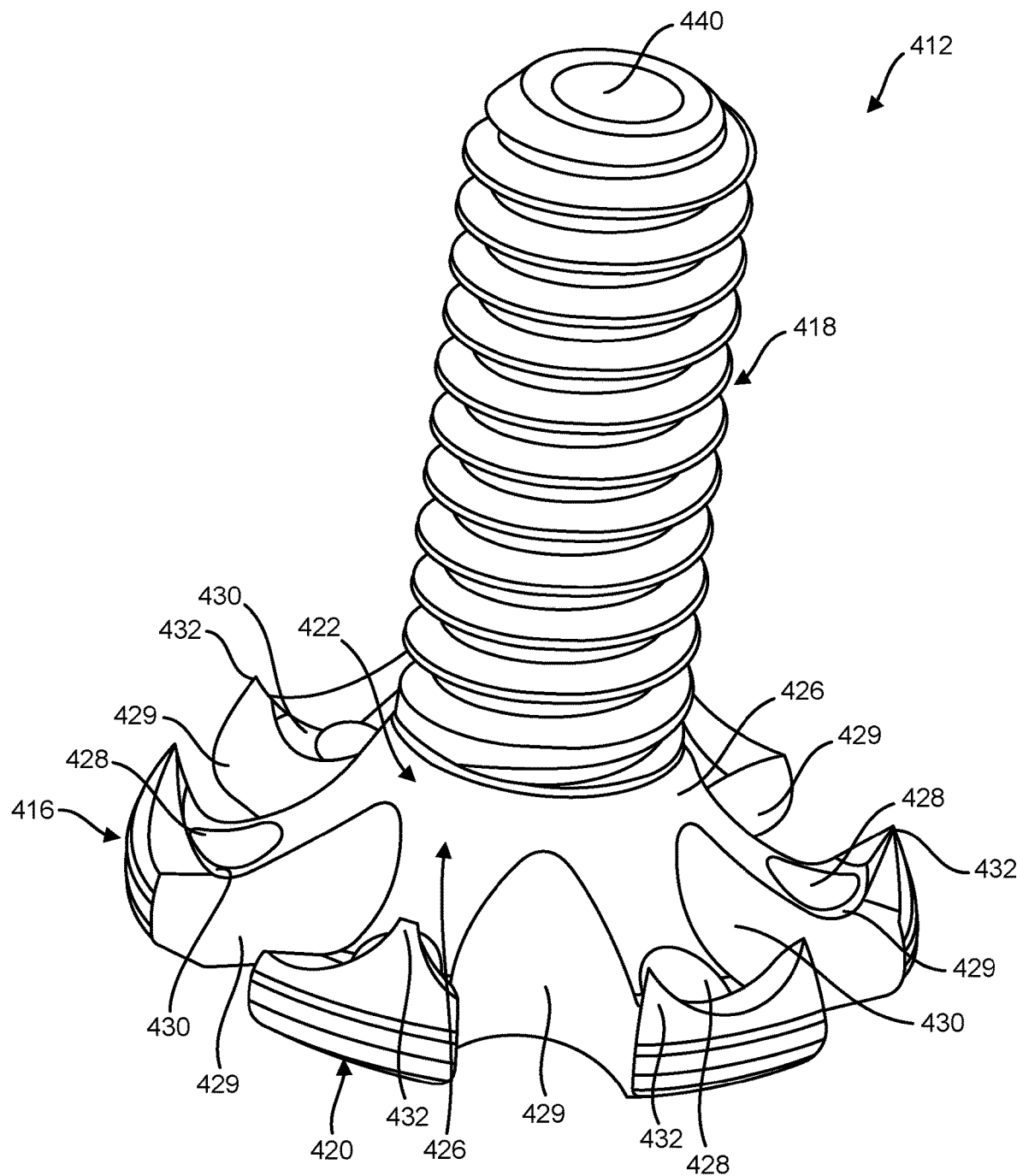
FIG. 63 illustrates an elevational perspective view of another exemplary soft tissue tack member of a tissue and bone retention device, in accordance with an aspect of the present disclosure.

FIG. 63 illustrates another exemplary embodiment of a soft tissue tack member 412 for a soft tissue retention device or system configured to couple, retain, fix, and/or secure soft tissue to an associated bone (such as, but not limited to, a relatively small bone (e.g., a bone of the foot or hand)). In some embodiments, the soft tissue tack member 412 may be particularly configured and/or advantageous for retention of a flexor digitorum longus tendon and an associated bone, such as, but not limited to, the plantar aspect of a proximal phalangeal base (bone) particularly, but not necessarily, for the correction of a toe contracture. However, the soft tissue tack member 412 may be configured and/or effectively utilized to retain, couple or fix any soft tissue (e.g., a tendon, ligament or the like) to any bone (e.g., any relatively small bone, such as a phalange, metatarsal or metacarpal bone) of a patient (e.g., a human patient).

Aspects of the soft tissue tack member 412 may be configured the same as or similar to aspects of the soft tissue tack member 10, the soft tissue tack member 212 and/or the soft tissue tack member 312 described above. For example, the soft tissue tack member 412 may be configured to threadably couple with a bone anchor member within a through aperture of the bone to retain or fix the associated soft tissue to the bone, as described above. The description of such common aspects, elements and/or functions of the soft tissue tack member 412 that are the same or similar in structure and/or function, at least in part, to that of the soft tissue tack member 10, the soft tissue tack member 212 and/or the soft tissue tack member 312 are not repeated herein for brevity sake. However, it is specifically contemplated that the soft tissue tack member 412 may include components, aspects, configurations, functions or processes that are the same or similar to that of the soft tissue tack member 10, the soft tissue tack member 212 and/or the soft tissue tack member 312 (even if not shown/depicted in FIG. 63), and the description above directed thereto (and the alternative embodiments thereof) equally applies to the soft tissue tack member 412.

As shown in FIG. 63, the soft tissue tack member 412 differs from the soft tissue tack member 10, the soft tissue tack member 212 and the soft tissue tack member 312 in that the head portion 416 includes radially-extending indentations, cutaways, slots or openings 429 extending from the outer periphery of the head portion 416 inwardly toward the axis of the tack member 412 (e.g., toward the axis of the shaft portion 418 and/or the head portion 416). In this way, the head portion 416 may be divided by the openings 429 into a plurality of radially-extending angularly (or annularly/circumferentially) spaced portions (i.e., finger-like portions).

Each radially-extending "finger" portion of the head portion 416 (between adjacent openings 429) may include at least one tooth 432, annular depression 430, and/or at least one through hole 428, as shown in FIG. 63. The radially-extending "finger" portions may be bendable or deformable, such as elastically deformable. In use, when the soft tissue tack member 412 is coupled with a bone anchor member as described above, the head portion 416 may compress soft tissue against the outer surface of a bone such that the soft tissue extends/is forced into the openings 429 between the radially-extending "finger" portions (and potentially into the through holes 428, if present). Further, the radially-extending "finger" portions of the head portion 416 may deform or bend to accommodate or adapt to the surface shape or profile of the outer surface of the bone and/or the thickness of the soft tissue, for example.

Figure 64:
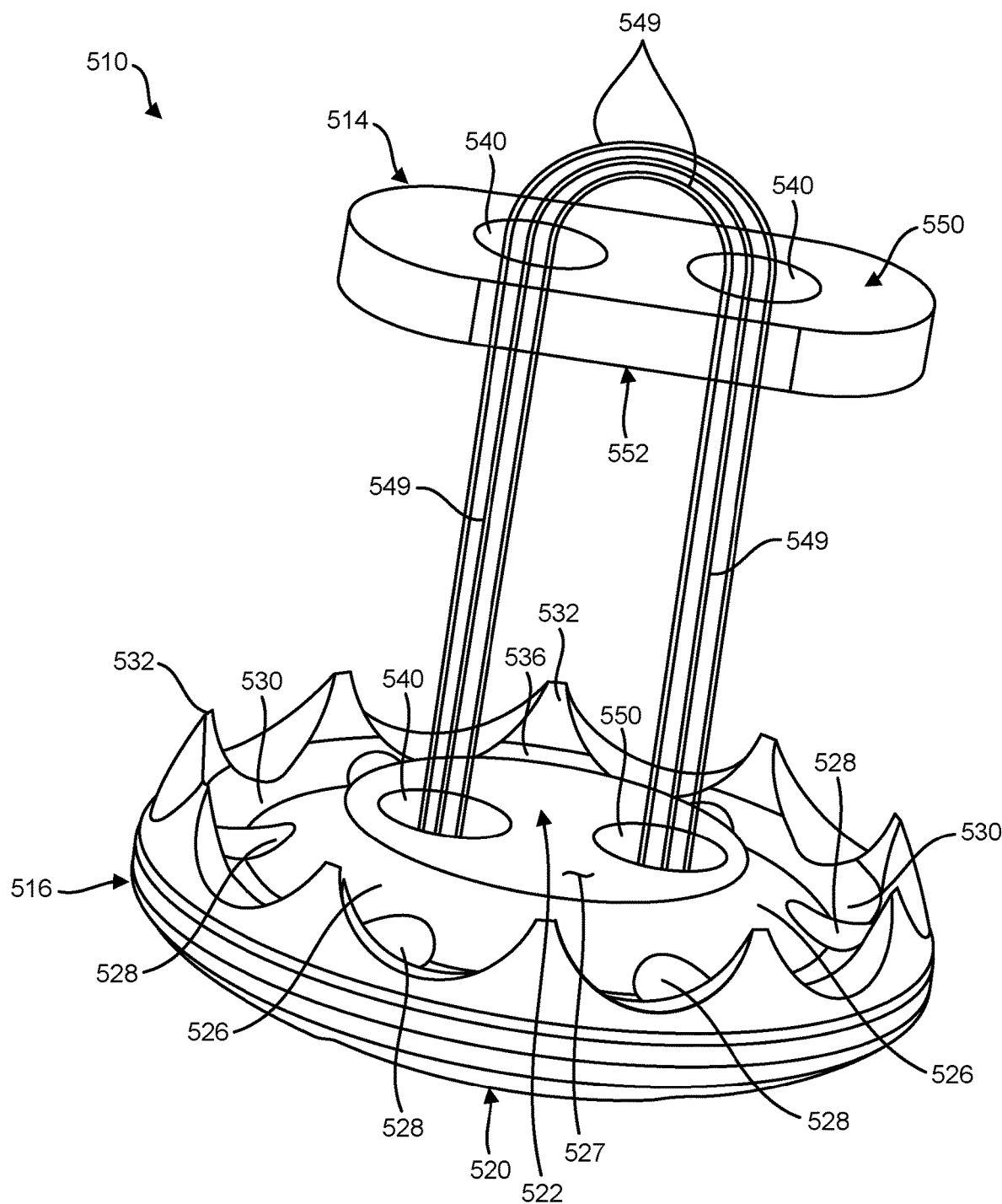
FIG. 64 illustrates an elevational perspective view of another exemplary soft tissue and bone retention device, in accordance with an aspect of the present disclosure.
Figure 66:
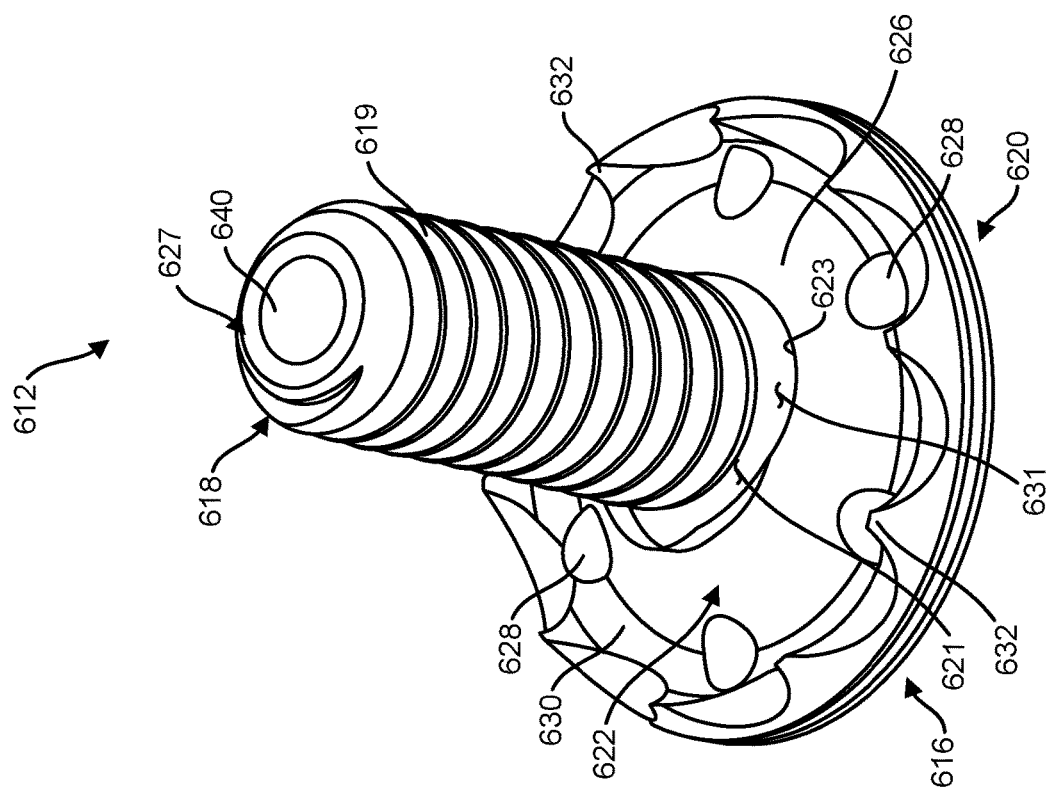
FIG. 66 illustrates another elevational perspective view of the soft tissue tack member of FIG. 65.
Figure 65:
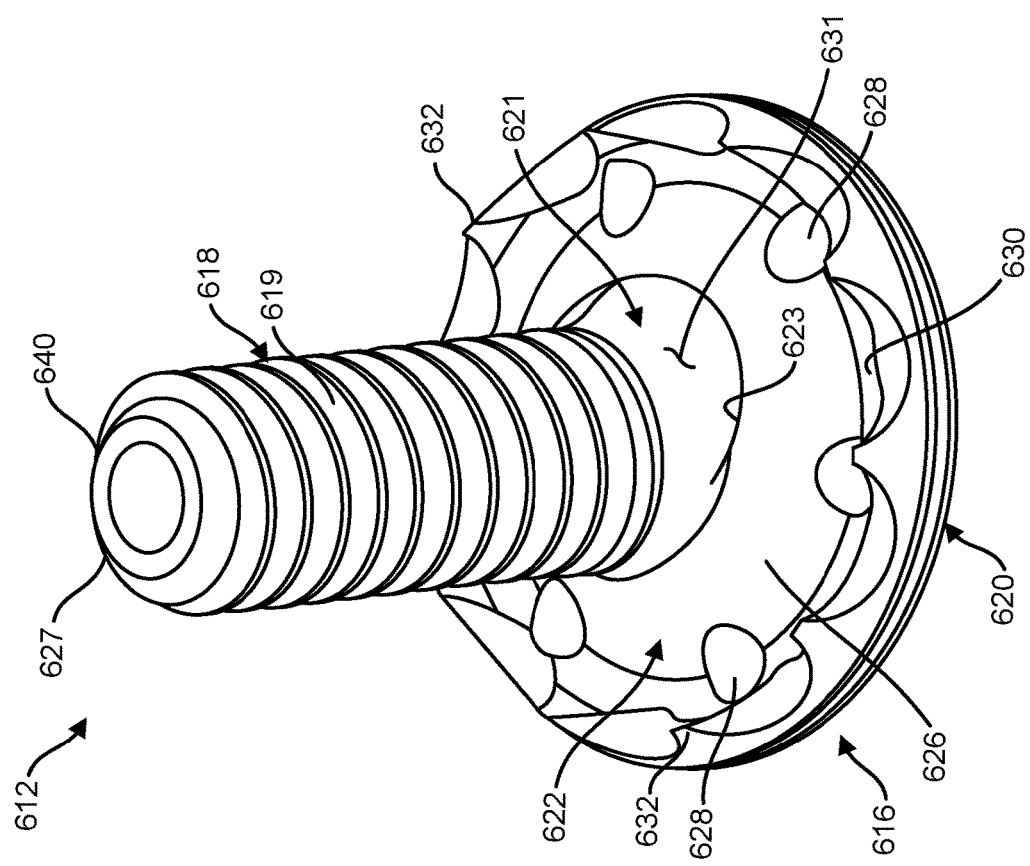
FIG. 65 illustrates an elevational perspective view of an exemplary two-piece soft tissue tack member of a soft tissue and bone retention device, in accordance with an aspect of the present disclosure.
Figure 68:
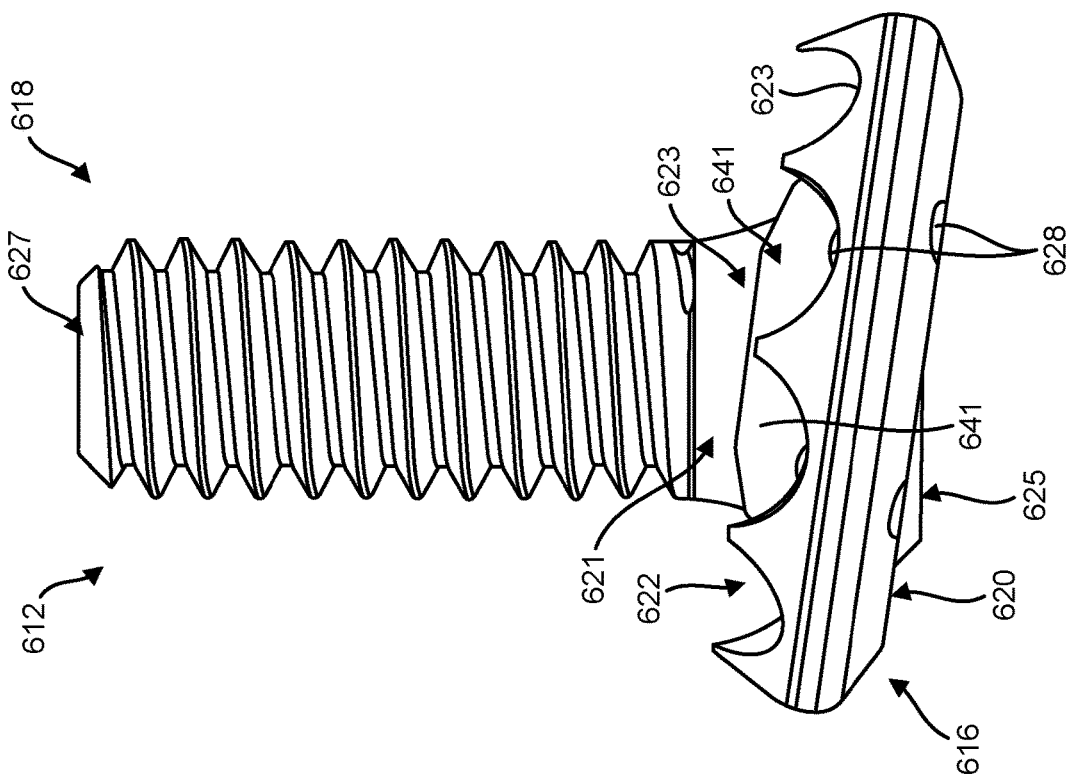
FIG. 68 illustrates a back view of the soft tissue tack member of FIG. 65.
Figure 67:
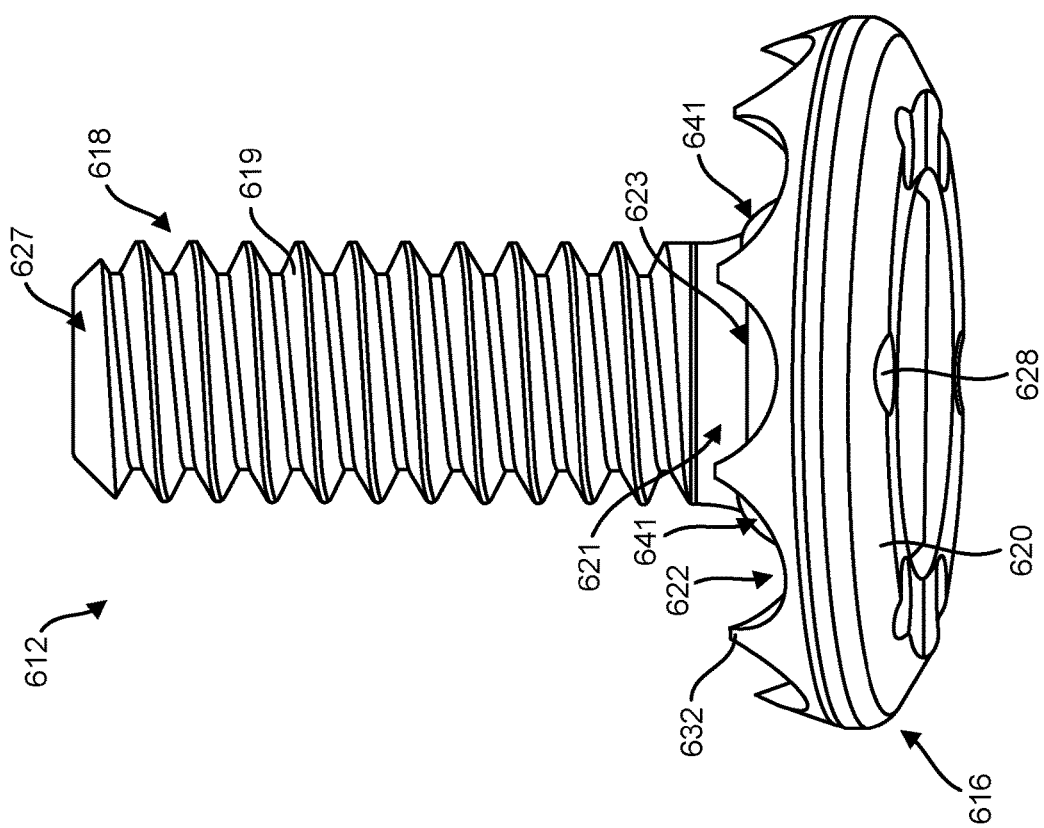
FIG. 67 illustrates a front view of the soft tissue tack member of FIG. 65.
Figure 70:
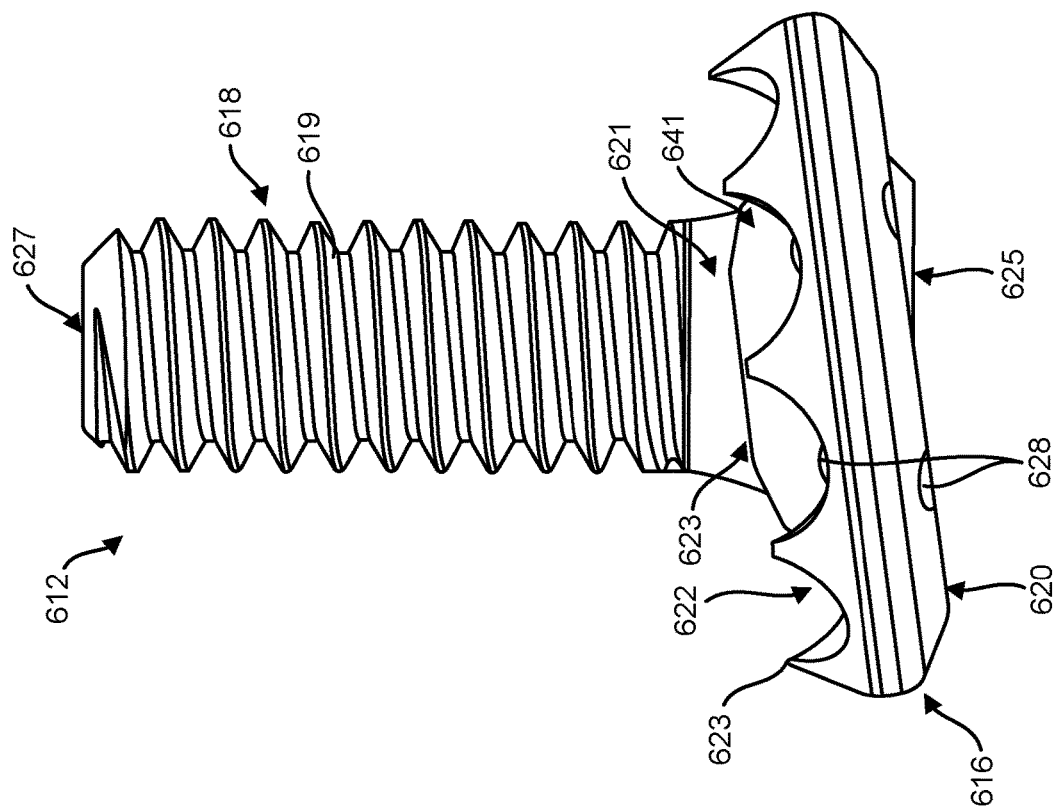
FIG. 70 illustrates a right side view of the soft tissue tack member of FIG. 65.
Figure 69:
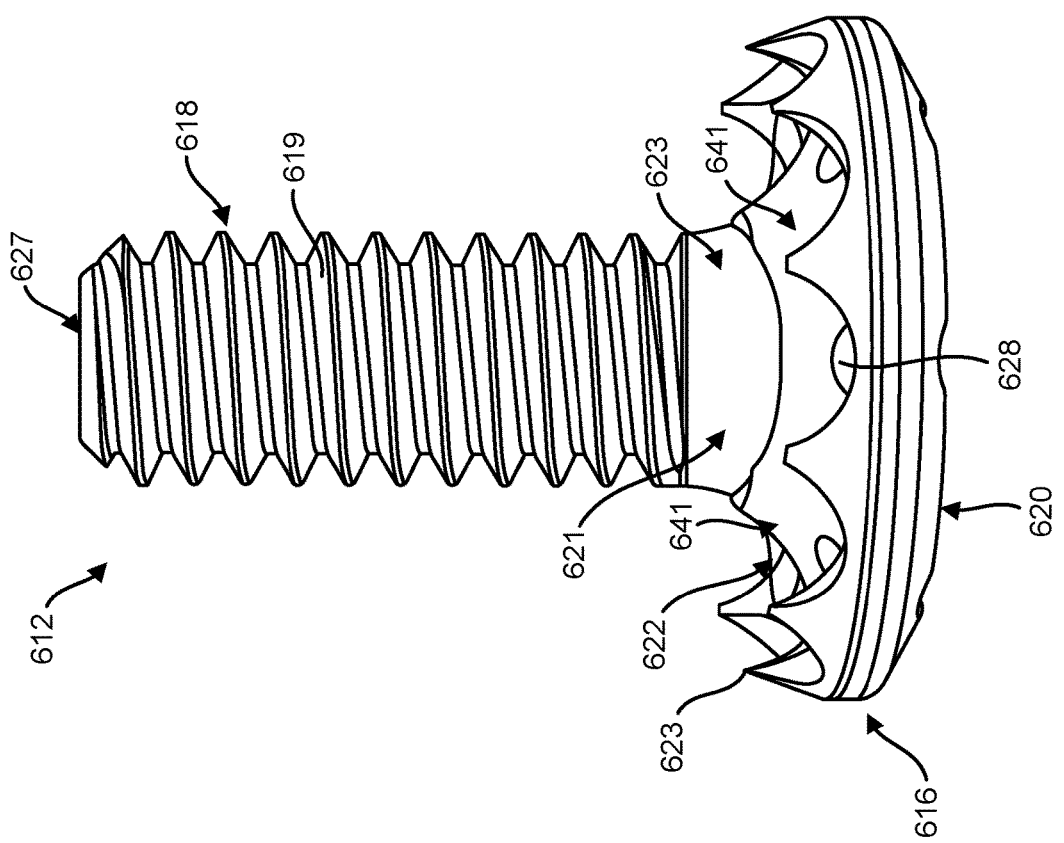
FIG. 69 illustrates a left side view of the soft tissue tack member of FIG. 65.

FIG. 64 illustrates another exemplary embodiment of a soft tissue retention device or system 510 configured to couple, retain, fix, and/or secure soft tissue to an associated or desired bone (such as, but not limited to, a relatively small bone (e.g., a bone of the foot or hand)). In some embodiments, the soft tissue retention device 510 may be particularly configured and/or advantageous for retention of a flexor digitorum longus tendon and an associated bone, such as, but not limited to, the plantar aspect of a proximal phalangeal base (bone) particularly, but not necessarily, for the correction of a toe contracture. However, the soft tissue retention device 510 may be configured and/or effectively utilized to retain, couple or fix any soft tissue (e.g., a tendon, ligament or the like) to any bone (e.g., any relatively small bone, such as a phalange, metatarsal or metacarpal bone) of a patient (e.g., a human patient).

Aspects of the soft tissue retention device 510 may be configured the same as or similar to aspects of the soft tissue retention device 100, the soft tissue retention device 210, the soft tissue tack member 312 and/or the soft tissue tack member 412 described above. For example, the soft tissue retention device 510 may include a soft tissue tack portion or member 512 and a bone anchor portion or member 514 configured to couple through a through aperture of the bone to retain or fix the associated soft tissue to the bone, as described above. The description of such common aspects, elements and/or functions of soft tissue retention device 510 that are the same or similar in structure and/or function, at least in part, to that of the soft tissue retention device 100, the soft tissue retention device 210, the soft tissue tack member 312 and/or the soft tissue tack member 412 are not repeated herein for brevity sake. However, it is specifically contemplated that the soft tissue retention device 310 may include components, aspects, configurations, functions or processes that are the same or similar to that of the soft tissue retention device 100, the soft tissue retention device 210, the soft tissue tack member 312 and/or the soft tissue tack member 412 (even if not shown/depicted in FIG. 64), and the description above directed thereto (and the alternative embodiments thereof) equally applies to the soft tissue retention device 510.

As shown in FIG. 64, the soft tissue tack member 512 of the soft tissue retention device 510 is void of a threaded shaft portion extending from the transition portion 526 of the head or washer portion 516. Rather, the transition portion 526 of the head portion 516 defines an exposed inner surface 527 that is configured to engage the soft tissue in use. The exposed inner surface 527 may be planar as shown in FIG. 64, or alternatively non-planar (e.g., concave and/or convex, and/or include surface texture, teeth, indentation(s), etc.). As also shown in FIG. 64, the soft tissue tack member 512 may also include at least two distinct through holes or cannulations 540 that extend from the exposed inner surface 527 to the outer end surface 520 of the head portion 516.

As also shown in FIG. 64, the bone anchor member 514 of the soft tissue retention device 510 may comprise a relatively thin disc, button, circular or oblong member that defines an outer end surface 550 and an inner surface 552 that is configured to engage the bone in use. The bone anchor member 514 may also include at least two distinct through holes or cannulations 540 that extend from the inner surface 552 to the outer end surface 550.

The bone anchor member 514 and the soft tissue tack member 512 may be configured to couple via at least one flexible member, thread, string, suture, wire or the like 549 that extends through the at least two cannulations 540 of the bone anchor member 514 and the soft tissue tack member 512, as shown in FIG. 64. For example, as shown in FIG. 64, the at least one flexible member 549 may extend over a portion of the outer end surface 550 of the bone anchor member 514 extending between the at least two cannulations 540 thereof and through the at least two cannulations 540 thereof, at least once (e.g., a plurality of times). Similarly, as also shown in FIG. 64, the at least one flexible member 549 may extend over a portion of the outer end surface 520 of the soft tissue tack member 512 extending between the at least two cannulations 540 thereof and through the at least two cannulations 540 thereof, at least once (e.g., a plurality of times). End portions of the at least one flexible member 549 may be tied, swaged/crimped together or otherwise fixed or coupled together.

In use, the at least one flexible member 549 may be passed through the cannulations 540 of the bone anchor member 514 and the soft tissue tack member 512 and the through hole of the bone and the soft tissue. In such an arrangement, the ends of the at least one flexible member 549 may be pulled apart or the at least one flexible member 549 otherwise forced through/along the cannulations 540 to draw the bone anchor member 514 and the soft tissue tack member 512 together such that the bone anchor member 514 engages the bone and the soft tissue tack member 512 retains (and compresses) the soft tissue onto/to the bone. As noted above, the inner surface 527 of the soft tissue tack member 512 (as well as the teeth 532, annular depression 530 and/or through holes 528 (if present), for example) may engage the soft tissue.

FIGS. 65-86 illustrate another exemplary embodiment of a soft tissue tack member 612 for a soft tissue retention device or system configured to couple, retain, fix, and/or secure soft tissue to an associated or desired bone (such as, but not limited to, a relatively small bone (e.g., a bone of the foot or hand)). In some embodiments, the soft tissue tack member 612 may be particularly configured and/or advantageous for retention of a flexor digitorum longus tendon and an associated bone, such as, but not limited to, the plantar aspect of a proximal phalangeal base (bone) particularly, but not necessarily, for the correction of a toe contracture. However, the soft tissue tack member 612 may be configured and/or effectively utilized to retain, couple or fix any soft tissue (e.g., a tendon, ligament or the like) to any bone (e.g., any relatively small bone, such as a phalange, metatarsal or metacarpal bone) of a patient (e.g., a human patient).

Aspects of the soft tissue tack member 612 may be configured the same as or similar to aspects of the soft tissue tack member 10, the soft tissue tack member 212, the soft tissue tack member 312, soft tissue tack member 412 and/or the soft tissue tack member 512 described above. For example, the soft tissue tack member 612 may be configured to threadably couple with a bone anchor member within a through aperture of the bone to retain or fix the associated soft tissue to the bone, as described above. The description of such common aspects, elements and/or functions of the soft tissue tack member 612 that are the same or similar in structure and/or function, at least in part, to that of the soft tissue tack member 10, the soft tissue tack member 212, the soft tissue tack member 312, soft tissue tack member 412 and/or the soft tissue tack member 512 is not repeated herein for brevity sake. However, it is specifically contemplated that the soft tissue tack member 612 may include components, aspects, configurations, functions or processes that are the same or similar to that of the soft tissue tack member 10, the soft tissue tack member 212, the soft tissue tack member 312, soft tissue tack member 412 and/or the soft tissue tack member 512 (even if not shown/depicted in FIGS. 65-86), and the description above directed thereto (and the alternative embodiments thereof) equally applies to the soft tissue tack member 612.

As shown in FIGS. 65-86, the soft tissue tack member 612 differs from the soft tissue tack member 10, the soft tissue tack member 212, the soft tissue tack member 312, soft tissue tack member 412 and the soft tissue tack member 512 in that the shaft portion 618 and the head or washer portion 616 are separate and distinct components that are movably coupled together. Specifically, as shown in FIGS. 65-86, an adjustment head portion 621 of the shaft portion 618 is received within an adjustment slot 623 of the head or washer portion 616.

As shown in FIGS. 71, 72 and 75-79, the adjustment head portion 621 of the shaft portion 618 is positioned at one axial end 625 and includes a drive aperture 654 for applying torque to the shaft portion 618 via a tool (as described above), and a cannulated opening 640 in communication with the drive aperture 654 (which may aid in implanting the soft tissue tack member 612, as described above. A threaded coupling post portion 619 of the shaft portion 618 extends axially from the adjustment head portion 621 and defines the other axial end 627 of the shaft portion 618, as shown in FIGS. 71, 72 and 75-79. The threaded post 619 (externally threaded, as shown, and/or internally threaded) is configured to threadably coupled with a bone anchor member within a through hole in a bone, as discussed above. The threaded post 619 also includes the cannulated opening 640 in communication with the cannulated opening 640 of the head portion 616 such that the shaft portion 618, as a whole, is fully cannulated. In some other embodiments (not shown), the shaft portion 618 may only be partially cannulated (as described above) or non-cannulated.

As also shown in FIGS. 65-73 and 75-79, the adjustment head portion 621 includes an outer annular articulation surface 631 that engages and articulates with the head portion 616 when the shaft portion 618 is seated within the adjustment slot 623 of the head portion 616. A portion of the articulation surface 631 positioned proximate to the axial end 625 of the adjustment head portion 621 defines a larger cross-sectional dimension/size (e.g., diameter) than the minimum cross-sectional dimension/size (e.g., diameter) of the adjustment slot 623 of the head portion 616 such that the adjustment head portion 621 is prevented from passing or translating through the adjustment slot 623 and the articulation surface 631 abuts/engages (and articulates) with the head portion 616, as shown in FIGS. 71 and 72.

Figure 71:
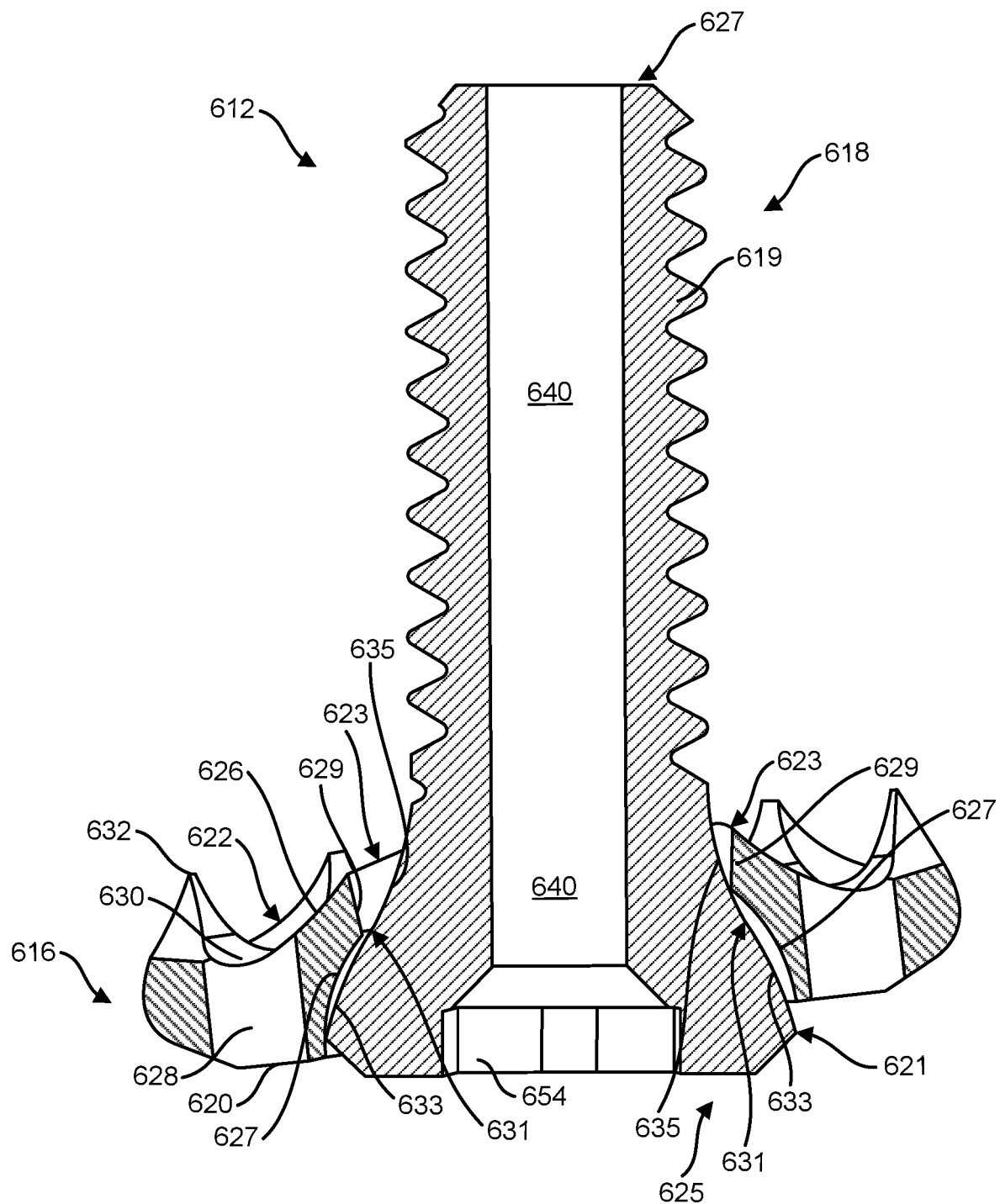
FIG. 71 illustrates a right side cross-sectional view of the soft tissue tack member of FIG. 65.
Figure 72:
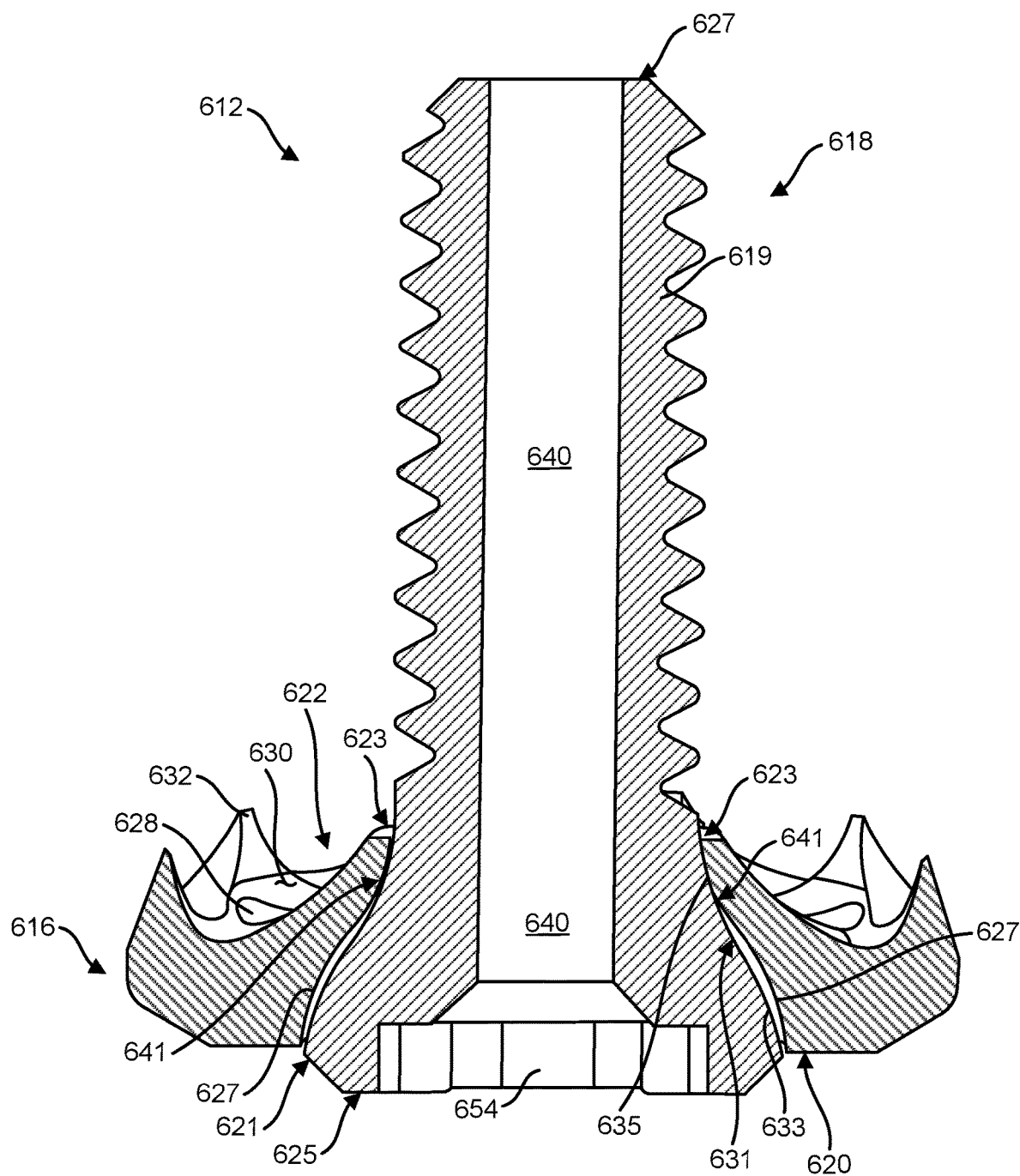
FIG. 72 illustrates a back cross-sectional view of the soft tissue tack member of FIG. 65.
Figure 74:
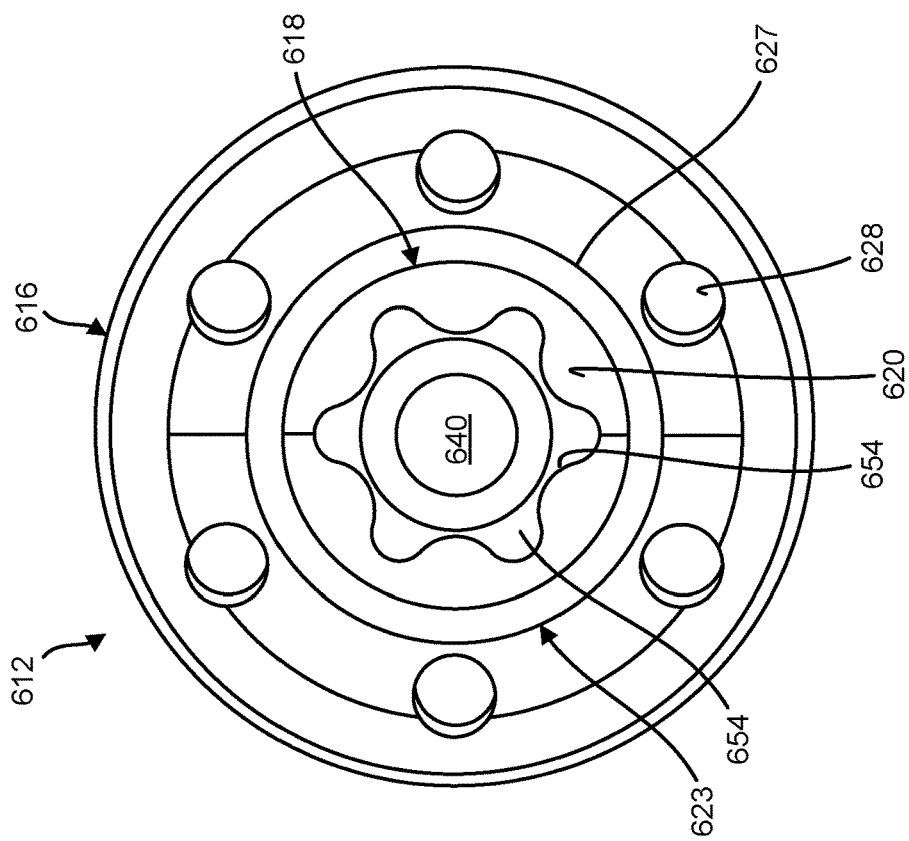
FIG. 74 illustrates a bottom cross-sectional view of the soft tissue tack member of FIG. 65.
Figure 73:
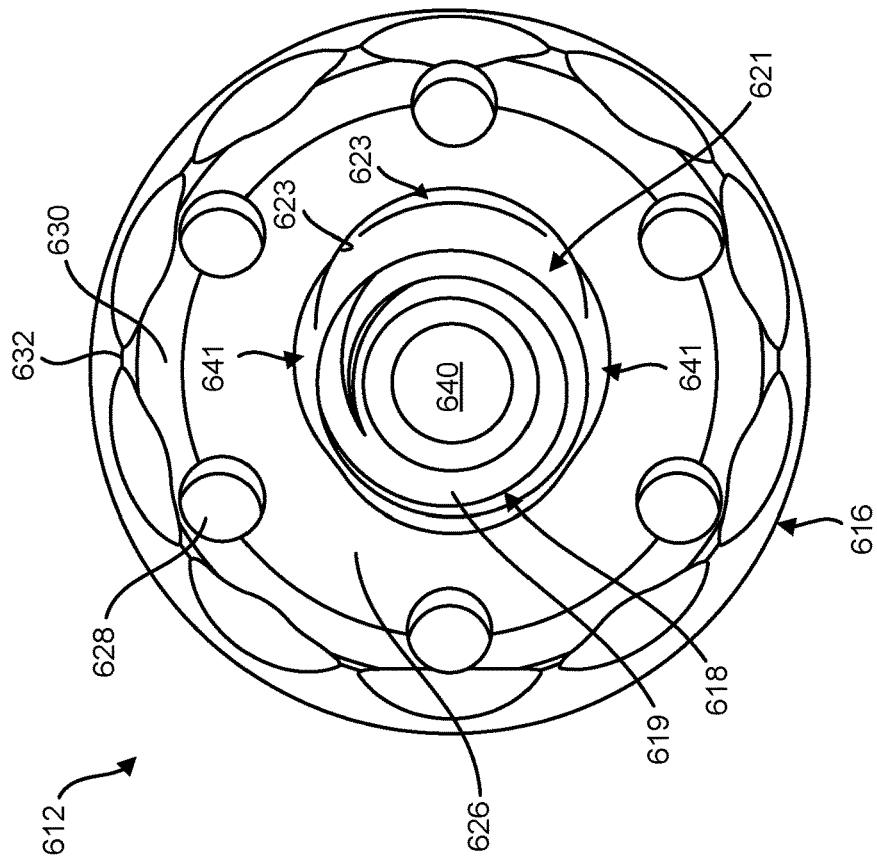
FIG. 73 illustrates a top view of the soft tissue tack member of FIG. 65.
Figure 76:
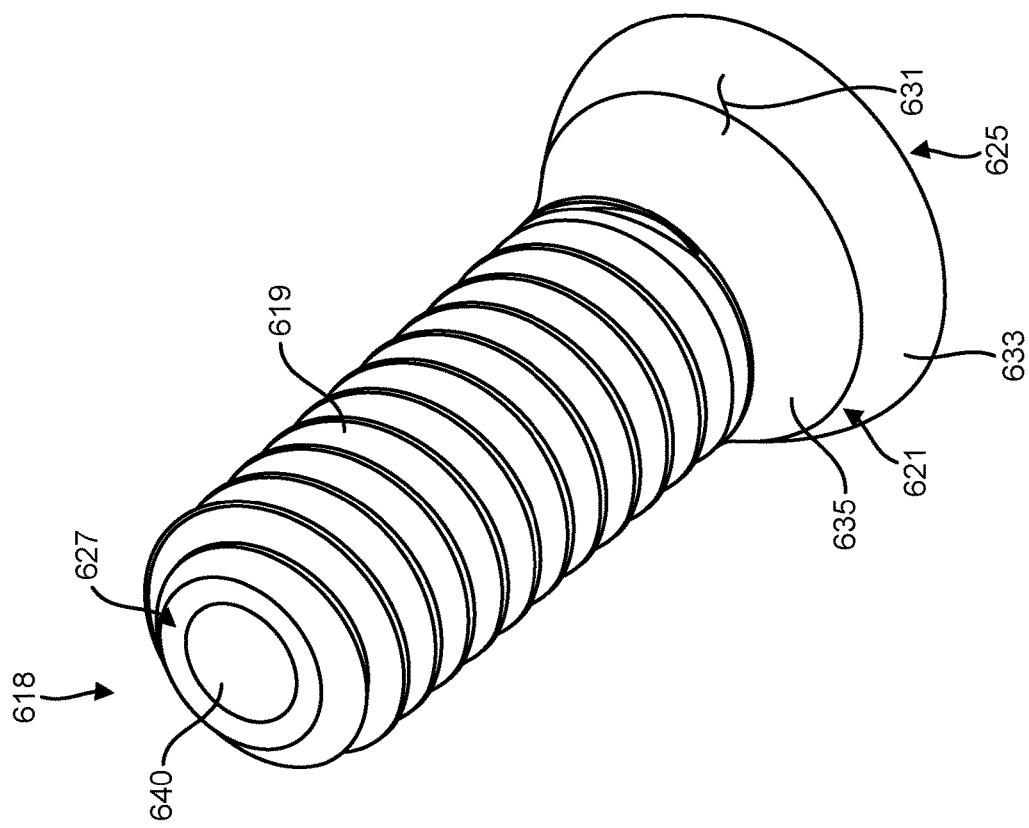
FIG. 76 illustrates an elevational perspective view of the shaft portion of FIG. 75.
Figure 75:
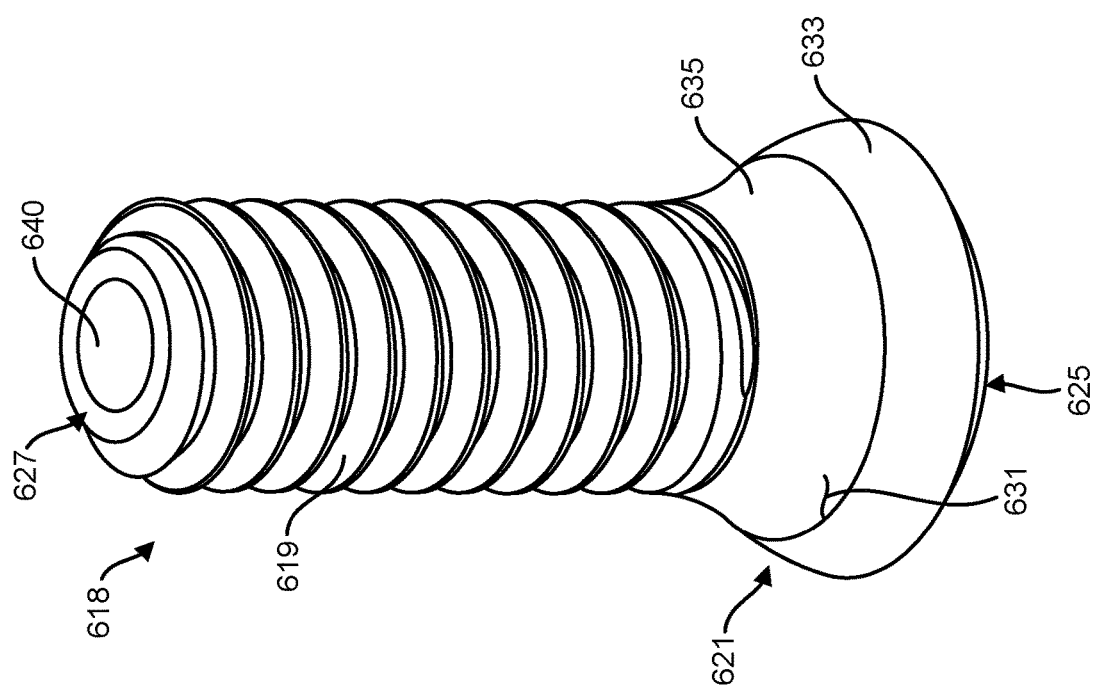
FIG. 75 illustrates an isometric view of a shaft portion of the soft tissue tack member of FIG. 65.
Figure 82:
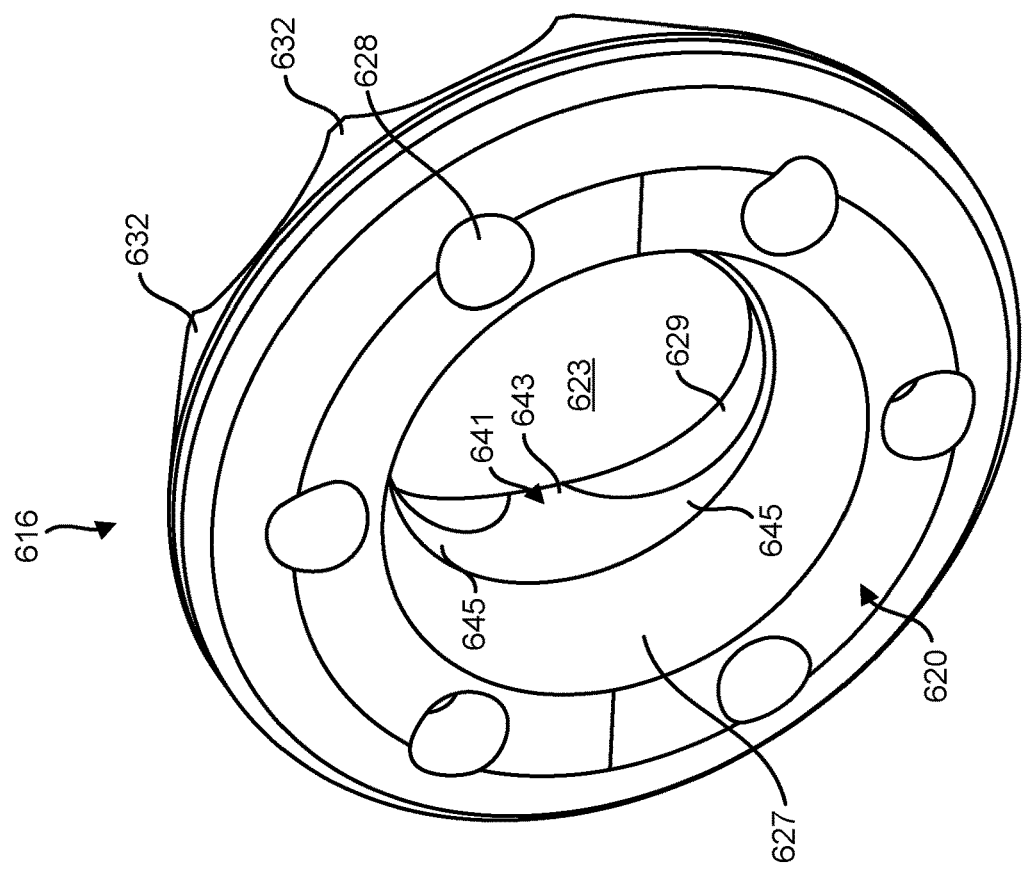
FIG. 82 illustrates a bottom elevational perspective view of the head portion of FIG. 80.
Figure 81:
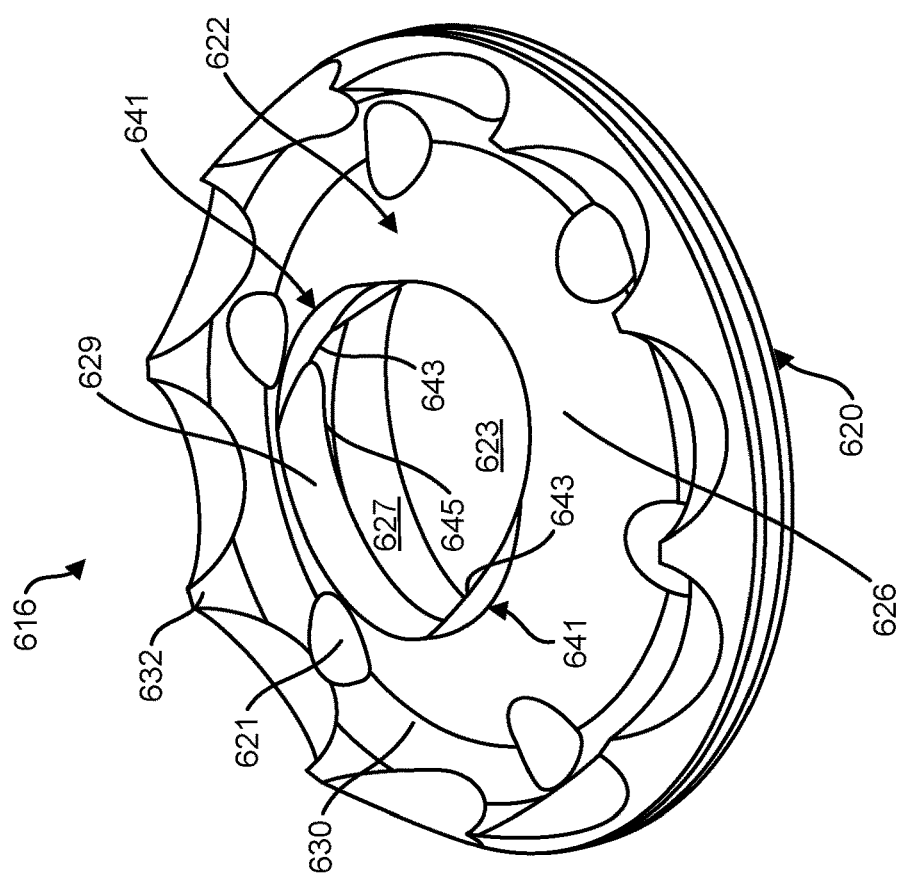
FIG. 81 illustrates an elevational perspective view of the head portion of FIG. 80.
Figure 84:
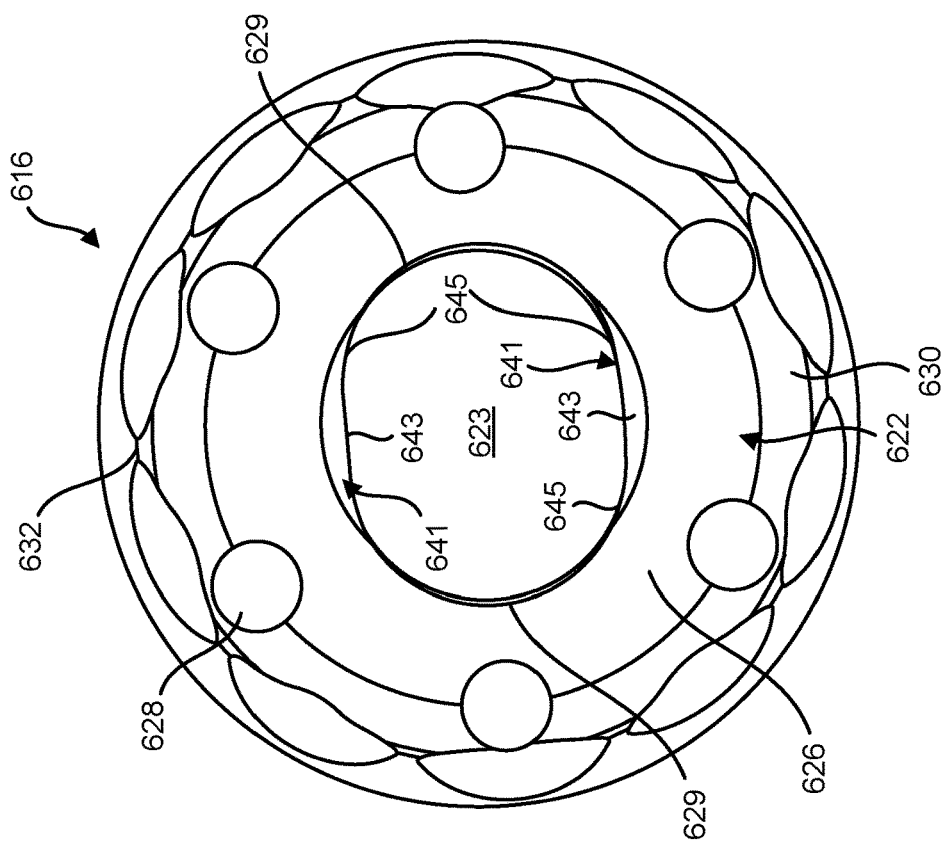
FIG. 84 illustrates a top view of the head portion of FIG. 80.
Figure 83:
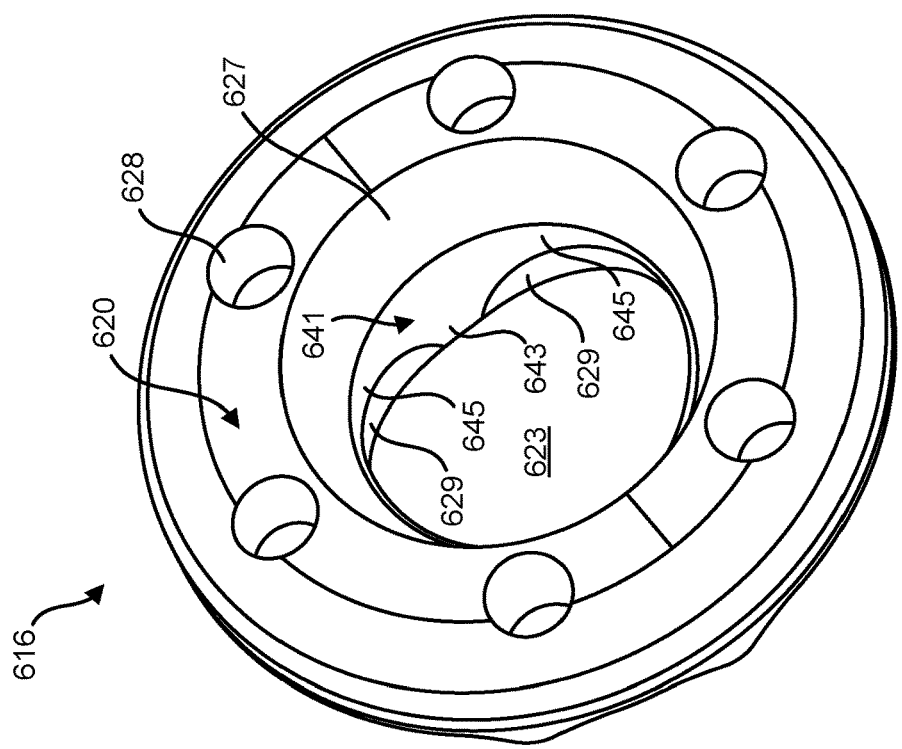
FIG. 83 illustrates another bottom elevational perspective view of the head portion of FIG. 80.
Figure 85:
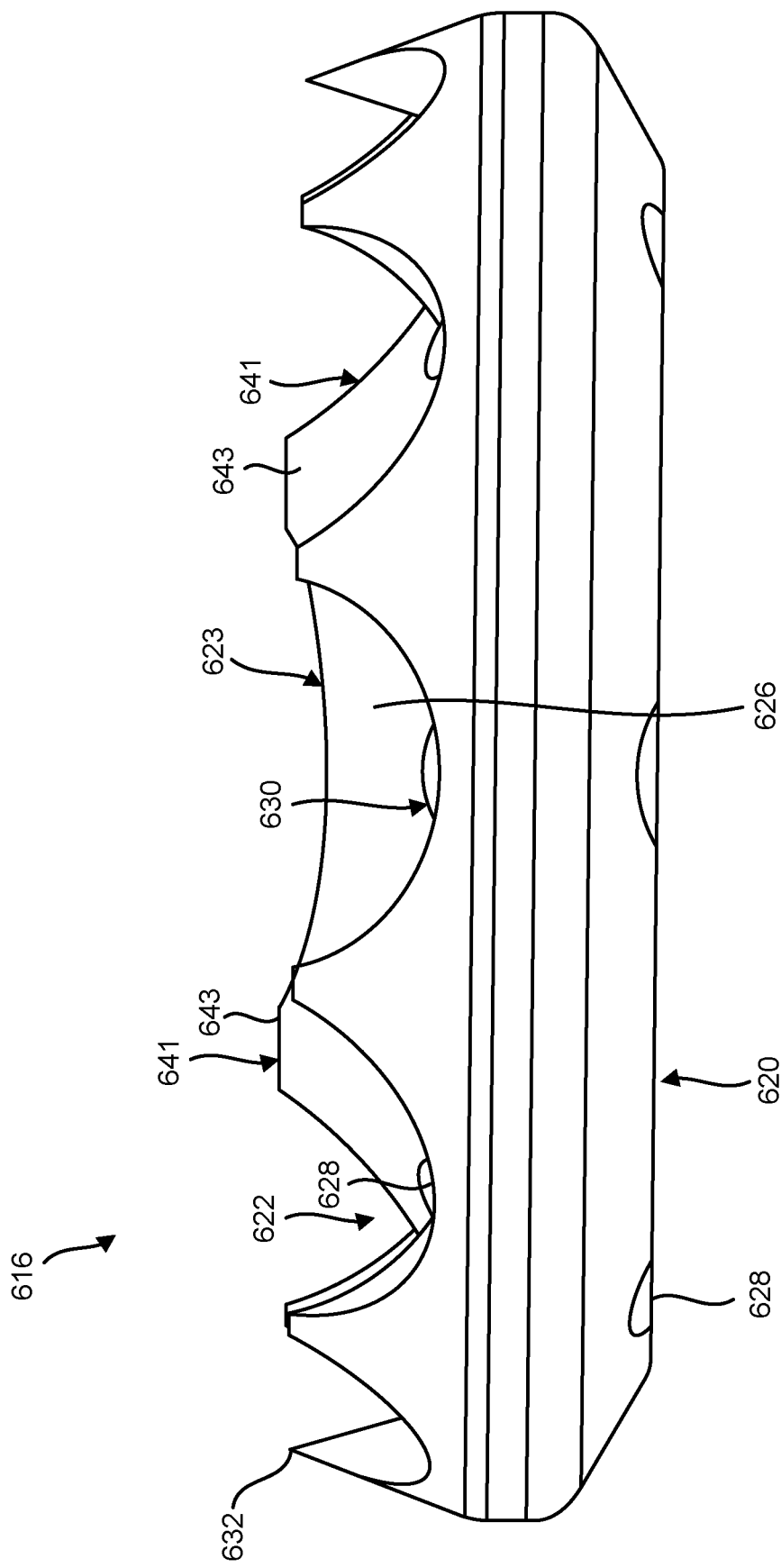
FIG. 85 illustrates a side view of the head portion of FIG. 80.

As shown in FIGS. 71, 72 and 75-79, the articulation surface 631 of the adjustment head portion 621 of the shaft portion 618 may include a convex portion 635 that is positioned proximate to the axial end 625 of the adjustment head portion 621 that is convex (e.g., arcuately convex) in the axial direction (as well as being angularly or annularly convex along a plane that is normal to the axis of the shaft portion 618). The convex portion 635 of the articulation surface 631 of the adjustment head portion 621 may define a larger cross-sectional dimension/size (e.g., diameter) than the minimum cross-sectional dimension/size (e.g., diameter) of the adjustment slot 623 of the head portion 616. As shown in FIGS. 71 and 72, the convex portion 635 may engage and articulate with at least a portion of the adjustment slot 623 of the head portion 616 as the head portion 616 of the tack member 612 fully articulates over the adjustment head portion 621.

As also shown in FIGS. 71, 72 and 75-79, the articulation surface 631 of the adjustment head portion 621 of the shaft portion 618 may include a concave portion 635 that is positioned proximate to the threaded post 619 that is concave (e.g., arcuately concave) in the axial direction (as well as being angularly or annularly convex along a plane that is normal to the axis of the shaft portion 618). The concave portion 635 of the articulation surface 631 may extend directly from the convex portion 635 of the articulation surface (i.e., the convex portion 635 and the concave portion 635 of the articulation surface 631 may be contiguous surface portions), as also shown in FIGS. 71, 72 and 75-79. The concave portion 635 of the articulation surface 631 of the adjustment head portion 621 may define a larger cross-sectional dimension/size (e.g., diameter) than the minimum cross-sectional dimension/size (e.g., diameter) of the adjustment slot 623 of the head portion 616. As shown in FIGS. 71 and 72, the concave portion 635 may engage and articulate with at least a portion of the adjustment slot 623 of the head portion 616 as the head portion 616 of the tack member 612 fully articulates over the adjustment head portion 621.

Figure 86:
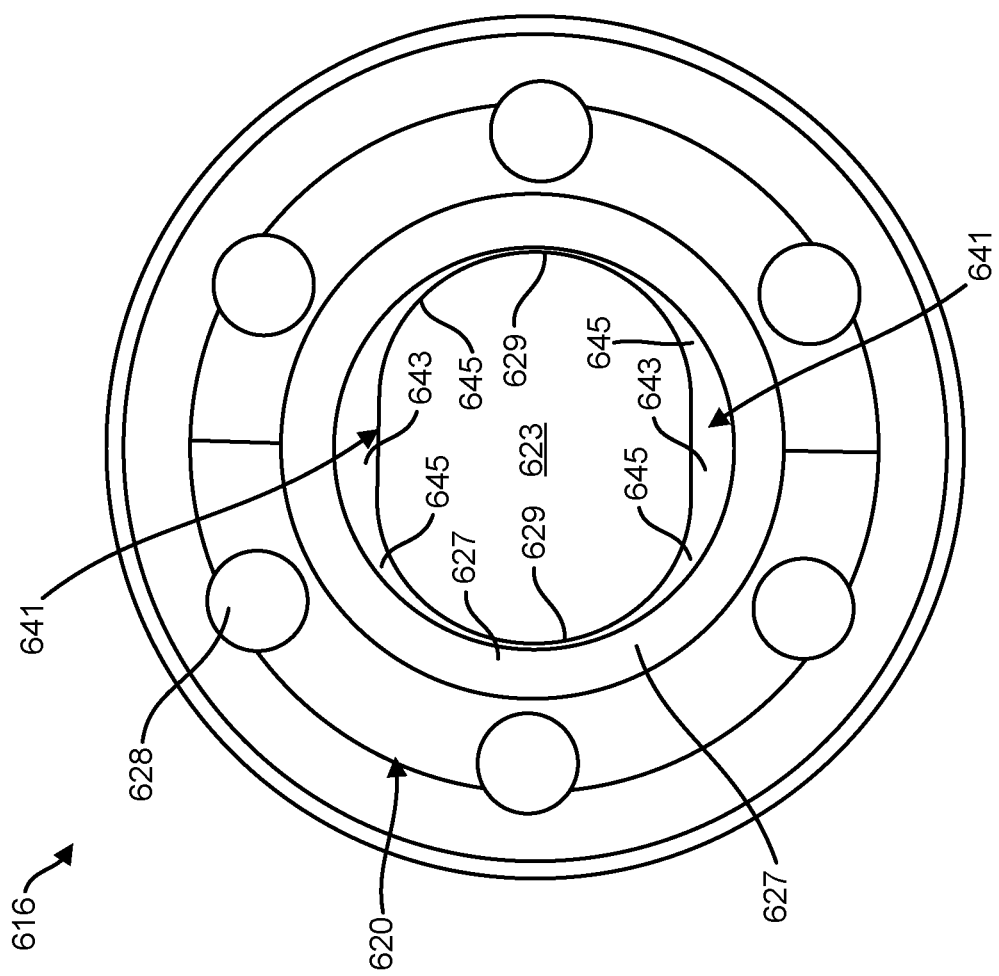
FIG. 86 illustrates a bottom view of the head portion of FIG. 80.
Figure 88:
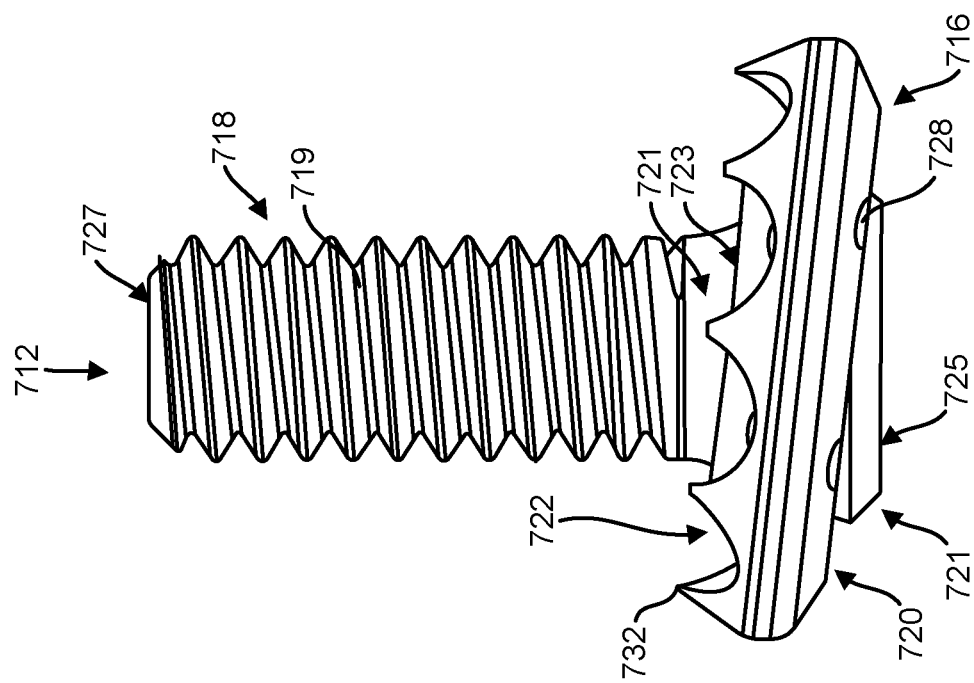
FIG. 88 illustrates a side view of the soft tissue tack member of FIG. 87.
Figure 87:
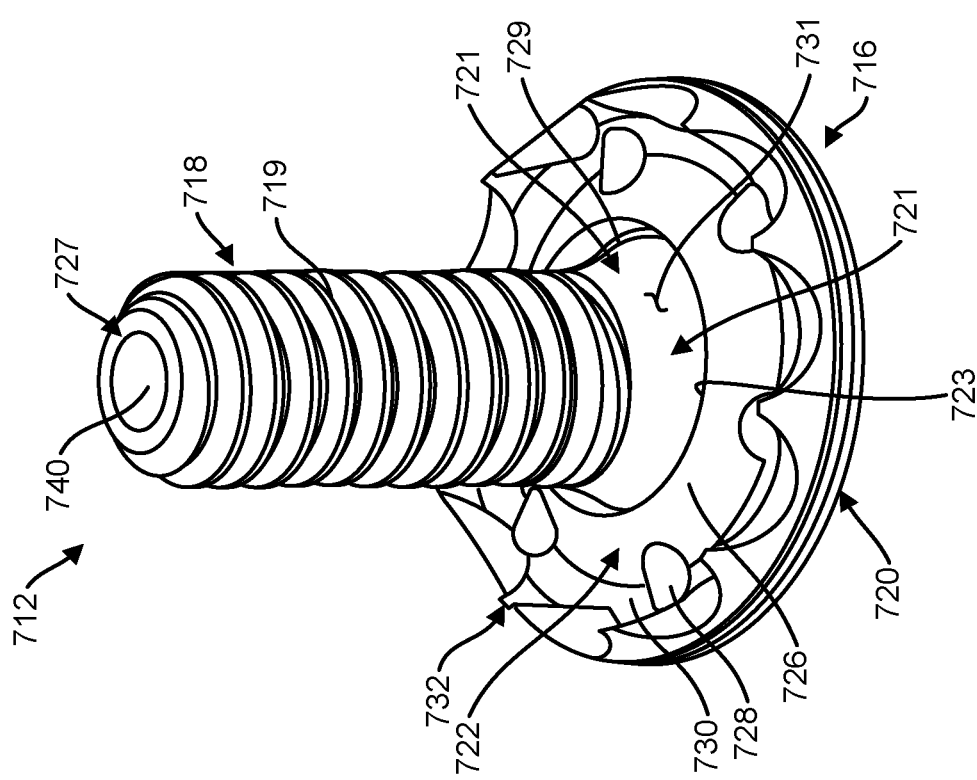
FIG. 87 illustrates a side view of the soft tissue tack member of a soft tissue and bone retention device, in accordance with an aspect of the present disclosure.
Figure 90:
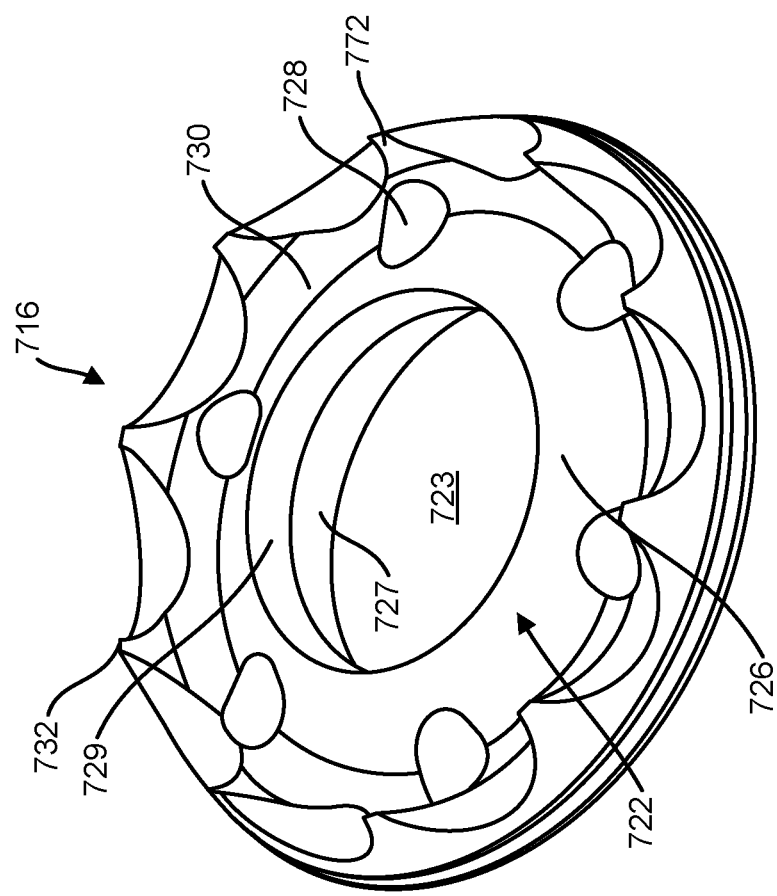
FIG. 90 illustrates an elevational perspective view of a head portion of the soft tissue tack member of FIG. 87.
Figure 89:
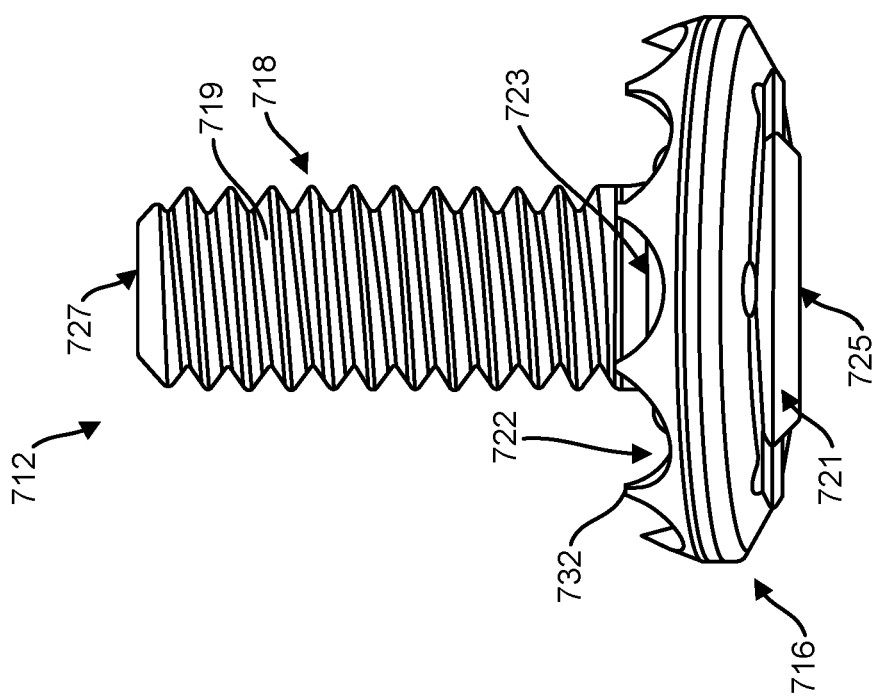
FIG. 89 illustrates a front view of the soft tissue tack member of FIG. 87.
Figure 92:
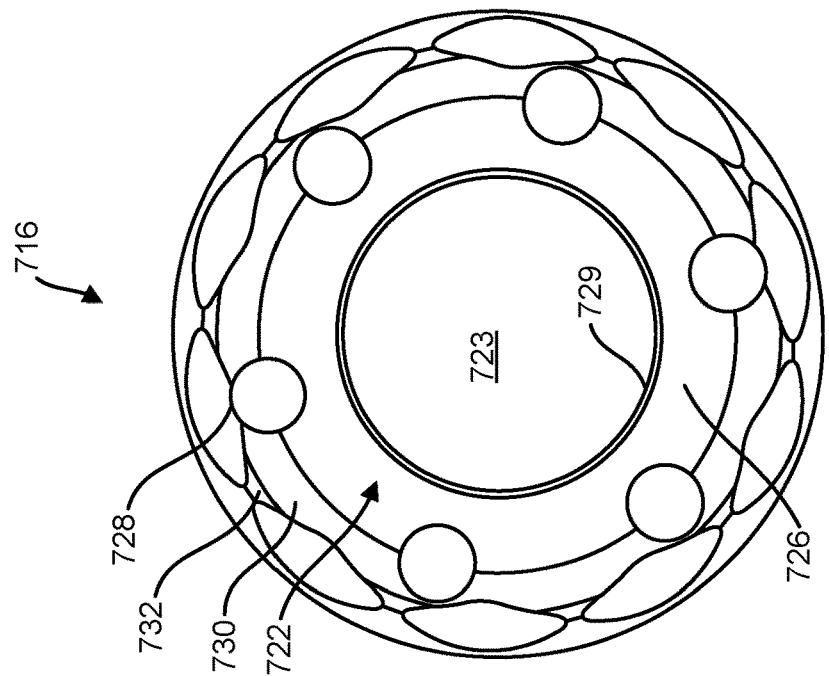
FIG. 92 illustrates a top view of the head portion of FIG. 90.
Figure 91:
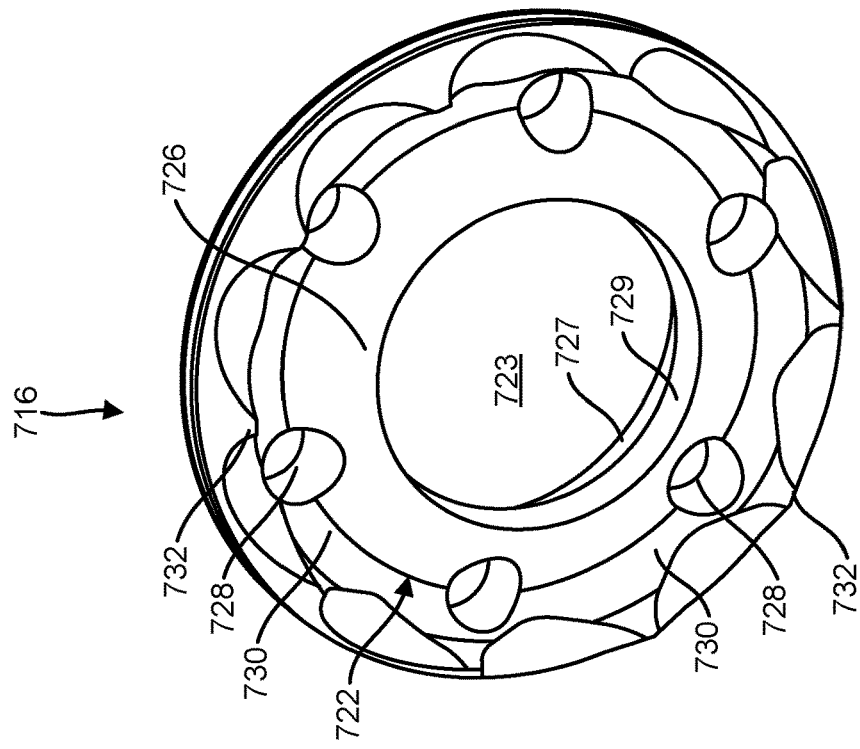
FIG. 91 illustrates a perspective view of the head portion of FIG. 90.
Figure 93:
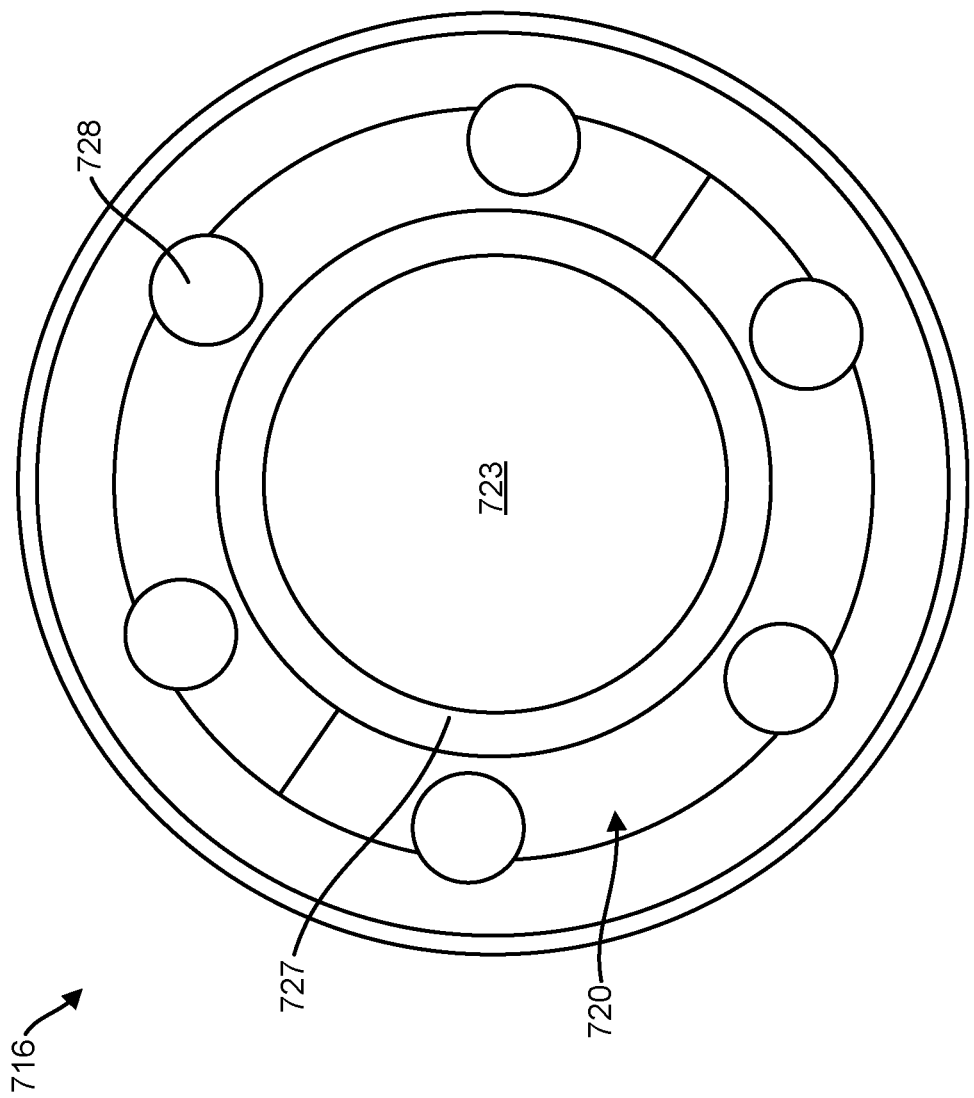
FIG. 93 illustrates a bottom view of the head portion of FIG. 90.
Figure 94:
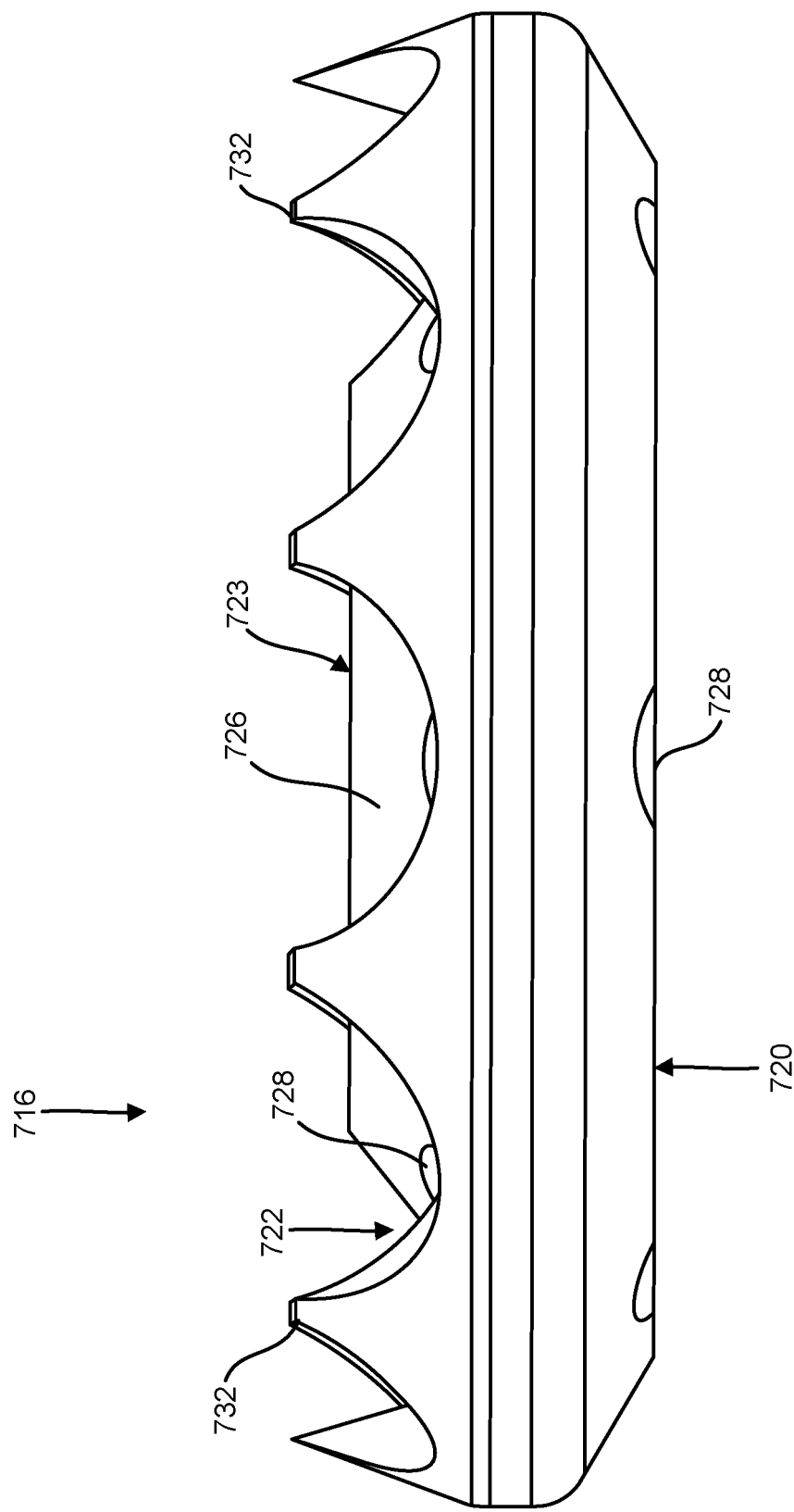
FIG. 94 illustrates a side view of the head portion of FIG. 90.

As shown in FIGS. 65-73 and 80-86, the adjustment slot 623 of the head portion 616 may be formed through the transition or raised portion 626 of the inner or under side 622 of the head portion 616 to the outer end surface 620. As shown in FIGS. 71, 72 and 80-83, the outer side or portion of the adjustment slot 623 that is proximate to the outer side 622 may include an annular beveled or countersunk concave surface portion 627 that extends radially-inward as it extends axially from the outer end surface 620 toward the inner side 620. The beveled concave surface portion 627 is concave (e.g., arcuately concave) in the axial direction (as well as being angularly or annularly convex along a plane that is normal to an axis of the adjustment slot 623), as shown in FIGS. 71 and 72. As shown in FIG. 86, the outer beveled concave surface portion 627 may be annularly circular as it extends about the axis of the adjustment slot 623.

The outer beveled concave surface portion 627 of the adjustment slot 623 is configured to allow the adjustment head portion 621 to articulate within the adjustment slot 623, as shown in FIGS. 65-72. The outer beveled concave surface portion 627 of the adjustment slot 623 may be sized and shaped to accept or mate with the convex portion 635 of the articulation surface 631 of the adjustment head portion 621, as shown in FIGS. 71 and 72. For example, they may be defined by the same or similar radius (e.g., within about 25%, or about 15%, of each other). The outer beveled concave surface portion 627 of the adjustment slot 623 may also be sized and shaped to accept or mate with at least a portion of the concave portion 635 of the articulation surface 631 of the adjustment head portion 621, as shown in FIG. 71.

As shown in FIGS. 71, 72, 80-84 and 86, the adjustment slot 623 of the head portion 616 may be formed through the transition or raised portion 626 of the head portion 616 to the inner side 622. As shown in FIGS. 71, 72, 80-84 and 86, the inner side or portion of the adjustment slot 623 that is proximate to the inner side 622 may include a relief surface portion 629 extending from the inner side 622. The relief surface portion 629 may extend axially (i.e., parallel in all directions to the axis of the adjustment slot 623) or may be extend radially-inward toward the axis of the adjustment slot 623 as it extends axially from the inner side 622 toward the outer side 620 of the head portion 616. The relief surface portion 629 may be flat/linear (as shown in FIG. 71), rectilinear or arcuate along the axial direction (as well as being angularly or annularly convex along a plane that is normal to an axis of the adjustment slot 623).

The outer beveled concave surface portion 627 and the relief surface portion 629 of the adjustment slot 623 of the head portion 616 are configured to allow the head portion 616 to articulate over the articulation surface 631 of the adjustment head portion 621 of the shaft portion 618 along or within a defined range of relative angulation about in all directions about the axis of the shaft portion 618. For example, the outer beveled concave surface portion 627 and the relief surface portion 629 of the adjustment slot 623 of the head portion 616 are configured to allow the head portion 616 to articulate over the articulation surface 631 of the adjustment head portion 621 of the shaft portion 618 such that a plane defined by the head portion 616 is angled up to 45 degrees from normal to the axis of the shaft portion 618 (e.g., a first lateral side of the head portion 616 may be angled within the range of about 45 degrees to about 90 degrees from the axis of the shaft portion 618, and a second lateral side of the head portion 616 may be angled within the range of about 90 degrees and about 135 degrees from the axis of the shaft portion 618). In some other such embodiments, the outer beveled concave surface portion 627 and the relief surface portion 629 of the adjustment slot 623 of the head portion 616 are configured to allow the head portion 616 to articulate over the articulation surface 631 of the adjustment head portion 621 of the shaft portion 618 such that a plane defined by the head portion 616 is angled up to 30 degrees from normal to the axis of the shaft portion 618 (e.g., a first lateral side of the head portion 616 may be angled within the range of about 60 degrees to about 90 degrees from the axis of the shaft portion 618, and a second lateral side of the head portion 616 may be angled within the range of about 90 degrees and about 120 degrees from the axis of the shaft portion 618). In some other such embodiments, the outer beveled concave surface portion 627 and the relief surface portion 629 of the adjustment slot 623 of the head portion 616 are configured to allow the head portion 616 to articulate over the articulation surface 631 of the adjustment head portion 621 of the shaft portion 618 such that a plane defined by the head portion 616 is angled up to 15 degrees from normal to the axis of the shaft portion 618 (e.g., a first lateral side of the head portion 616 may be angled within the range of about 75 degrees to about 90 degrees from the axis of the shaft portion 618, and a second lateral side of the head portion 616 may be angled within the range of about 90 degrees and about 105 degrees from the axis of the shaft portion 618).

Although the outer beveled concave surface portion 627 and the relief surface portion 629 of the adjustment slot 623 of the head portion 616 may be configured to allow the head portion 616 to articulate over the articulation surface 631 of the adjustment head portion 621 of the shaft portion 618 along/within a defined range of relative angulation or motion about in all directions about the axis of the shaft portion 618, the adjustment slot 623 of the head portion 616 may include lip portions 641 that restrict such angulation or articulation along a single direction or axis, as shown in FIGS. 65-70, 72, 73 and 80-86. For example, as shown in FIGS. 65-70, 72, 73 and 80-86, the lip portions 641 of the adjustment slot 623 may extend radially-inward toward the axis of the adjustment slot 623 as they extend from the outer beveled concave surface portion 627 toward the inner side 622. In some embodiments, the inner surfaces of the lip portions 641 are convex (e.g., arcuately convex) in the axial direction (as well as being angularly or annularly convex along a plane that is normal to an axis of the adjustment slot 623), as shown in FIG. 72. The inner surfaces of the lip portions 641 of the adjustment slot 623 may be sized and shaped to accept or mate with the concave portion 635 of the articulation surface 631 of the adjustment head portion 621, as shown in FIG. 72. For example, they may be defined by the same or similar radius (e.g., within about 25%, or about 15%, of each other).

As shown in FIGS. 65-70, 72, 73 and 80-86, the lip portions 641 of the adjustment slot 623 may include a pair of lip portions 641 positioned on opposing lateral sides of the axis of the adjustment slot 623. Each lip portion 641 may include a tip portion 643 that extends furthest radially-inward toward the axis of the adjustment slot 623 (i.e., into the adjustment slot 623), and extends axially between the beveled concave surface portion 627 and the inner side 622. Each lip portion 641 may also include side portions 645 that flank the tip portion 643 that extend axially between the beveled concave surface portion 627 and the relief surface portion 629 and progressively radially-inward toward the axis of the adjustment slot 623 (i.e., into the adjustment slot 623) as they extend annularly or radially toward the tip portion 643 The lip portions 641 thereby interrupt the annular circular shape adjustment slot 623 of the head portion 616, and form an oblong, elliptical or elongated slot shape, as shown in FIG. 86.

As shown in FIG. 72, the lip portions 641 of the adjustment slot 623 may engage, abut or mate with the concave surface portion 635 of the articulation surface 631 of the adjustment head portion 621, and the outer beveled concave surface portion 627 of the adjustment slot 623 may engage, abut or mate with the convex surface portion 633 of the articulation surface 631 of the adjustment head portion 621, such that the head portion 616 is only able to angle or articular over the articulation surface 631 of the adjustment head portion 621 with respect to the axis of the shaft portion 618 along one direction or within a limited number or range of directions about the axis of the shaft portion 618. As discussed above, it may be desirable to retain, attach or fix a soft tissue to a sloped or angled outer surface of a bone. For example, it may be desirable to implant the soft tissue retention device in a portion of a bone that lies on a metaphyseal slope. In such embodiments, the adjustability of the angulation or sloped of the head portion 616 of the soft tissue tack member 612 with respect to the threaded shaft portion 618 allows the head portion 616 to extend substantially parallel to or approximate the sloped or angled outer surface of the bone when the shaft portion 618 is positioned within the through hole of the bone and threadably coupled with a bone anchor member (not shown). In this way, at least a substantial majority or entirety of the inner or under side 622 of the head portion 616 may engage and grip the soft tissue and fix and compress the soft tissue to the angled outer surface of the bone.

FIGS. 87-94 illustrate another exemplary embodiment of a soft tissue tack member 712 for a soft tissue retention device or system configured to couple, retain, fix, and/or secure soft tissue to an associated or desired bone (such as, but not limited to, a relatively small bone (e.g., a bone of the foot or hand)). In some embodiments, the soft tissue tack member 712 may be particularly configured and/or advantageous for retention of a flexor digitorum longus tendon and an associated bone, such as, but not limited to, the plantar aspect of a proximal phalangeal base (bone) particularly, but not necessarily, for the correction of a toe contracture. However, the soft tissue tack member 712 may be configured and/or effectively utilized to retain, couple or fix any soft tissue (e.g., a tendon, ligament or the like) to any bone (e.g., any relatively small bone, such as a phalange, metatarsal or metacarpal bone) of a patient (e.g., a human patient).

Aspects of the soft tissue tack member 712 may be configured the same as or similar to aspects of the soft tissue tack member 10, the soft tissue tack member 212, the soft tissue tack member 312, soft tissue tack member 412, the soft tissue tack member 512 and/or the soft tissue tack member 612 described above. For example, the soft tissue tack member 712 may be configured to threadably couple with a bone anchor member within a through aperture of the bone to retain or fix the associated soft tissue to the bone, as described above. The description of such common aspects, elements and/or functions of the soft tissue tack member 612 that are the same or similar in structure and/or function, at least in part, to that of the soft tissue tack member 10, the soft tissue tack member 212, the soft tissue tack member 312, soft tissue tack member 412, the soft tissue tack member 512 and/or the soft tissue tack member 612 is not repeated herein for brevity sake. However, it is specifically contemplated that the soft tissue tack member 612 may include components, aspects, configurations, functions or processes that are the same or similar to that of the soft tissue tack member 10, the soft tissue tack member 212, the soft tissue tack member 312, soft tissue tack member 412, the soft tissue tack member 512 and/or the soft tissue tack member 612 (even if not shown/depicted in FIGS. 87-94), and the description above directed thereto (and the alternative embodiments thereof) equally applies to the soft tissue tack member 712.

As shown in FIGS. 87-94, the soft tissue tack member 712 is substantially similar to the soft tissue tack member 612 described above. Soft tissue tack member 712 differs from the soft tissue tack member 612 described above in that it is void of the lip portions of the transition or raised portion 726 of the head or washer portion 716. Rather, the adjustment slot 723 of the head portion 716 is defined by the annular beveled or countersunk concave surface portion 727 and the annular relief surface portion 729. The annular concave surface portion 727 and the annular relief surface portion 729 are circular and extend entirely about the axis of the adjustment slot 723. As such, the adjustment slot 723 itself is circular. The outer beveled concave surface portion 727 and the relief surface portion 729 of the adjustment slot 723 of the head portion 716 may thereby be configured to allow the head portion 716 to articulate over the articulation surface 731 of the adjustment head portion 721 of the shaft portion 718 along/within the defined range of relative angulation or motion about in all directions about the axis of the shaft portion 718 (such as within the range of about 45 degrees from normal to the long axis from the shaft portion 716, or about 30 degrees from normal to the long axis from the shaft portion 716, or about 15 degrees from normal to the long axis from the shaft portion 716).

As may be recognized by those of ordinary skill in the art based on the teachings herein, numerous changes and modifications may be made to the above-described and other embodiments of the present disclosure without departing from the scope of the disclosure. The components of the instruments, guides, systems and related methods as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the instruments, guides, systems and related methods (and components thereof) may include more or fewer components or features than the embodiments as described and illustrated herein. Accordingly, this detailed description of exemplary embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to exemplary embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. A device for retaining soft tissue to a bone, the device comprising:
    a first member comprising a first head portion and a first threaded shaft portion extending from an inner side of the first head portion, the first head portion and the first threaded shaft portion defining a cannulated opening that extends through the first member; and
    a second member comprising a second head portion and a second threaded shaft portion extending from an inner side of the second head portion, the second head portion and the second threaded shaft portion defining a cannulated opening that extends through the second member,
    wherein the inner side of the first head portion comprises a row of teeth extending about the periphery of the first head portion and a plurality of through holes positioned between the first threaded shaft portion and the row of teeth that extend to an outer side of the first head portion that opposes the inner side thereof,
    wherein the first and second threaded shaft portions are configured to threadably engage with each other,
    wherein the outer side of the first head portion includes a first drive opening that is non-circular in cross-section, and
    wherein the inner side of the second head portion comprises a row of angled teeth extending about the periphery of the second head portion and an outer side of the second head portion that opposes the inner side thereof includes a second drive opening that is non-circular in cross-section.

2. The device of claim 1, wherein the cannulated opening of the first member is aligned with and extends from the first drive opening.

3. The device of claim 1, wherein the cannulated opening of the second member is aligned with and extends from the second drive opening.

4. The device of claim 1, wherein the first head portion comprises a convex outer surface profile.

5. The device of claim 1, wherein the second head portion comprises a convex outer surface profile.

6. The device of claim 1, wherein the row of angled teeth of the inner side of the second head portion are angled in a direction extending about an axis of the cannulated opening of the second member that opposes a loosening direction of the threads of the first threaded shaft portion with respect to the second threaded shaft portion.

7. The device of claim 6, wherein an outer surface of the row of angled teeth of the inner side of the second head portion define the outer peripheral surface of the second head portion.

8. The device of claim 7, wherein the outer surface of the row of angled teeth of the inner side of the second head portion extend parallel to the axis of the cannulated opening of the second member.

9. The device of claim 1, wherein the teeth of the row of teeth of the inner side of the first head portion define axes that are aligned with an axis of the cannulated opening of the first member.

10. The device of claim 9, wherein an outer surface of the teeth of the row of teeth of the inner side of the first head portion are angled toward the axis of the cannulated opening of the first member as they extend to a tip of the teeth.

11. The device of claim 10, wherein an inner surface of the teeth of the row of teeth of the inner side of the first head portion are angled away from the axis of the cannulated opening of the first member as they extend from the inner surface to the tip of the teeth.

12. The device of claim 1, wherein the teeth of the row of teeth of the inner side of the first head portion taper as they extend from the inner surface to the tip of the teeth.

13. The device of claim 1, wherein the inner side of the first head portion comprises only a single row of teeth.

14. The device of claim 1, wherein the inner side of the first head portion is convex.

15. The device of claim 1, wherein the inner side of the second head portion is convex.

16. The device of claim 1, wherein the plurality of through holes are spaced about an axis of the cannulated opening of the first member.

17. The device of claim 1, wherein the first threaded post portion is externally threaded, and the second threaded post portion is internally threaded in the cannulated opening thereof.

18. The device of claim 1, wherein the second threaded post portion is externally threaded, and the first threaded post portion is internally threaded in the cannulated opening thereof.

19. The device of claim 1, wherein the first member and the second member are of one-piece construction.

20. The device of claim 1, wherein the first head portion and the first threaded shaft portion are separate and distinct components that are coupled together.

21. The device of claim 20, wherein the first head portion is movably coupled with the first threaded shaft portion such that the first head portion comprises up to about 15 degrees of variation of an angle between an axis of the first threaded shaft portion and a plane defined by the first head portion.

* * * * *